United States Patent
Chambers et al.

(10) Patent No.: US 7,153,868 B2
(45) Date of Patent: *Dec. 26, 2006

(54) N-(3-(4-SUBSTITUTED-1-PIPERIDINYL)-1-PHENYLPROPYL) SUBSTITUTED SULFONAMIDES AS NK-3 RECEPTOR ANTAGONISTS

(75) Inventors: Mark Stuart Chambers, Puckeridge (GB); Philip Jones, Pomezia (IT); Helen Jane Szekeres, Roydon (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

This patent is subject to a terminal disclaimer.

(21) Appl. No.: 10/417,360

(22) Filed: Apr. 16, 2003

(65) Prior Publication Data

US 2004/0002504 A1    Jan. 1, 2004

(30) Foreign Application Priority Data

Apr. 18, 2002 (GB) .................. 0208897.9

(51) Int. Cl.
  A61K 31/445 (2006.01)
  C07D 401/06 (2006.01)
(52) U.S. Cl. ............. 514/326; 514/255; 514/256; 514/319; 514/320; 514/324; 546/192; 546/195; 546/196; 546/205; 546/207; 546/211; 544/333; 544/336
(58) Field of Classification Search ............ 514/255, 514/256, 319, 320, 324, 326; 546/192, 195, 546/196, 205, 207, 212; 544/333, 336
See application file for complete search history.

(56) References Cited

U.S. PATENT DOCUMENTS

| | | | |
|---|---|---|---|
| 5,741,910 A | | 4/1998 | Bichon et al. |
| 6,511,994 B1 * | | 1/2003 | Kim et al. ............ 514/319 |
| 2003/0105079 A1 * | | 6/2003 | Choi et al. ............ 514/217.12 |

OTHER PUBLICATIONS

Fouget et al. "4-benzylpiperidine sigma receptor ligands" CA 120:163993 (1994).*
Chambers et al. "Preparation of N-(3-(4-substituted piperidin . . ." CA 140:77142.*
Kim et al. "Preparation of 4-pyrazolylpiperidines . . . " CA 138:39281 (2002).*
Wermuth "The practice of medicinal chemistry" Aca. Press, pp. 211-213 (1996).*
Patani et al. "Bioisosterism . . . " Che. Rev. p. 3147 (1996).*
Giardina and Ravegli, *Exp. Opin. Ther. Patents* (1997) 7(4): 307-323.
Giardina et al, *Exp. Opin. Ther. Patents* (2000) 10(6): 939-960.

* cited by examiner

Primary Examiner—Celia Chang
(74) Attorney, Agent, or Firm—J. Eric Thies; Melvin Winokur

(57) ABSTRACT

The present invention provides a method of treatment of a subject suffering from a disease, such as schizophrenia, for which the administration of an NK-3 antagonist is indicated which comprises administering to that subject a therapeutically effective amount of a compound of formula I:

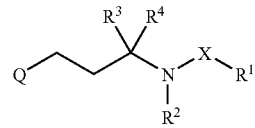

wherein, generally,
Q is

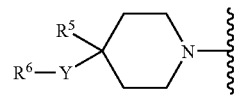

$R^1$ is benzyl, phenyl, thiophene or imidazolyl optionally substituted with $C_{1-4}$alkyl or halogen, such as methyl, fluorine or bromine;
$R^2$ is hydrogen or $C_{1-4}$alkyl such as methyl;
$R^3$ is phenyl;
$R^4$ is hydrogen;
$R^5$ is hydrogen or $C_{1-6}$alkylcarbonyl such as methylcarbonyl;
X is —$SO_2$— or —$C(O)N(R^2)SO_2$— where $R^2$ is preferably hydrogen;
Y is a bond, $CH_2$ or $Z^1$ where $Z^1$ is —$N(R^f)$— in which $R^f$ is $C_{1-6}$alkylcarbonyl such as ethylcarbonyl; and
$R^6$ is phenyl, pyrazolyl, pyridyl, pyrimidinyl or benzimidazolonyl optionally substituted with one or two groups chosen from $C_{1-6}$alkyl and benzyl, such as methyl, ethyl and benzyl;
or a pharmaceutically acceptable salt thereof.

11 Claims, No Drawings

N-(3-(4-SUBSTITUTED-1-PIPERIDINYL)-1-PHENYLPROPYL) SUBSTITUTED SULFONAMIDES AS NK-3 RECEPTOR ANTAGONISTS

CROSS REFERENCE TO RELATED APPLICATIONS

This application claims priority under 35 U.S.C. § 119 from GB Application No. 0208897.9 filed Apr. 18, 2002.

The present invention relates to the use of compounds defined herein for the manufacture of a medicament for treating diseases mediated by neurokinin-3 (NK-3) receptors. These compounds can thus be used in methods of treatment to suppress and treat such disorders.

Background information on NK-3 receptor antagonists can be found in literature reviews such as Giardina and Raveglia, Exp. Opin. Ther. Patents (1997) 7(4): 307–323 and Giardina et al, Exp. Opin. Ther. Patents (2000) 10(6): 939–960. These references also contain pertinent information on preclinical validation of therapies that can be treated with NK-3 antagonists.

Representative examples of compounds prepared in the art as NK-3 antagonists are to be found in WO-A-9719926 (SmithKline Beecham S.p.a.) and U.S. Pat. No. 5,741,910 (Sanofi).

The present invention thus provides a method of treatment of a subject suffering from a disease for which the administration of an NK-3 antagonist is indicated which comprises administering to that subject a therapeutically effective amount of a compound of Formula (I):

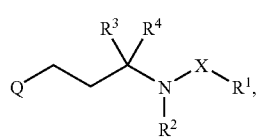

wherein
Q is

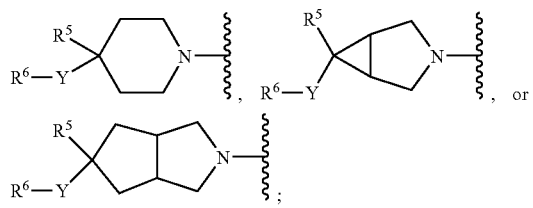

wherein ⁓ denotes the point of attachment;

$R^1$ is $C_{1-8}$ alkyl, $C_{2-8}$ alkenyl, $C_{2-8}$ alkynyl, $C_{3-8}$ cycloalkyl, $C_{5-8}$ cycloalkenyl, —O—$C_{3-8}$ cycloalkyl, —$NR^aR^b$, phenyl, naphthyl, or heterocycle; wherein any one of which except —$NR^aR^b$, is optionally substituted with one or more substituents independently selected from:
(a) halo,
(b) cyano,
(c) —OH,
(d) $C_{1-6}$ alkyl,
(e) —O—$C_{1-6}$ alkyl,
(f) $C_{1-6}$ haloalkyl,
(g) —O—$C_{1-6}$ haloalkyl,
(h) $C_{3-6}$ cycloalkyl,
(i) —O—$C_{3-6}$ cycloalkyl,
(j) $C_{2-6}$ alkenyl,
(k) —$NO_2$,
(l) phenyl, which is optionally substituted with one or more substituents independently selected from $C_{1-4}$ alkyl, —O—$C_{1-4}$ alkyl, halo, and —$CO_2R^c$,
(m) —$CO_2R^c$,
(n) —$NR^cR^d$,
(o) —$NR^c$—$COR^d$,
(p) —$NR^c$—$CO_2R^d$,
(q) —CO—$NR^cR^d$,
(r) —OCO—$NR^cR^d$,
(s) —$NR^cCO$—$NR^cR^d$,
(t) —$S(O)_p$—$R^c$,
(u) —$S(O)_2$—$NR^cR^d$,
(v) —$NR^cS(O)_2$—$R^d$,
(w) —$NR^cS(O)_2$—$NR^cR^d$,
(x) oxo,
(y) heterocyclyl, which is optionally substituted with one or more substituents independently selected from $C_{1-4}$ alkyl, —O—$C_{1-4}$ alkyl, halo, —$CO_2R^c$, and oxo,
(z) —$C_{5-7}$ cycloalkenyl, and
(aa) —C(=O)$R^c$;

X is —$SO_2$— or —C(=O)N($R^e$)$SO_2$—;

$R^2$ is hydrogen or $C_{1-8}$ alkyl which is optionally substituted with one or more substituents independently selected from halo, —$C_{1-6}$ haloalkyl, —O—$C_{1-6}$ alkyl, —O—$C_{1-6}$ haloalkyl, $C_{3-6}$ cycloalkyl, and —O—$C_{3-6}$ cycloalkyl;

or alternatively $R^1$ and $R^2$ together with the N to which $R^2$ is attached and the X, as defined above, to which $R^1$ is attached, form a 4- to 8-membered monocyclic ring containing from 1 to 3 nitrogen atoms, zero to 2 oxygen atoms, and zero to 2 sulfur atoms; wherein the ring is optionally substituted on one or more ring carbons with one or more substituents independently selected from:
(a) halo,
(b) cyano,
(c) —OH,
(d) $C_{1-6}$ alkyl,
(e) —O—$C_{1-6}$ alkyl,
(f) $C_{1-6}$ haloalkyl, and
(g) —$S(O)_p$—$R^c$;

$R^3$ is hydrogen, —CO—$NR^cR^d$, or $C_{1-4}$ alkyl; wherein the alkyl is optionally substituted with one or more substituents independently selected from halo, —OH, —O—$C_{1-4}$ alkyl, or —O—$C_{1-4}$ haloalkyl;

$R^4$ is phenyl, naphthyl, or heterocycle, any one of which is optionally substituted with one or more substituents independently selected from
(a) halo,
(b) —CN,
(c) —OH,
(d) $C_{1-6}$ alkyl,
(e) —O—$C_{1-6}$ alkyl,
(f) $C_{1-6}$ haloalkyl,
(g) —$NO_2$,
(h) phenyl,
(i) —$CO_2R^c$,
(j) —$NR^cR^d$,
(k) —$NR^c$—$COR^d$,
(l) —$NR^c$—$CO_2R^d$,
(m) —CO—$NR^cR^d$,
(n) —OCO—$NR^cR^d$,
(o) —$NR^cCO$—$NR^cR^d$, (p) —S(O)$_p$—R$^c$, wherein p is an integer selected from 0, 1 and 2,
(q) —S(O)$_2$—NR$^c$R$^d$,
(r) —NR$^c$S(O)$_2$—R$^d$,
(s) —NR$^c$S(O)$_2$—NR$^c$R$^d$,
(t) C$_{3-6}$ cycloalkyl,
(u) —O—C$_{3-6}$ cycloalkyl,
(v) —O—C$_{1-6}$ haloalkyl,
(w) C$_{2-6}$ alkenyl and
(x) oxo;

R$^5$ is:
(1) hydrogen,
(2) C$_{1-6}$ alkyl, which is optionally substituted with 1–4 substituents independently selected from —OH, cyano, and halo,
(3) cyano,
(4) —OH,
(5) halo, or
(6) C$_{1-6}$alkylcarboxy;

Y is:
(1) a direct single bond;
(2) —C$_{1-10}$ alkyl- or —(C$_{0-6}$ alkyl)C$_{3-6}$cycloalkyl(C$_{0-6}$ alkyl)-, either of which is optionally substituted with 1–7 substituents independently selected from:
  (a) halo,
  (b) —OH,
  (c) —O—C$_{1-3}$ alkyl,
  (d) trifluoromethyl,
  (e) —(C$_{1-3}$ alkyl)hydroxy, and
  (f) ethylenedioxy;
(3) —(C$_{0-6}$ alkyl)-Z$^1$-(C$_{0-6}$ alkyl)-, wherein each alkyl is optionally substituted with 1–7 substituents independently selected from:
  (a) halo,
  (b) —OH,
  (c) —O—C$_{1-3}$ alkyl, and
  (d) trifluoromethyl;
and where Z$^1$ is selected from —SO$_2$—, —N(R$^f$)—, —N(R$^f$)C(=CHR$^u$)N(R$^f$)—, —N(R$^f$)C(=NR$^u$)N(R$^f$)—, —S—, —O—, —SO—, —SO$_2$N(R$^f$)—, —N(R$^f$)SO$_2$—, and —PO$_2$—;
(4) —(C$_{0-6}$ alkyl)-Z$^2$-(C$_{0-6}$ alkyl)-, wherein each alkyl is optionally substituted with 1–7 substituents independently selected from:
  (a) halo,
  (b) —OH,
  (c) —O—C$_{1-3}$ alkyl, and
  (d) trifluoromethyl;
and where Z$^2$ is selected from —C(=O)—, —C(=O)O—, —OC(=O)—, —C(=O)NRg—, —NRgC(=O)—, —OC(=O)NRg—, —NRgC(=O)O—, and —NR$^h$C(=O)NRg—;

R$^6$ is phenyl, naphthyl, indanyl, tetrahydronaphthyl, biphenyl, or heterocycle; wherein any one of which is optionally substituted with 1–7 substituents independently selected from:
(a) halo,
(b) cyano,
(c) —OH,
(d) C$_{1-6}$ alkyl, which is unsubstituted or substituted with 1–5 of R$^7$,
(e) —O—C$_{1-6}$ alkyl, which is unsubstituted or substituted with 1–5 of R$^7$,
(f) —O—phenyl, which is unsubstituted or substituted with 1–5 of R$^8$,
(g) —O—heterocycle, which is unsubstituted or substituted with 1–5 of R$^8$,
(h) —NO$_2$,
(i) phenyl,
(j) —CO$_2$R$^s$,
(k) tetrazolyl,
(l) —NR$^s$R$^t$,
(m) —NR$^s$—COR$^t$,
(n) —NR$^s$—CO$_2$R$^t$,
(o) —CO—NR$^s$R$^t$,
(p) —OCO—NR$^s$R$^t$,
(q) —NR$^s$CO—NR$^s$R$^t$,
(r) —S(O)$_p$—R$^s$,
(s) —S(O)$_2$—NR$^s$R$^t$,
(t) —NR$^s$S(O)$_2$—R$^t$,
(u) —NR$^s$S(O)$_2$—NR$^s$R$^t$,
(v) C$_{2-6}$ alkenyl,
(w) furanyl, which is unsubstituted or substituted with benzyl which is unsubstituted or substituted with 1–7 of R$^8$,
(x) —C$_{3-6}$ cycloalkyl, and
(y) —O—C$_{3-6}$ cycloalkyl;

each R$^7$ is independently halo, cyano, —OH, —O—C$_{1-6}$ alkyl, —C$_{3-6}$ cycloalkyl, —CO$_2$H, —CO$_2$—(C$_{1-6}$ alkyl), —CF$_3$, —SO$_2$R$^s$, —NR$^s$R$^t$, phenyl, naphthyl, biphenyl, or heterocycle; wherein phenyl, naphthyl, biphenyl, or heterocycle is optionally substituted with 1–7 of R$^8$;

each R$^8$ is independently halo, cyano, —OH, C$_{1-6}$ alkyl, C$_{1-6}$ haloalkyl, —O—C$_{1-6}$ alkyl, —O—C$_{1-6}$ haloalkyl, —CO$_2$H, —CO$_2$(C$_{1-6}$ alkyl), —NR$^s$R$^t$, —(C$_{1-6}$ alkyl)-NR$^s$R$^t$, —SO$_2$R$^s$, —N(R$^s$)SO$_2$R$^t$, —N(R$^s$)COR$^t$, —(C$_{1-6}$ alkyl)-OH, —O—C$_{3-6}$ cycloalkyl, benzyloxy, phenoxy, or —NO$_2$;

each of R$^a$ and R$^b$ is independently C$_{1-6}$ alkyl which is optionally substituted with one or more substituents independently selected from C$_{3-6}$ cycloalkyl, halo, CF$_3$, —O—C$_{1-6}$ alkyl, and —O—C$_{3-6}$ cycloalkyl;

each R$^c$ is independently hydrogen or C$_{1-4}$ alkyl;
each R$^d$ is independently hydrogen or C$_{1-4}$ alkyl;
R$^e$ is hydrogen or C$_{1-4}$ alkyl;
R$^f$ is hydrogen, C$_{1-6}$ alkyl, C$_{2-6}$ alkenyl, benzyl, phenyl, C(O)C$_{1-6}$ alkyl, —SO$_2$—C$_{1-6}$ alkyl, —SO$_2$-phenyl, —SO$_2$-heterocycle, or C$_{1-6}$ alkyl-C$_{3-6}$ cycloalkyl; wherein any of which except hydrogen is optionally substituted with 1–3 substituents independently selected from halo, C$_{1-3}$ alkyl, —O—C$_{1-3}$ alkyl and trifluoromethyl;

R$^g$ is hydrogen, C$_{1-6}$ alkyl, C$_{2-6}$ alkenyl, C$_{2-6}$ alkynyl, benzyl, phenyl, or C$_{1-6}$ alkyl-C$_{3-6}$ cycloalkyl; wherein any of which except hydrogen is optionally substituted with 1–3 substituents independently selected from halo, C$_{1-3}$ alkyl, —O—C$_{1-3}$ alkyl and trifluoromethyl;

R$^h$ is hydrogen or C$_{1-6}$ alkyl;
each R$^s$ is independently hydrogen, C$_{1-6}$ alkyl, C$_{5-6}$ cycloalkyl, benzyl or phenyl;
wherein any of which except hydrogen is optionally substituted with 1–3 substituents independently selected from halo, C$_{1-3}$ alkyl, —O—C$_{1-3}$ alkyl and trifluoromethyl;

each R$^t$ is independently hydrogen, C$_{1-6}$ alkyl, C$_{5-6}$ cycloalkyl, benzyl or phenyl;
wherein any of which except hydrogen is optionally substituted with 1–3 substituents independently selected from halo, C$_{1-3}$ alkyl, —O—C$_{1-3}$ alkyl and trifluoromethyl;

R$^u$ is hydrogen, C$_{1-4}$ alkyl, —NO$_2$ or —CN; and
each p is independently an integer equal to 0, 1, or 2;
and with the proviso that when Q is

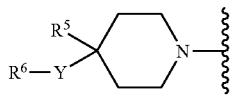

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted as defined above;

or a pharmaceutically acceptable salt thereof.

In particular the method treats CNS disorders such as anxiety, psychosis, depression, Huntington's Disease, epilepsy, schizophrenia, panic, movement and convulsive disorders and Parkinson's disease. Schizophrenia is one typical indication.

The medicament may also be for treating neurodegenerative disorders such as Alzheimer's disease, AMDs related dementia and neuropathological disorders.

Other diseases for which medicaments can be made include ophthalmic diseases such as ocular inflammation, conjunctivitis and vernal conjunctivitis; cardiovascular disorders such as hypertension, cardiac insufficiency and rhythm disorders; disorders of the kidneys or bladder such as incontinence and neurogenic bladder; disorders of blood flow such as angina, migraine and Reynaud's disease; as well as pain such as diabetic neuropathy.

There is also provided a method for treating a patient suffering from an NK-3 receptor mediated disease, as detailed above, which comprises administering to that patient a therapeutically effective amount of a compound of formula I, or a pharmaceutically acceptable salt thereof, as defined herein.

In one embodiment $R^5$ is:
(1) hydrogen,
(2) $C_{1-6}$ alkyl, which is optionally substituted with 1–4 substituents independently selected from —OH, cyano, and halo,
(3) cyano,
(4) —OH, or
(5) halo.

A first embodiment of the present invention is a compound of Formula I as just defined above, except that:
(A) the definition of $R^1$ does not include $C_{5-8}$ cycloalkenyl,
(B) in the definition of $R^1$, the list of possible substituents does not include (z) and (aa), and substituent (y) is defined as heterocyclyl, which is optionally substituted with one or more substituents independently selected from $C_{1-4}$ alkyl, —O—$C_{1-4}$ alkyl, halo, and —$CO_2R^c$; and
(C) X is —$SO_2$—.

A second embodiment of the present invention is a compound of Formula I, wherein $R^1$ is $C_{1-8}$ alkyl, —O—$C_{1-8}$ alkyl, $C_{2-8}$ alkenyl, $C_{2-8}$ alkynyl, $C_{3-8}$ cycloalkyl, $C_{5-8}$ cycloalkenyl, —O—$C_{3-8}$ cycloalkyl, —$NR^aR^b$, phenyl, naphthyl, or a heterocycle selected from:
(i) a 4- to 6-membered saturated heterocycle containing from 1 to 3 heteroatoms selected from nitrogen, oxygen and sulfur,
(ii) a 5- to 6-membered heteroaromatic ring containing from 1 to 3 heteroatoms selected from nitrogen, oxygen, and sulfur; and
(iii) an 8- to 10-membered bicyclic heterocycle containing from 1 to 4 heteroatoms selected from nitrogen, oxygen and sulfur, either ring of which is saturated or unsaturated;

wherein any one of $R^1$ is optionally substituted with one or more substituents independently selected from:
(a) halo,
(b) cyano,
(c) —OH,
(d) $C_{1-4}$ alkyl,
(e) —O—$C_{1-4}$ alkyl,
(f) $C_{1-4}$ haloalkyl,
(g) —O—$C_{1-4}$ haloalkyl,
(h) —$NO_2$,
(i) phenyl,
(j) —$CO_2R^c$,
(k) —$NR^cR^d$,
(l) —$NR^c$—$COR^d$,
(m) —$NR^c$—$CO_2R^d$,
(n) —CO—$NR^cR^d$,
(o) —OCO—$NR^cR^d$,
(p) —$NR^cCO$—$NR^cR^d$,
(q) —$S(O)_p$—$R^c$, wherein p is an integer selected from 0, 1 and 2,
(r) —$S(O)_2$—$NR^cR^d$,
(s) —$NR^cS(O)_2$—$R^d$,
(t) —$NR^cS(O)_2$—$NR^cR^d$,
(u) oxo, and
(v) —C(=O)$R^c$;

and all other variables are as originally defined; and with the proviso that when Q is

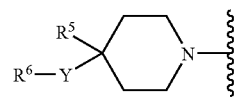

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;

or a pharmaceutically acceptable salt thereof.

An aspect of the second embodiment is a compound of Formula I exactly as defined in the first embodiment, except that the definition of $R^1$ does not include $C_{5-8}$ cycloalkenyl, the list of possible substituents on $R^1$ does not include (v)

—C(=O)$R^c$.

In another aspect of the second embodiment, $R^1$ is:
(i) $C_{1-4}$ alkyl which is optionally substituted with a substituent selected from:
(a) cyano,
(b) —O—$C_{1-4}$ alkyl,
(c) —$C_{3-6}$ cycloalkyl,
(d) —$C_{5-6}$ cycloalkenyl,
(e) —$CO_2H$,
(f) —$S(O)_2$—$NR^cR^d$,
(g) —S—$C_{1-4}$ alkyl, and
(h) a 5- or 6-membered saturated or unsaturated heterocycle containing from 1 to 3 heteroatoms selected from N, O and S, wherein the heterocycle is optionally substituted with 1 or 2 substituents independently selected from —$C_{1-6}$ alkyl and oxo;
(ii) cycloalkyl selected from cyclopropyl, cyclobutyl, cyclopentyl, and cyclohexyl, which is optionally substituted with from 1 to 3 substituents independently selected from:
(a) halo,
(b) —OH,
(c) cyano, (d) $C_{1-6}$ alkyl, and
  (e) —$CO_2H$;
 (iii) phenyl which is optionally substituted with from 1 to 3 substituents independently selected from:
  (a) halo,
  (b) cyano,
  (c) $C_{1-6}$ alkyl,
  (d) —O—$C_{1-6}$ alkyl,
  (e) $C_{1-6}$ haloalkyl,
  (f) —O—$C_{1-4}$ haloalkyl, and
  (g) —$CO_2H$;
 (iv) a 4- to 6-membered saturated heterocycle selected from the group consisting of azetidinyl, oxacyclobutyl, pyrrolidinyl, tetrahydrofuranyl, 1,3-dioxacyclopentyl, morpholinyl, thiomorpholinyl, thiazolidinyl, oxazolidinyl, isooxazolidinyl, imidazolidinyl, piperazinyl, tetrahydrofuranyl, 1,4-dioxanyl, 1,3-dioxanyl, oxacyclohexyl, piperidinyl, and oxacyclopentyl; wherein the heterocycle is optionally substituted with from 1–3 substituents independently selected from:
  (a) halo,
  (b) cyano,
  (c) $C_{1-6}$ alkyl,
  (d) —O—$C_{1-6}$ alkyl,
  (e) $C_{1-6}$ haloalkyl,
  (f) —O—$C_{1-4}$ haloalkyl,
  (g) $C_{3-6}$ cycloalkyl,
  (h) —O—$C_{3-6}$ cycloalkyl,
  (i) $C_{2-6}$ alkenyl,
  (j) phenyl,
  (k) oxo, and
  (l) —C(=O)$R^c$;
 (v) a 5- to 6-membered heteroaromatic selected from the group consisting of thienyl, pyridyl, imidazolyl, pyrrolyl, pyrazolyl, thiazolyl, isothiazolyl, pyrazinyl, pyrimidinyl, triazolyl, tetrazolyl, furanyl, oxazolyl, and isoxazolyl; wherein the heteroaromatic is optionally substituted with from 1–3 substituents independently selected from:
  (a) halo,
  (b) cyano,
  (c) $C_{1-6}$ alkyl,
  (d) —O—$C_{1-6}$ alkyl,
  (e) $C_{1-6}$ haloalkyl,
  (f) —O—$C_{1-4}$ haloalkyl,
  (g) $C_{3-6}$ cycloalkyl,
  (h) —O—$C_{3-6}$ cycloalkyl,
  (i) $C_{2-6}$ alkenyl,
  (j) phenyl, and
  (k) oxo;
 (vi) an 8- to 10-membered bicyclic heterocycle selected from the group consisting of benzimidazolyl, pyridoimidazolyl, indolyl, isoindolyl, phthalazinyl, purinyl, quinoxalinyl, quinazolinyl, cinnolinyl, quinolinyl, isoquinolinyl, indazolyl, dihydroindolyl, dihydroisoindolyl, tetrahydroquinolyl, tetrahydroisoquinolyl, and pyridopyrazolyl; wherein the bicyclic heterocycle is optionally substituted with from 1–3 substituents independently selected from:
  (a) halo,
  (b) cyano,
  (c) $C_{1-6}$ alkyl,
  (d) —O—$C_{1-6}$ alkyl,
  (e) $C_{1-6}$ haloalkyl,
  (f) —O—$C_{1-4}$ haloalkyl,
  (g) $C_{3-6}$ cycloalkyl,
  (h) —O—$C_{3-6}$ cycloalkyl,
  (i) $C_{2-6}$ alkenyl,
  (j) phenyl, and
  (k) oxo.

In still another aspect of the second embodiment, $R^1$ is:
 (i) a 4- to 6-membered saturated heterocycle selected from the group consisting of azetidinyl, oxacyclobutyl, pyrrolidinyl, tetrahydrofuranyl, 1,3-dioxacyclopentyl, morpholinyl, thiomorpholinyl, thiazolidinyl, oxazolidinyl, isooxazolidinyl, imidazolidinyl, piperazinyl, tetrahydrofuranyl, 1,4-dioxanyl, 1,3-dioxanyl, oxacyclohexyl, and piperidinyl; wherein the heterocycle is optionally substituted with from 1–3 substituents independently selected from:
  (a) halo,
  (b) cyano,
  (c) $C_{1-6}$ alkyl,
  (d) —O—$C_{1-6}$ alkyl,
  (e) $C_{1-6}$ haloalkyl,
  (f) —O—$C_{1-4}$ haloalkyl,
  (g) $C_{3-6}$ cycloalkyl,
  (h) —O—$C_{3-6}$ cycloalkyl,
  (i) $C_{2-6}$ alkenyl,
  (j) phenyl, and
  (k) oxo;
 (ii) a 5- to 6-membered heteroaromatic selected from the group consisting of thienyl, pyridyl, imidazolyl, pyrrolyl, pyrazolyl, thiazolyl, isothiazolyl, pyrazinyl, pyrimidinyl, triazolyl, and tetrazolyl; wherein the heteroaromatic is optionally substituted with from 1–3 substituents independently selected from:
  (a) halo,
  (b) cyano,
  (c) $C_{1-6}$ alkyl,
  (d) —O—$C_{1-6}$ alkyl,
  (e) $C_{1-6}$ haloalkyl,
  (f) —O—$C_{1-4}$ haloalkyl,
  (g) $C_{3-6}$ cycloalkyl,
  (h) —O—$C_{3-6}$ cycloalkyl,
  (i) $C_{2-6}$ alkenyl,
  (j) phenyl, and
  (k) oxo;
 (iii) an 8- to 10-membered bicyclic heterocycle selected from the group consisting of benzimidazolyl, pyridoimidazolyl, indolyl, isoindolyl, phthalazinyl, purinyl, quinoxalinyl, quinazolinyl, cinnolinyl, quinolinyl, isoquinolinyl, indazolyl, dihydroindolyl, dihydroisoindolyl, tetrahydroquinolyl, tetrahydroisoquinolyl, and pyridopyrazolyl; wherein the bicyclic heterocycle is optionally substituted with from 1–3 substituents independently selected from:
  (a) halo,
  (b) cyano,
  (c) $C_{1-6}$ alkyl,
  (d) —O—$C_{1-6}$ alkyl,
  (e) $C_{1-6}$ haloalkyl,
  (f) —O—$C_{1-4}$ haloalkyl,
  (g) $C_{3-6}$ cycloalkyl,
  (h) —O—$C_{3-6}$ cycloalkyl,
  (i) $C_{2-6}$ alkenyl,
  (j) phenyl, and
  (k) oxo.

A third embodiment of the present invention is a compound of Formula I, wherein $R^2$ is hydrogen or $C_{1-6}$ alkyl which is optionally substituted with one or more substituents independently selected from fluoro, —$CF_3$, —O—$C_{1-4}$ alkyl, $C_{3-6}$ cycloalkyl, and —O—$C_{3-6}$ cycloalkyl;
and all other variables are as originally defined;
and with the proviso that when Q is

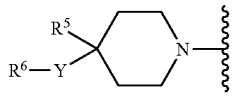

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;
or a pharmaceutically acceptable salt thereof.

A fourth embodiment of the present invention is a compound of Formula I, wherein $R^3$ is hydrogen;
and all other variables are as originally defined;
and with the proviso that when Q is

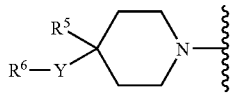

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;
or a pharmaceutically acceptable salt thereof.

A fifth embodiment of the present invention is a compound of Formula I, wherein $R^4$ is phenyl or heterocycle, wherein the phenyl or heterocycle is optionally substituted with from 1 to 4 substituents independently selected from
(a) halo,
(b) —CN,
(c) —OH,
(d) $C_{1-4}$ alkyl,
(e) —O—$C_{1-4}$ alkyl,
(f) $CF_3$,
(g) —$NO_2$,
(h) phenyl,
(i) —$CO_2R^c$,
(j) —$NR^cR^d$,
(k) —$NR^c$—$COR^d$,
(l) —$NR^c$—$CO_2R^d$,
(m) —CO—$NR^cR^d$,
(n) —OCO—$NR^cR^d$,
(o) —$NR^c$CO—$NR^cR^d$,
(p) —$S(O)_p$—$R^c$,
(q) —$S(O)_2$—$NR^cR^d$,
(r) —$NR^cS(O)_2$—$R^d$,
(s) —$NR^cS(O)_2$—$NR^cR^d$,
(t) $C_{3-6}$ cycloalkyl, and
(u) —O—$C_{3-6}$ cycloalkyl;
and all other variables are as originally defined;
and with the proviso that when Q is

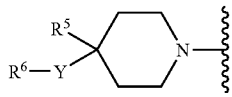

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;
or a pharmaceutically acceptable salt thereof.

A sixth embodiment of the present invention is a compound of Formula I, wherein $R^5$ is hydrogen or fluoro;
and all other variables are as originally defined;
and with the proviso that when Q is

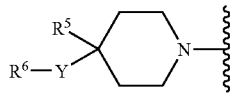

and Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;
or a pharmaceutically acceptable salt thereof.

In an aspect of the sixth embodiment, $R^5$ is hydrogen.
A seventh embodiment of the present invention is a compound of Formula I, wherein Y is
(1) a direct single bond;
(2) —$C_{1-6}$ alkyl-, which is optionally substituted with 1–7 substituents independently selected from:
(a) halo,
(b) —OH,
(c) —O—$C_{1-3}$ alkyl, and
(d) trifluoromethyl;
(3) —($C_{0-2}$ alkyl)-$Z^1$-($C_{0-2}$ alkyl)-, wherein the alkyl is unsubstituted;
$Z^1$ is selected from —$SO_2$—, —SO—, —N($R^f$)—, —$SO_2N(R^f)$—, —S—, and —O—;
and $R^f$ is $C_{1-4}$ alkyl, $C_{2-5}$ alkenyl, or $C_{1-3}$ alkyl-$C_{3-6}$ cycloalkyl; or
(4) —($C_{0-2}$ alkyl)-$Z^2$-($C_{0-2}$ alkyl)-, wherein the alkyl is optionally substituted with 1–4 substituents independently selected from:
(a) halo,
(b) —OH,
(c) —O—$C_{1-3}$ alkyl, and
(d) trifluoromethyl;
and wherein
$Z^2$ is selected from —C(=O)NRg—, —NRgC(=O)—, —OC(=O)NRg—, —NRgC(=O)O—, and —$NR^h$C(=O)NRg—;
$R^g$ is hydrogen, $C_{1-6}$ alkyl, $C_{2-6}$ alkenyl, $C_{2-6}$ alkynyl, benzyl, phenyl, or $C_{1-6}$ alkyl-$C_{3-6}$ cycloalkyl; wherein any of which except hydrogen is optionally substituted with from 1 to 3 substituents independently selected from halo, $C_{1-3}$ alkyl, —O—$C_{1-3}$ alkyl and trifluoromethyl; and
$R^h$ is —H or $C_{1-6}$ alkyl;
and all other variables are as originally defined;
and with the proviso that when Q is

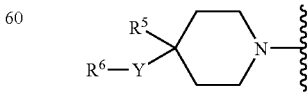

and Y is a direct single bond, then $R^6$ is phenyl, naphthyl, indanyl, tetrahydronaphthyl, biphenyl, or a heterocycle selected from pyrazolyl and tetrahydropyridopyrazolyl;

wherein any one of which is optionally substituted in the manner originally defined above;
or a pharmaceutically acceptable salt thereof.

In one aspect of the seventh embodiment, Y is
(1) a direct single bond;
(2) —$C_{2-4}$ alkyl-, which is optionally substituted with 1–6 substituents independently selected from:
   (a) halo,
   (b) —O—$C_{1-3}$ alkyl, and
   (c) trifluoromethyl;
(3) selected from
   —($C_{0-2}$ alkyl)-$SO_2$—($C_{0-2}$ alkyl)-,
   —($C_{0-2}$ alkyl)-$SO_2N(R^f)$—($C_{0-2}$ alkyl),
   —($C_{0-2}$ alkyl)-SO—($C_{0-2}$ alkyl)-,
   —($C_{0-2}$ alkyl)-S—($C_{0-2}$ alkyl)-,
   —($C_{0-2}$ alkyl)-O—($C_{0-2}$ alkyl)-, and
   —($C_{0-2}$ alkyl)-$N(R^f)$—($C_{0-2}$ alkyl)-; and
   where $R^f$ is $C_{2-4}$ alkyl, $C_{2-3}$ alkenyl or $C_{1-2}$ alkyl-$C_3$ cycloalkyl;
(4) —($C_{0-2}$ alkyl)-$Z^2$-($C_{0-2}$ alkyl)-, wherein the alkyl is not substituted; and where
   $Z^2$ is selected from —C(=O)NRg—, —NRgC(=O)—, —OC(=O)NRg—, —NRgC(=O)O—, and —$NR^h$C(=O)NRg—;
   $R^g$ is hydrogen, $C_{1-3}$ alkyl, $C_{2-3}$ alkenyl, or $C_{2-3}$ alkynyl; and
   $R^h$ is —H or $C_{1-4}$ alkyl.

In another aspect of the seventh embodiment, Y is
(1) a direct single bond;
(2) $C_{2-4}$ alkyl, which is optionally substituted with from 1 to 6 fluoros;
(3) selected from:
   (a) —$SO_2CH_2CH_2$—,
   (b) —SO—$CH_2CH_2$—,
   (c) —$SCH_2CH_2$—,
   (d) —$CH_2$—O—$CH_2$—.
   (e) —$N(CH_2CH_3)$—,
   (f) —$N(CH_2CH_2CH_3)$—, and
   (g) —$N(CH_2$-cyclopropyl)-; or
(4) selected from:
   (a) —$CH_2OC(=O)$—$N(C_{1-4}$ alkyl)-,
   (b) —$CH_2$—OC(=O)N(allyl)-,
   (c) —$CH_2NHC(=O)N(C_{1-4}$ alkyl)-,
   (d) —$CH_2NHC(=O)N(allyl)$, and
   (e) —$CH_2CH_2NHC(=O)N(CH_2CH_3)$—.

In still another aspect of the seventh embodiment, Y is a direct single bond, in which case there is a proviso that when Q is

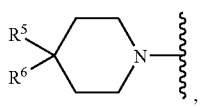

then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined.

An eighth embodiment of the present invention is a compound of Formula I, wherein $R^6$ is phenyl, benzoimidazolyl, imidazolyl, pyridoimidazolyl, isoxazolyl, oxazolyl, pyrazolyl, pyridyl, thiazolyl, imidazothiophenyl, indazolyl, tetrahydropyridoimidazolyl, tetrahydroindazolyl, dihydrothiopyranopyrazolyl, dihydrodioxothiopyranopyrazolyl, dihydropyranopyrazolyl, tetrahydropyridopyrazolyl, or triazolyl (e.g., 1,2,4-triazolyl); wherein any of which is optionally substituted with from 1 to 7 substituents independently selected from:
   (a) halo,
   (b) cyano,
   (c) —OH,
   (d) $C_{1-6}$ alkyl, which is unsubstituted or substituted with 1–5 of $R^7$
   (e) —O—$C_{1-6}$ alkyl, which is unsubstituted or substituted with 1–5 of $R^7$,
   (f) —$NO_2$,
   (g) phenyl,
   (h) —$CO_2R^s$,
   (i) tetrazolyl,
   (j) —$NR^sR^t$,
   (k) —$NR^s$—$COR^t$,
   (l) —$NR^s$—$CO_2R^t$,
   (m) —CO—$NR^sR^t$,
   (n) —OCO—$NR^sR^t$,
   (o) —$NR^s$CO—$NR^sR^t$,
   (p) —$S(O)_p$—$R^s$,
   (q) —$S(O)_2$—$NR^sR^t$,
   (r) —$NR^sS(O)_2$—$R^t$,
   (s) —$NR^sS(O)_2$—$NR^sR^t$,
   (t) —$C_{3-5}$ cycloalkyl, and
   (t) —O—$C_{3-5}$ cycloalkyl;
each $R^7$ is independently halo, cyano, —OH, —O—$C_{1-6}$ alkyl, —$C_{3-5}$ cycloalkyl, —$CO_2H$, —$CO_2(C_{1-6}$ alkyl), —$CF_3$, —$SO_2R^s$, —$NR^sR^t$, phenyl, naphthyl, biphenyl, or heterocycle;
wherein phenyl, naphthyl, biphenyl, or heterocycle is optionally substituted with 1–7 of $R^8$;
each $R^8$ is independently halo, cyano, —OH, $C_{1-4}$ alkyl, —O—$C_{1-4}$ alkyl, —O—$C_{3-5}$ cycloalkyl, —$CO_2H$, —$CO_2$($C_{1-6}$ alkyl), —$CF_3$, —$OCF_3$, —$SO_2R^a$, —$N(R^a)SO_2R^{b^2}$, or —$NR^sR^t$;
each $R^s$ is independently hydrogen, $C_{1-6}$ alkyl, $C_{5-6}$ cycloalkyl, benzyl or phenyl, wherein any of which except hydrogen is optionally substituted with 1–3 substituents independently selected from halo, $C_{1-3}$ alkyl, —O—$C_{1-3}$ alkyl, $C_{1-3}$ fluoroalkyl, and —O—$C_{1-3}$ fluoroalkyl; and
each $R^t$ is independently hydrogen, $C_{1-6}$ alkyl, $C_{5-6}$ cycloalkyl, benzyl or phenyl, wherein any of which except hydrogen is optionally substituted with 1–3 substituents independently selected from halo, $C_{1-3}$ alkyl, —O—$C_{1-3}$ alkyl, $C_{1-3}$ fluoroalkyl, and —O—$C_{1-3}$ fluoroalkyl;
and all other variables are as originally defined;
and with the proviso that when Q is

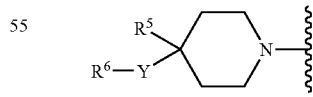

and Y is a direct single bond, then $R^6$ is phenyl or a heterocycle selected from pyrazolyl and tetrahydropyridopyrazolyl; wherein the phenyl or heterocycle is optionally substituted as just defined above;
or a pharmaceutically acceptable salt thereof.

An aspect of the eighth embodiment is a compound of Formula I exactly as defined in the eighth embodiment, except that the definition of $R^6$ does not include triazolyl.

A ninth embodiment of the present invention is a compound of Formula I, wherein $R^6$ is benzimidazolyl, imidazolyl, pyridoimidazolyl, isoxazolyl, oxazolyl, pyrazolyl, pyridyl, thiazolyl, imidazothiophenyl, indazolyl, tetrahydropyridoimidazolyl, tetrahydroindazolyl, dihydrothiopyranopyrazolyl, dihydrodioxothiopyranopyrazolyl, dihydropyranopyrazolyl, tetrahydropyridopyrazolyl, or triazolyl; wherein any of which is optionally substituted with from 1 to 5 substituents independently selected from:

(a) halo,
(b) cyano,
(c) —$NO_2$,
(d) —$CF_3$,
(e) —$CHF_2$,
(f) —$CH_2F$,
(g) —$CH_2OH$,
(h) —$CH_2OCH_3$,
(i) —$(CH_2)_{1-2}SO_2$—($C_{1-2}$ alkyl)
(j) phenyl,
(k) $C_{1-6}$ alkyl, which is optionally substituted with phenyl, which is optionally substituted with from 1 to 4 substituents independently selected from halo, cyano, —OH, —O—$C_{1-6}$ alkyl, —O—$C_{3-5}$ cycloalkyl, —$CO_2H$, —$CO_2(C_{1-6}$ alkyl), —$CF_3$, —$OCF_3$, and —$SO_2$—($C_{1-3}$ alkyl);
(l) —O—$C_{1-6}$ alkyl,
(m) —$C_{3-5}$ cycloalkyl,
(n) —$CH_2$—($C_{3-5}$ cycloalkyl), and
(o) —O—$C_{3-5}$ cycloalkyl;

and all other variables are as originally defined;
and with the proviso that when Q is

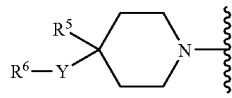

and Y is a direct single bond, then $R^6$ is pyrazolyl or tetrahydropyridopyrazolyl, either of which is optionally substituted as just defined above;
or a pharmaceutically acceptable salt thereof.

An aspect of the ninth embodiment is a compound of Formula I exactly as defined in the ninth embodiment, except that the definition of $R^6$ does not include triazolyl.

A tenth embodiment of the present invention is a compound of Formula I, wherein Q is

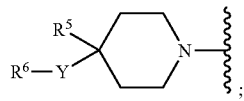

and all other variables are as originally defined;
and with the proviso that when Y is a direct single bond, then $R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined;
or a pharmaceutically acceptable salt thereof.

An eleventh embodiment of the present invention is a compound of Formula I, wherein Q is

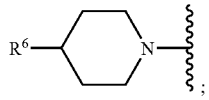

and
$R^6$ is phenyl, naphthyl, indanyl, tetrahydronaphthyl, biphenyl, or a heterocycle selected from pyrazolyl and tetrahydropyridopyrazolyl; wherein any one of which is optionally substituted in the manner originally defined above;
and all other variables are as originally defined;
or a pharmaceutically acceptable salt thereof.

It is to be understood that additional embodiments of the present invention include, but are not limited to, compounds of Formula I wherein each of two or three or more of $R^1$, $R^2$, $R^3$, $R^4$, $R^5$, $R^6$, X, Y and Q is independently defined in accordance with one of the foregoing embodiments or aspects thereof as set forth above. Any and all possible combinations of these variables in Formula I are within the scope of the present invention, subject to the proviso set forth above relating Q, Y and $R^6$.

The compounds of the instant invention have at least one asymmetric center carbon atom substituted by N, $R^3$, $R^4$ and $CH_2CH_2$-Q in Formula I. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention.

Another sub-class of the first class are compounds of Formula (III):

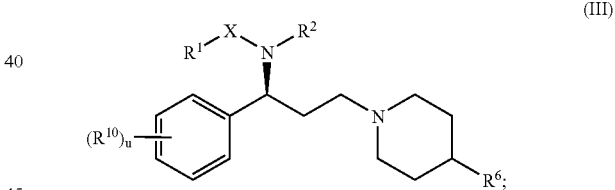

(III)

wherein all of the variables are as defined in the first class above;
or a pharmaceutically acceptable salt thereof.

The independent syntheses of the optical isomers described above or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As used herein, the term "$C_{1-6}$ alkyl" (or "$C_1$–$C_6$ alkyl") means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_{1-4}$ alkyl" means n-, iso-, sec- and t-butyl, n- and isopropyl, ethyl and methyl. Similar terms such as "$C_{1-10}$ alkyl" have analogous meanings.

The term "$C_0$" as employed in expressions such as "$C_{0-6}$ alkyl" means a direct covalent bond.

The term "$C_{2-6}$ alkenyl" (or "$C_2$–$C_6$ alkenyl") means linear or branched chain alkenyl groups having from 2 to 6 carbon atoms and includes all of the hexenyl and pentenyl isomers as well as 1-butenyl, 2-butenyl, 3-butenyl, isobutenyl, 1-propenyl, 2-propenyl, and ethenyl (or vinyl). Similar terms such as "$C_{2-10}$ alkenyl" have analogous meanings.

The term "$C_{2-6}$ alkynyl" (or "$C_2$–$C_6$ alkynyl") means linear or branched chain alkynyl groups having from 2 to 6 carbon atoms and includes all of the hexynyl and pentynyl isomers as well as 1-butynyl, 2-butynyl, 3-butynyl, 1-propynyl, 2-propynyl, and ethynyl (or acetylenyl). Similar terms such as "$C_{2-10}$ alkynyl" have analogous meanings.

The term "$C_{3-8}$ cycloalkyl" (or "$C_3$–$C_8$ cycloalkyl") means a cyclic ring of an alkane having three to eight total carbon atoms (i.e., cyclopropyl, cyclobutyl, cyclopentyl, cyclohexyl, cycloheptyl, or cyclooctyl). The term "$C_{3-6}$ cycloalkyl" refers to a cyclic ring selected from cyclopropyl, cyclobutyl, cyclopentyl, and cyclohexyl. Similar terms such as "$C_{5-6}$ cycloalkyl" have analogous meanings.

The term "halogen" (or "halo") refers to fluorine, chlorine, bromine and iodine (alternatively, fluoro, chloro, bromo, and iodo).

The term "$C_{1-6}$ haloalkyl" (which may alternatively be referred to as "$C_1$–$C_6$ haloalkyl" or "halogenated $C_1$–$C_6$ alkyl") means a $C_1$ to $C_6$ linear or branched alkyl group as defined above with one or more halogen substituents. The term "$C_{1-4}$ haloalkyl" has an analogous meaning. Similarly, "$C_{1-6}$ fluoroalkyl" means a $C_1$ to $C_6$ linear or branched alkyl group as defined above with one or more fluorine substituents. Representative examples of suitable fluoroalkyls include the series $(CH_2)_{0-4}CF_3$ (i.e., trifluoromethyl, 2,2,2-trifluoroethyl, 3,3,3-trifluoro-n-propyl, etc.), 1-fluoroethyl, 2-fluoroethyl, 2,2-difluoroethyl, 3,3,3-trifluoroisopropyl, 1,1,1,3,3,3-hexafluoroisopropyl, and perfluorohexyl.

The term "—$(C_{1-3}$ alkyl)hydroxy" refers to a $C_{1-3}$ alkyl group as defined above which is substituted on one its carbons by a hydroxy group. Exemplary groups include hydroxymethyl, hydroxyethyl, 3-hydroxy-n-propyl, 2-hydroxy-n-propyl, and so forth.

The term "heterocycle" (and variations thereof such as "heterocyclic" or "heterocyclyl") broadly refers to a 4- to 8-membered monocyclic ring, 7- to 14-membered bicyclic ring system, or an 11 to 16-membered tricyclic ring system, any ring of which is saturated or unsaturated, and which consists of carbon atoms and one or more heteroatoms (e.g., from 1 to 4 heteroatoms) selected from N, O and S, and wherein the nitrogen and sulfur heteroatoms may optionally be oxidized, and the nitrogen heteroatom may optionally be quaternized. The heterocyclic ring may be attached at any heteroatom or carbon atom, provided that attachment results in the creation of a stable structure.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dibydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, methylenedioxybenzyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothiopheyl, pyrazolopyridyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl. It also includes benzimidazolonyl.

The terms "thiophenyl" and "thienyl" have the same meaning herein and are used interchangeably. Similarly, the following pairs of terms have the same meaning: "indazolyl" and "benzopyrazolyl"; "pyridinyl" and "pyridyl".

Unless expressly set forth to the contrary, an "unsaturated" ring is a partially or fully unsaturated ring.

The term "substituted" in reference to substitution on alkyl, cycloalkyl, phenyl, heterocycle, or some other chemical group is intended to include mono- and poly-substitution by a named substituent to the extent such single and multiple substitution is chemically allowed in any of the named chemical groups.

It is understood that the definition of a substituent at a particular location in a molecule is independent of its definition at other locations in the molecule. Thus, for example, when $Z^1 = -N(R^f)C(=CHR^u)N(R^f)-$, the value of $R^f$ (defined elsewhere) on one of the nitrogens is independent of the value of $R^f$ at the other nitrogen; i.e., they can be the same or different.

Exemplifying the invention is the use of the compounds disclosed in the Examples.

Exemplary compounds of the present invention include compounds selected from the group consisting of:

N-[1(S)-1-phenyl-3-(4-[3-benzyl-1-ethyl(1H-pyrazol-5-yl)]piperidin-1-yl)propyl]methylsulfonamide;

N-{(1S)-3-[4-(3-benzyl-1-ethyl-1H-pyrazol-5-yl)piperidin-1-yl]-1-phenylpropyl}ethanesulfonamide;

N-{(1S)-3-[4-(3-benzyl-1-ethyl-1H-pyrazol-5-yl)piperidin-1-yl]-1-phenylpropyl}thiophene-2-sulfonamide;

N-[1(S)-1-phenyl-3-(4-[3-ethyl-1-(4-[ethylsulfonyl]benzyl)-(1H-pyrazol-5-yl)-piperidin-1-yl)propyl]cyclobutanecarboxamide;

and pharmaceutically acceptable salts thereof.

A preferred class of compounds is where:

Q is

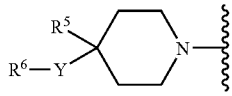

R¹ is benzyl, phenyl, thiophene or imidazolyl optionally substituted with $C_{1-4}$alkyl or halogen, such as methyl, fluorine or bromine;

R² is hydrogen or $C_{1-4}$alkyl such as methyl;

R³ is phenyl;

R⁴ is hydrogen;

R⁵ is hydrogen or $C_{1-6}$alkylcarbonyl such as methylcarbonyl;

X is —SO₂— or —C(O)N(R²)SO₂— where R² is preferably hydrogen;

Y is a bond, CH₂ or Z¹ where Z¹ is —N(R^f)— in which R^f is $C_{1-6}$alkylcarbonyl such as ethylcarbonyl; and R⁶ is phenyl, pyrazolyl, pyridyl, pyrimidinyl or benzimidazolonyl optionally substituted with one or two groups chosen from $C_{1-6}$alkyl and benzyl, such as methyl, ethyl and benzyl;

or a pharmaceutically acceptable salt thereof.

X is preferably —SO₂—.

Particular embodiments of R¹ are thiophen-2-yl, phenyl, 4-methylphenyl, 3-fluorophenyl, 2-fluorophenyl, 4-fluorophenyl, 4-bromophenyl, benzyl, 3-bromophenyl, 5-bromothiophen-2-yl and 1-methylimidazol-4-yl.

Particular embodiments of R⁶ are phenyl, 1-ethyl-3-methylpyrazin-5-yl, 1,3-dimethylpyrazin-5-yl, pyrimidin-3-yl, pyrid-2-yl, 1-methylpyrazin-5-yl, benzimidazolon-1-yl, 1-ethyl-3-benzylpyrazin-5-yl and 2-ethyl-3-methylpyridazin-5-yl.

Particularly preferred subclasses of compounds are as follows where individually:

Q is

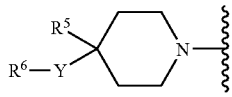

R⁵ is hydrogen

R⁶ is pyrazole, optionally substituted with one or two groups chosen from methyl, ethyl and benzyl, especially 1,3-dimethylpyrazol-5-yl and 1-ethyl-3-benzylpyrazol-5yl;

Y is a single bond or CH₂, preferably a single bond;

R³ is phenyl;

R⁴ is hydrogen;

R² is hydrogen;

X is —SO₂— or C(=O)N(R²)SO₂— where R² is preferably hydrogen; or

R¹ is phenyl or thiophenyl, particularly phenyl or thiophen-2-yl.

Particular compounds of use in the present invention are:

N-{3-[4-(1,3-dimethyl-1H-pyrazol-5-yl)-1-piperidinyl]-1-phenylpropyl}benzenesulfonamide;

N-{3-[4-(1,3-dimethyl-1H-pyrazol-5-yl)-1-piperidinyl]-1-phenylpropyl}-2-thiophenesulfonamide;

N-{3-[4-(1,3-dimethyl-1H-pyrazol-5-yl)-1-piperidinyl]-1-phenylpropyl}-N-methyl-2-thiophenesulfonamide;

N-{1-phenyl-3-[4-(phenylmethyl)-1-piperidinyl]propyl}benzenesulfonamide;

N-{3-[4-(1-ethyl-3-methyl-1H-pyrazol-5-yl)-1-piperidinyl]-1-phenylpropyl}benzenesulfonamide;

N-{3-[4-(1-ethyl-5-methyl-1H-pyrazol-3-yl)-1-piperidinyl]-1-phenylpropyl}benzenesulfonamide;

N-{(1S)-3-[4-(3-benzyl-1-ethyl-1H-pyrazol-5-yl)piperidin-1-yl]-1-phenylpropyl}thiophene-2-sulfonamide, bis trifluoroacetate salt;

4-(3-benzyl-1-ethyl-1H-pyrazol-1-ium-5-yl)-1-[(3S)-3-phenyl-3-({[(phenylsulfonyl)amino]carbonyl}amino)propyl]piperidinium bis(trifluoroacetate);

and their pharmaceutically acceptable salts.

Further preferred compounds are:

N-{1-[3-(benzenesulfonylmethylamino)-3-phenylpropyl]piperidin-4-yl}-N-phenylpropionamide;

N-{3-[4-(2-methyl-2H-pyrazol-3-yl)piperidin-1-yl]-1-phenylpropyl}benzenesulfonamide;

(R)-N-{3-[4-(2-ethyl-5-methyl-2H-pyrazol-3-yl)piperidin-1-yl]-1-phenylpropyl}-N-methylbenzenesulfonamide;

N-{1-(4-chlorophenyl)-3-[4-(2-ethyl-5-methyl-2H-pyrazol-3-yl)piperidin-1-yl]propyl}-N-methylbenzenesulfonamide;

4-bromo-N-{3-[4-(2-ethyl-5-methyl-2H-pyrazol-3-yl)piperidin-1-yl]-1-phenylpropyl}benzenesulfonamide hydrochloride;

3-bromo-N-{3-[4-(2-ethyl-5-methyl-2H-pyrazol-3-yl)piperidin-1-yl]-1-phenylpropyl}benzenesulfonamide hydrochloride;

N-{3-[4-(2-ethyl-5-methyl-2H-pyrazol-3-yl)piperidin-1-yl]-1-phenylpropyl}-4-fluorobenzenesulfonamide hydrochloride;

N-{3-[4-(2-ethyl-5-methyl-2H-pyrazol-3-yl)piperidin-1-yl]-1-phenylpropyl}-N-phenylmethanesulfonamide hydrochloride;

1-methyl-1H-imidazole-4-sulfonic acid {3-[4-(2-ethyl-5-methyl-2H-pyrazol-3-yl)-piperidin-1-yl]-1-phenylpropyl}amide;

5-bromothiophene-2-sulfonic acid {3-[4-(2-ethyl-5-methyl-2H-pyrazol-3-yl)piperidin-1-yl]-1-phenylpropyl}amide hydrochloride;

or a pharmaceutically acceptable salt thereof.

Further preferred compounds are:

N-{3-[4-(pyrimidin-3-yl)piperidin-1-yl]-1-phenylpropyl}-4-methylbenzenesulfonamide;

N-{3-[4-(pyridin-3-yl)piperidin-1-yl]-1-phenylpropyl}-4-methylbenzenesulfonamide;

N-methyl-N-{3-[4-(1,3-dimethylpyrazin-5-yl)piperidin-1-yl]-1-phenylpropyl}benzesulfonamide;

(R)-N-{3-[4-(1-ethyl-3-methylpyrazin-5-yl)piperidin-1-yl]-1-phenylpropyl}benzenesulfonamide;

(S)-N-{3-[4-(1-ethyl-3-methylpyrazin-5-yl)piperidin-1-yl]-1-phenylpropyl}benzenesulfonamide;

(S)-N-methyl-N-{3-[4-(1-ethyl-3-methylpyrazin-5-yl)piperidin-1-yl]-1-phenylpropyl}benzenesulfonamide;

N-{3-[4-(benzimidazolon-1-yl)piperidin-1-yl]-1-phenylpropyl}benzenesulfonamide;

N-[3-(4-methylcarbonyl-4-phenyl)piperidin-1-phenylpropyl]benzenesulfonamide;

(R)-N-{3-[4-(1-ethyl-3-benzylpyrazin-5-yl)piperidin-1-yl]-1-phenylpropyl}thiophen-2-ylsulfonamide;

(R)-N-{3-[4-(1-ethyl-3-methylpyrazin-5-yl)piperidin-1-yl]-1-phenylpropyl}-2-fluorophenylsulfonamide;

(R)-N-{3-[4-(1-ethyl-3-methylpyrazin-5-yl)piperidin-1-yl]-1-phenylpropyl}-3-fluorophenylsulfonamide;

(R)-N-{3-[4-(1-ethyl-3-methylpyrazin-5-yl)piperidin-1-yl]-1-phenylpropyl}-4-fluorophenylsulfonamide; and N-methyl-N-{3-[4-(1-ethyl-3-methylpyrazin-5-yl)piperidin-1-yl)-1-phenylpropyl}benzenesulfonamide;
or a pharmaceutically acceptable salt thereof.

Preferred pharmaceutical salts include trifluoroacetate and chloride salts. Both single and double salts can be formed where possible.

These compounds and those defined by the immediately preceding definitions are especially useful as NK-3 antagonists and themselves form part of the present invention.

The terms "administration of" and or "administering a" compound should be understood to mean providing a compound of the invention to the individual in need of treatment.

The term "subject," (alternatively referred to herein as "patient") as used herein refers to an animal, preferably a mammal, most preferably a human, who has been the object of treatment, observation or experiment.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethylamine, diethylamine, piperazine, tris(hydroxymethyl) aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an acid (—COOH) or alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.) The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds for use in the present invention are generally active in the following test. They normally have an $IC_{50}$ of less than 1 µM and preferably less than 100 nM.

Details of the NK-3 receptor and its heterologous expression can be found in Huang et al, BBRC, 1992, 184: 966–972 and Sadowski et al, Neuropeptides, 1993, 24: 317–319.

A membrane preparation is prepared as follows. A 10-layer cell factory is seeded with CHO cells stably expressing NK-3 receptors. The CHO cells are prepared in a triple T175 flask in 1l growth medium which contains Iscore's modified Dulbecco's medium containing 10 ml/l 200 mM L-Glutamine, 10 ml/l penicillin-streptomycin, one vial of hypoxanthine-thymidine 500×/l, 1 mg/ml geneticin and 10% fetal bovine serum (inactivated). The cells are grown for 3 days in an incubator. The medium is washed off and the factory is rinsed twice with 400 ml PBS (Ca, Mg-free). 400 ml enzyme free dissoc. solution (EFDS) is added and the factory is maintained for 10 min at room temperature. The cells are dislodged and the suspension poured into 500 ml centrifuge bottles. The process is repeated with 200 ml EFDS and the mixtures pooled giving 6 bottles in all, which are spun in a centrifuge for 10 min at 2200 rpm.

The supernatants are aspirated and the residual cell pellets are frozen at −80° for 30 min to improve cell lysis and then resuspended in 40 ml Tris with inhibitors per cell factory.

The cells are homogenized in 40 ml aliquots with 8 strokes of a glass-teflon grinder at setting 40. The homogenate is transferred to 50 ml centrifuge tubes and placed on a rocker for 15 min at r.t. The homogenate is rehomogenised and held on ice if necessary before being centrifuged again as above.

The supernatant is transferred to Sorvall tubes for an SS-34 roter and held on ice.

40 ml cold Tris with inhibitors is used to resuspend and combine the pellets which are again spun as above. The supernatants are again transferred to Sorvall tubes which, with those above, are spun at 18000 rpm for 20 min.

The supernatants are discarded and the pellets resuspended in a Storage Buffer consisting of 2.50 ml 1M Tris pH7.4, 50 µl 1000× protease inhibitors (4 mg/ml leupeptin (Sigmo), 40 mg/ml Bacitracin (Sigma) and 10 mM phosphoranidon (Peninsula) all dissolved in water) plus 0.5 ml 0.5 M $MnCl_2$ made up to 50 ml with $H_2O_{dd}$. A 10 ml syringe is used with 20-, 23- and 25-gauge needles sequentially.

A Bradford protein assay in conducted on 2–10 µl aliquots with BSA as standard before 500–1000 µl aliquots are snap-frozen in liquid nitrogen for storage at −80° C.

The membrane binding assay is carried out as follows. The amount of membranes needed to specifically bind ≦10% of $^{125}$I-NeurokinB is predetermined. The frozen stocks are then diluted to allow addition in 50 µl.

The test compounds are dissolved in DMSO. An automated apparatus (Tecan) is programmed to add 5 µl of compound or DMSO, approximately 100,000 cpm of isotope in 20 µl buffer which is prepared from 50 µMTris, pH7.5, 150 µM NaCl, bovine serum albumin to 0.02%, and protease inhibitors as in the storage buffer, made up as 0.5M stock, and 175 µl assay buffer (as the storage buffer but containing 5 µM $MnCl_2$ and without NaCl) into deep well Marsh boxes (Marsh Biomedical Products) in a 96-well format. Excess unlabelled competing peptide is added by hand for non-specific binding as indicated below. The binding reaction is initiated by adding 50 µl of cell membranes. The tubes are incubated with shaking for 1 h at r.t. and filtered on a Tomtec 96 well cell harvester using Mach III filtermats (Tomtec) or using either a Packard 96-well harvester or Tomtec 9600 using Unifilter GF/C (Packard), presoaked in 0.25% polyethyleneimine and washed five times with 1× wash buffer (0.1 M.Tris, pH7.4 and 1M NaCl, 1×=100 ml of 10× stock per litre of cold distilled water). If using Unifilter plates, 60 µl Microscint 20 (Packard) is added to each well and the plate is then heat-sealed before counting in a Packard Topcount. Alternatively the filters from the filtermat are placed in 75×100 mm plastic tubes and counted on a Cobra gamma counter.

For the assay, typically 10 µg of membrane is used at 25,000 cpm which is filtered over a Unifilter GF/C presoaked in 0.5% BSA.

Abbreviations used in the instant specification, particularly the Schemes and Examples, include the following:
Ac=acetyl
9-BBN=9-borabicyclo[3.3.1]nonane
Bn=benzyl
BOC or Boc=t-butyloxycarbonyl
Bu=butyl
t-Bu=tert-butyl
CBZ=carbobenzoxy (alternatively, benzyloxycarbonyl)
CDI=carbonyl diumidazole
DAST=(diethylamino)sulfur trifluoride
DCC=dicyclohexyl carbodiimide
DCM=dichloromethane
DIBAL=diisobutylaluminum hydride
DIEA or DIPEA=diisopropylethylamine
DIAD=diisopropylazodicarboxylate
DMF=N,N-dimethylformamide
DMSO=dimethylsulfoxide
EDAC=1-(3-dimethylamino)propyl-3-ethylcarbodiimide
Et=ethyl
ether=diethyl ether
h=hour(s)
HMDS=hexamethyldisilazyl
HOBT or HOBt=1-hydroxy benzotriazole hydrate
KHMDS=potassium hexamethyldisilazide
LDA=lithium diisopropylamide
Me=methyl
m=minute(s)
Ph=phenyl
Pr=propyl
i-Pr=isopropyl
PMB=p-methoxybenzyl
sat'd=saturated aqueous
rt=room temperature
TBSO=t-butyldimethylsiloxy
TEA=triethylamine
Tf=triflic or triflate
TFA=trifluoroacetic acid
THF=tetrahydrofuran
TPAP=tetrapropylammonium perruthenate The compounds of the present invention can be readily prepared according to the following reaction schemes and examples, or modifications thereof. Starting materials can be made from procedures known in the art or as illustrated. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, the variables are as defined above.

Compounds of formula I can be made by reacting a compound of formula II with a compound of formula III:

where $R^1$, $R^2$, $R^3$, $R^4$, Q and X are as defined above and L is a leaving group such as iodine or hydroxy. When L is iodine the reaction is generally carried out in the presence of a base such as potassium hydrogencarbonate and a solvent such as acetonitrile with heating to about 65° C. for about 8 hours. When L is hydroxy the reaction is generally carried out in a solvent such as tetrahydrofuran in the presence of coupling agents such as $PPh_3$ and DIAD at about room temperature for several hours.

The compound of formula II can be made by reacting the corresponding methylsulfonate with a compound of formula $M^+L^-$ where L is as defined above and $M^+$ is a counterion. For example the iodide can be produced by reacting with potassium iodide generally at refllux for several hours in a solvent such as acetone.

The methylsulfonate can be produced by reacting the corresponding alcohol with mesyl chloride generally in the presence of a base such as diisopropylethylamine in a solvent such as dichloromethane at about room temperature for about two hours under an inert atmosphere.

The alcohol can be made by reacting the corresponding allyl compound successively with ozone, generally in a solvent such as methanol at about −78° C. for about thirty minutes, and then a reducing agent such as sodium borohydride, generally at about room temperature for about 15 minutes.

This compound can be made by reacting a compound of formula IV with a compound of formula V:

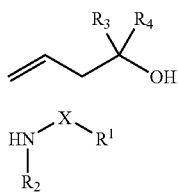

(IV)

(V)

wherein $R^1$, $R^2$, $R^3$, $R^4$ and X are as defined above in a Mitsonobu reaction. This is generally carried out in the presence of coupling agents such as diisopropylazocarboxylate and triphenylphosphine in a solvent such as tetrahydrofuran under an inert atmosphere at about room temperature for about twenty hours.

In an alternative process, compounds of formula I can be made by reacting a compound of formula VI with a compound of formula VII:

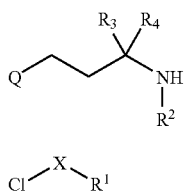

(VI)

(VII)

wherein $R^1$, $R^2$, $R^3$, $R^4$, X and Q are as defined above. The reaction is generally carried out in a solvent such as dichloromethane and in the presence of a base such as triethylamine at about room temperature for about one to three hours.

The compound of formula VI can be made by hydrolysing the corresponding carbamic acid butyl ester for example in a solvent such as dichloromethane with an acid such as trifluoroacetic acid at about room temperature for about 45 minutes.

This compound can be made by reacting the trifluoroacetate of a compound of formula HQ, where Q is as defined above, with a compound of formula VIII:

(VIII)

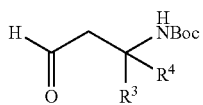

wherein $R^3$ and $R^4$ are as defined above in the presence of a reducing agent such as $NaBH(OAc)_3$ or $NaBH_3CN$, a base such as triethylamine or methanol and a solvent such as dichloroethane at about room temperature for several hours, preferably under an inert atmosphere.

A similar reaction can be used to produce compounds of formula I from a compound of formula HQ and a compound of formula IX:

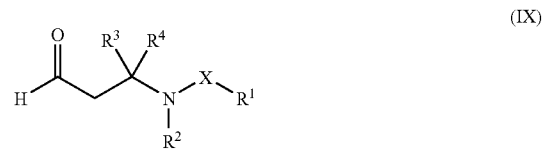

(IX)

where $R^1$, $R^2$, $R^3$, $R^4$ and X are as defined above. The compound of formula IX can be made from the corresponding allyl compound by reacting, successively with ozone in a solvent such as dichloromethane at about −78° C. for about one hour and then oxygen in the presence of dimethylsulfide at about room temperature for about three days.

This compound can be made by reacting an alkylating agent, such as alkyl magnesium bromide, with a compound of formula X:

(X)

wherein $R^1$, $R^3$ and X are as defined above in a solvent such as tetrahydrofuran under an inert atmosphere for about two hours.

The compound of formula VI can also be made by reacting the corresponding azide with hydrogen using a catalyst such as platinum oxide in a solvent such as ethanol for about four hours.

This azide can be made by reacting the corresponding alcohol with a reactant such as sodium azide in a solvent such as dimethylformamide at a temperature of about 50° C. for about three hours. The alcohol is preferably first converted into a more labile leaving group such as a tosylate group by reacting the alcohol with tosyl chloride in a solvent such as dichloromethane in the presence of a base such as triethylamine at about room temperature for about three hours.

The alcohol can be produced by selectively reducing the corresponding ketone using, for example, sodium borohydride at about room temperature for about fifteen minutes.

This ketone can be made by reacting a compound of formula HQ, for example as the trifluoroacetate salt, with a compound of formula XI:

(XI)

wherein $R^3$ is as defined above with a source of formaldehyde such as paraformaldehyde in a Mannich reaction, generally in a solvent such as ethanol and in the presence of an acid such as hydrochloric acid at about reflux for about four hours.

SCHEME 3

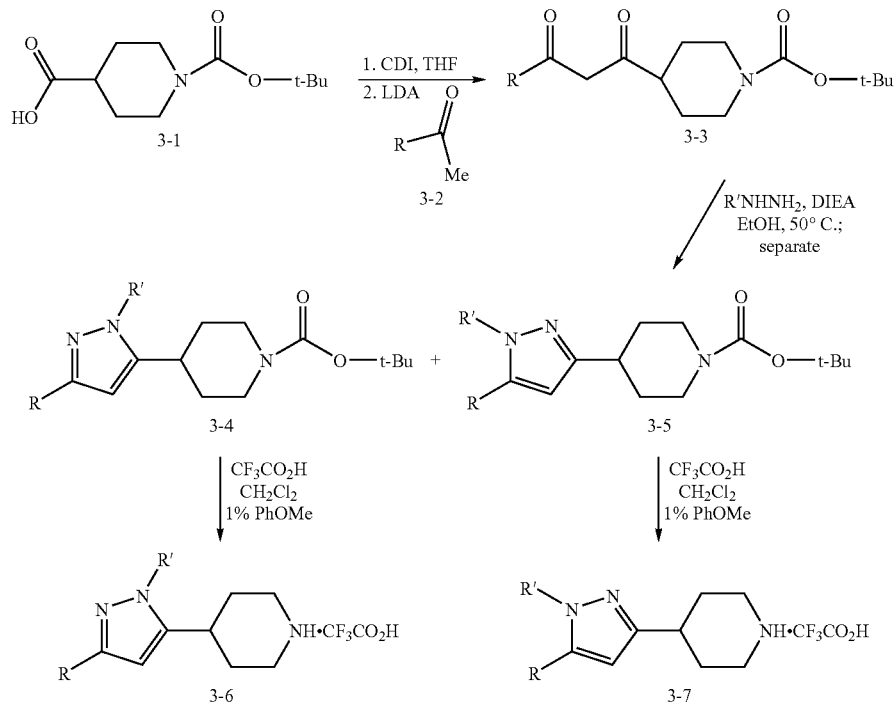

One preparation of piperidine subunits containing functionalized pyrazoles at C4 of the piperidine is given in Scheme 3. Treatment of piperidine 3-1 with carbonyldiimidazole to form the acyl imidazole, followed by enolate formation by addition of addition of lithium diisopropylamide (LDA), and then a dialkyl or alkyl-aryl ketone 3-2 gives the diketone 3-3. Treatment with a monoalkyhydrazine in an alcohol solvent at temperatures between 0 to 100 degrees C. (preferably about 50 degrees C.) optionally in the presence of a hindered base such as DIEA then provides a mixture of the isomeric pyrazoles 3-4 and 3-5. After separation of these compounds by chromatography or crystallization, the individual products are deblocked under acidic conditions (for example trifluoroacetic acid and anisole with or without methylene chloride as a cosolvent) to provide the piperidine salts 3-6 and 3-7.

SCHEME 4

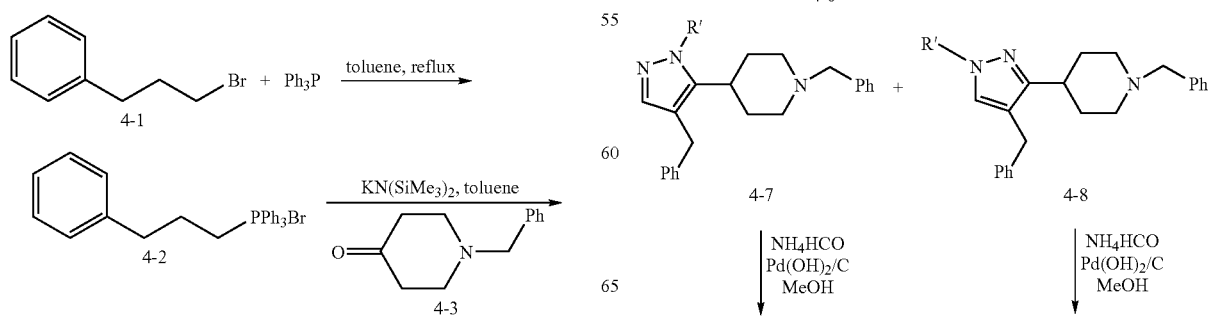

-continued

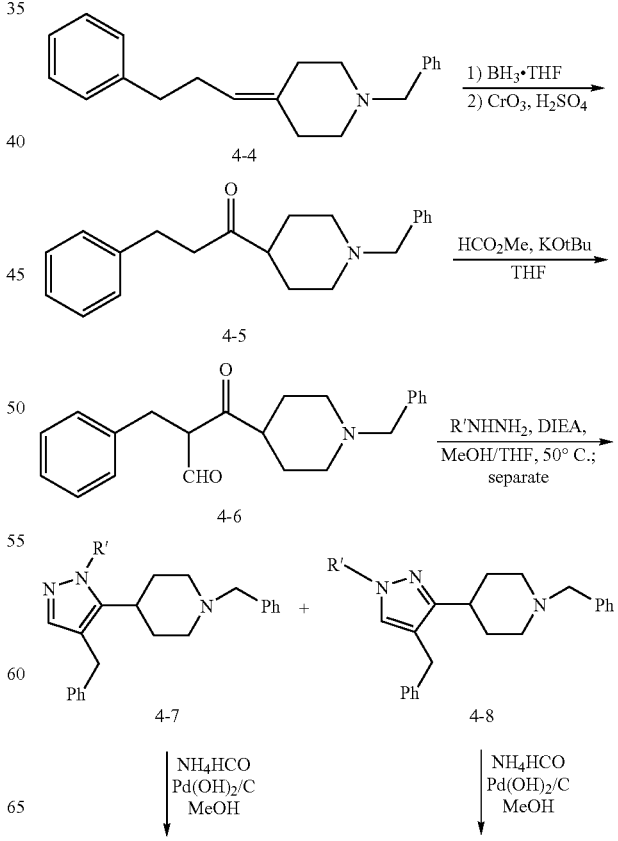

-continued

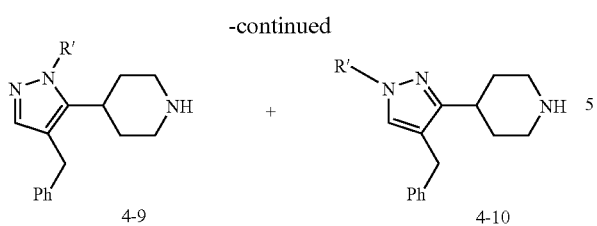

Another preparation of piperidine subunits containing functionalized pyrazoles at C4 of the piperidine is given in Scheme 4. Treatment of commercially available bromide 4-1 with triphenylphosphine in refluxing toluene provides phosphonium salt 4-2, which after treatment with a strong anhydrous base such as potassium hexamethyldisilazide in toluene and the piperidine ketone 4-3 provides the olefin 4-4. Hydroboration followed by an oxidative workup with chromic acid then affords ketone 4-5. Selective formylation of 4-5 with methyl formate in the presence of potassium t-butoxide affords ketoaldehyde 4-6. Heating of 4-6 with a monoalkylhydrazine in methanol optionally in the presence of a hindered (or insoluble) base such as DIEA then provides a mixture of the 1,5-disubstituted pyrazoles 4-7 and 4-8. After separation by chromatography, crystallization or fractional distillation, the purified isomers are deprotected under transfer hydrogenation conditions to provide the piperidines 4-9 and 4-10.

An alternate preparation of piperidine subunits containing functionalized pyrazoles at C4 of the piperidine is given in Scheme 5. Treatment of commercially available isonipecotic acid under reducing conditions with borane-THF complex provides primary alcohol 5-2. Oxidation under standard conditions, for example using Swern's conditions, yields aldehyde 5-3. Treatment of 5-3 with carbon tetrabromide in the presence of triphenylphosphine affords dibromo-olefin 5-4, which upon treatment with n-butyllithium followed by tributyl tin chloride provides stannyl acetylene 5-5. Coupling of 5-5 with an acid chloride ArCH₂COCl in the presence of a suitable palladium catalyst, such as dichlorobis (triphenylphosphine)palladium, in refluxing dichloromethane provided unsaturated ketone 5-6. Treatment of acetylenic ketone 5-6 with a mono-alkylhydrazine in a suitable solvent, such as ethanol, affords pyrazole 5-7. Deprotection of this compound under acidic conditions, for example with HCl in methanol or with trifluoroacetic acid in dichloromethane in the presence of anisole, provides the desired pyrazole derivative 5-8.

SCHEME 5

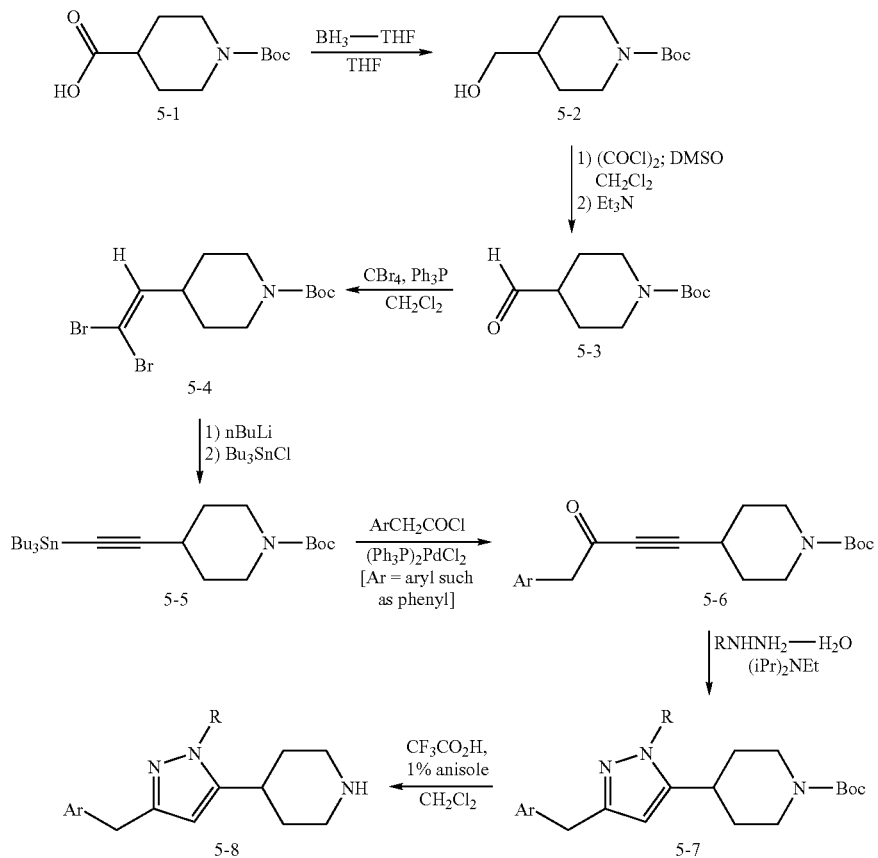

SCHEME 6

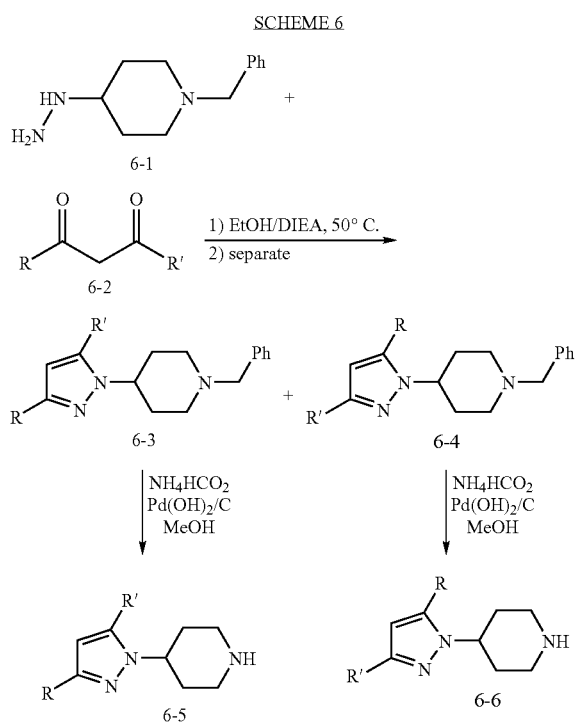

A preparation of piperidine subunits containing 3,5-difunctionalized pyrazoles linked through N1 to C4 of the piperidine is given in Scheme 6. Treatment of commercially available hydrazine 6-1 with diketone 6-2 in ethanol at 0 to 90 degrees C. (prefereably 50 degrees C.) in the presence of DIEA provides a mixture of pyrazoles 6-3 and 6-4, which are separated under standard conditions, for example HPLC. Removal of the benzyl groups by transfer hydrogenation provides the secondary piperidines 6-5 and 6-6.

SCHEME 7

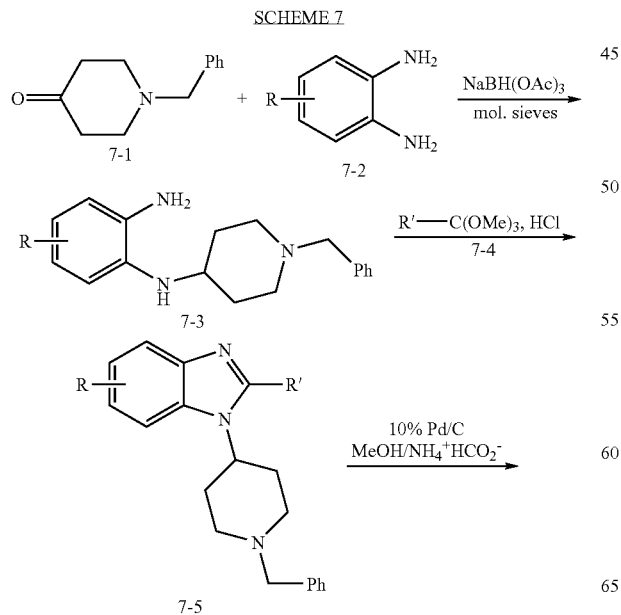

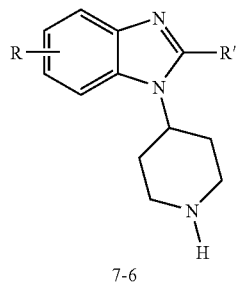

A preparation of 4-(benzimidazol-1-yl)piperidine subunits is given in Scheme 7. Combining piperidone 7-1 and diamine 7-2 in the presence of sodium triacetoxy borohydride under dehydrating conditions provides reductive amination product 7-3. Addition of a suitably substituted ortho ester 7-4 in the presence of a acid catalyst, for example concentrated hydrochloric acid, provides benzimidazole intermediate 7-5. Deprotection under reductive conditions, for example with palladium on carbon under transfer hydrogenation conditions, then provides secondary amine 7-6.

SCHEME 8

-continued

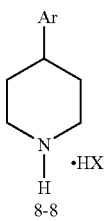
8-8

One method of generating 4-aryl piperidines as intermediates is given in Scheme 8. Reaction of commercially available 8-1 or 8-2 with a strong base, such as LDA, LiHDMS, NaHMDS, KHMDS, or NaH followed by treating with a suitable triflating agent, such as 5-chloropyrid-2-yl triflimide (8-3), N-phenyl triflimide or triflic anhydride, provides enol triflates 8-4 or 8-5. Heating with commercially available aryl boronic acids in the presence of a suitable palladium(0) catalyst such as tetrakis triphenylphosphine palladium, a base (such as potasssium carbonate or sodium carbonate), in a solvent such as DME, THF, dioxane or toluene/ethanol, effects coupling to provide the unsaturated products 8-6 or 8-7. In the case of 8-7, treatment with a heterogeneous palladium catalyst in methanol or ethanol in an atmosphere of hydrogen provides the desired intermediate 8-8. Alternatively, the Boc protected derivative 8-6 is hydrogenated under standard conditions to provided the saturated piperidine 8-9, which is then deprotected under acidic conditions (such as trifluoroacetic acid and anisole in methylene chloride), to provide 8-8 as a salt.

SCHEME 9

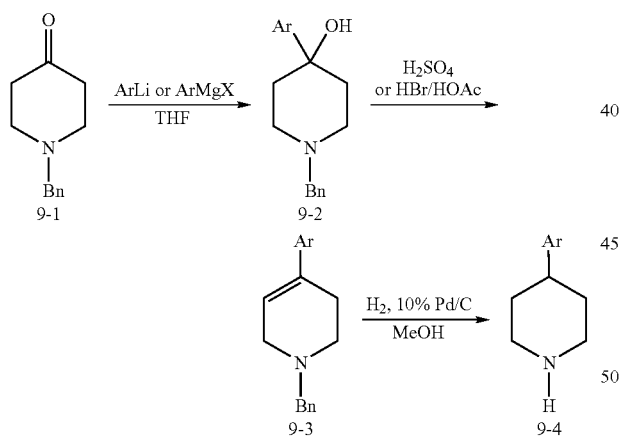

An alternative method of generating 4-aryl piperidines as intermediates is given in Scheme 9. Reaction of commercially available 9-1 with an aryl magnesium halide or with an aryllithium (in the presence or absence of anhydrous cerium trichloride) provides tertiary alcohol 9-2, which upon treatment under acidic conditions (such as sulfuric acid, HBr in acetic acid, HCl in acetic acid) or under dehydrating conditions (such as with thionyl chloride in pyridine or with phosphorus oxychloride) provides olefin 9-3. Hydrogenation under standard conditions using either hydrogen gas or a hydrogen donor (such as ammonium formate or cyclohexene) effects reduction of the double bond and cleavage of the N-benzyl group to provide the desired intermediate 9-4. Under some circumstances it may be preferable to reduce the double bond under non-hydrogenolytic conditions, for example with triethylsilane and trifluoroacetic acid or under dissolving metal conditions (for example, sodium or lithium metal in ammonia or a lower alkyl amine). If the N-benzyl group is not removed under these conditions, it may be cleaved by treatment with either vinyl chloroformate and then hydrogen chloride or by treatment with 2-chloroethyl chloroformate followed by heating in methanol.

SCHEME 10

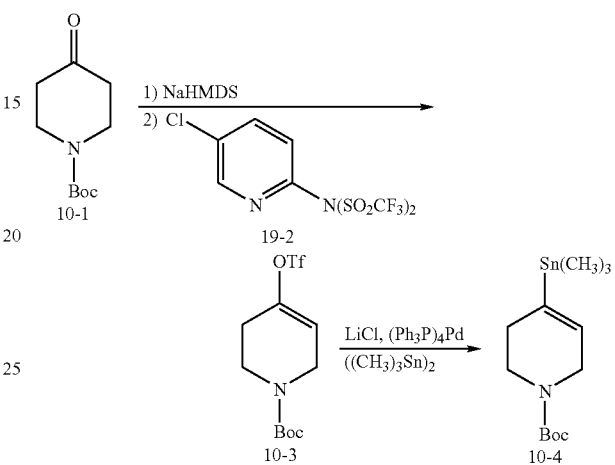

Piperidine intermediates bearing a pyridine substituent can be synthesized as shown in Scheme 10. Enolization of ketone 10-1 with a strong, non-nucleophilic base such as sodium hexamethyldisilazide, followed by treatment with a suitable triflating agent, such as 2-(N,N-bis(trifluoromethanesulfonyl)amino)-5-chloropyridine (10-2), provides vinyl triflate 10-3. Exchange of the triflate for a trimethylstannyl group is carried out under standard conditions to provide 10-4. Separately, treatment of benzyl magnesium chloride with zinc chloride, followed by treatment of the resulting material with 3,5-dibromopyridine, copper iodide and a suitable palladium catalyst, provides coupled product 10-7. Coupling of 10-4 with 10-7 in the presence of a soluble palladium catalyst, followed by hydrogenation of the double bond, and then cleavage of the Boc group under acidic conditions, then gives intermediate 10-8.

SCHEME 11

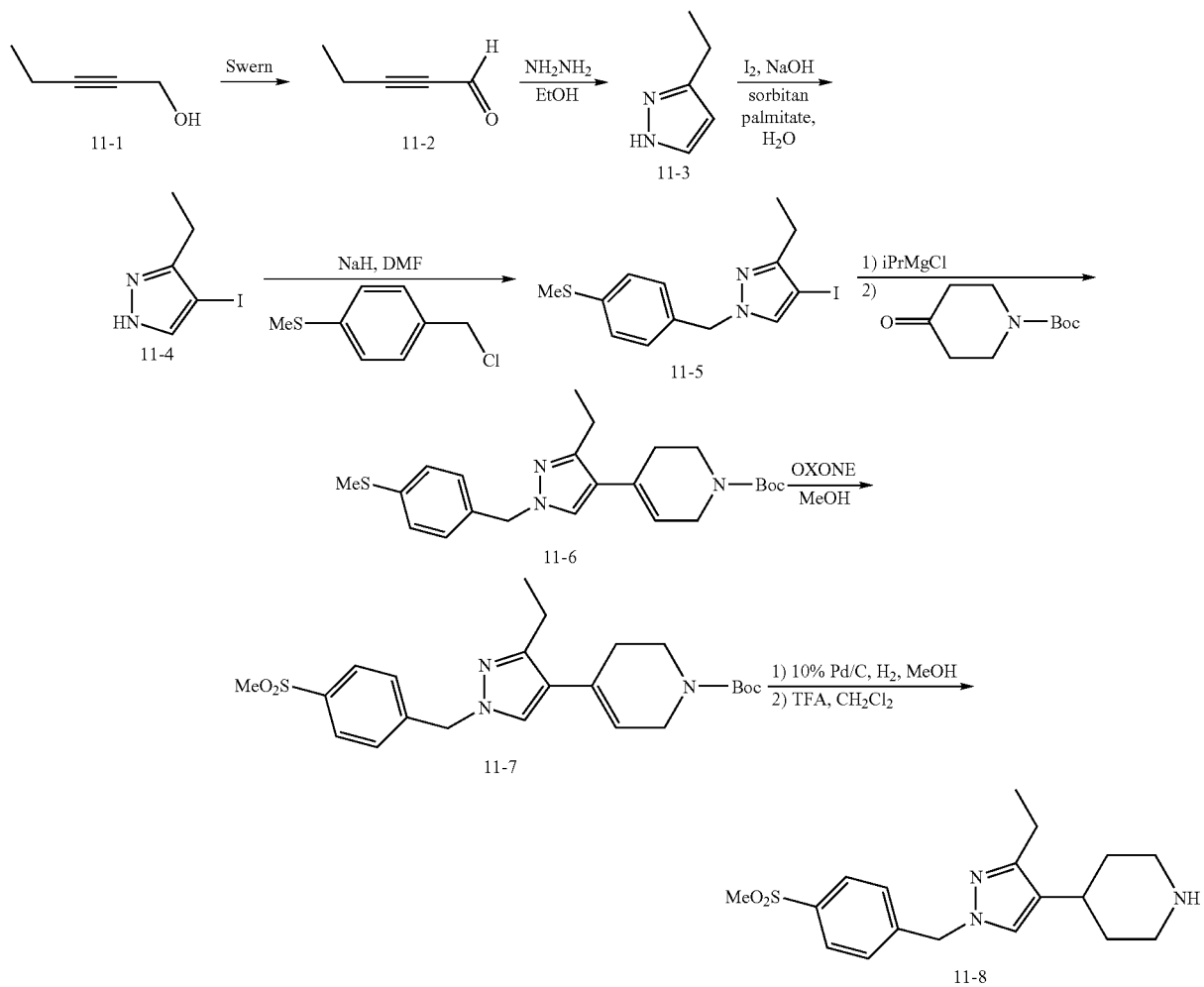

Piperidine intermediates bearing a functionalized pyrazole side chain can be prepared as shown in Scheme 11. Oxidation of 2-pentyn-1-ol under Swern conditions followed by treatment with hydrazine provides pyrazole 11-3. Iodination under phase transfer conditions affords iodopyrazole 11-4. Alkylation with 4-thiomethylbenzyl chloride yields pyrazole 11-5. Halogen-metal exchange with isopropyl magnesium chloride followed by addition of N-Boc-4-pyridone affords pyrazole 11-6, which on oxidation with Oxone® (potassium peroxymonosulfate) provides sulfone 11-7. Hydrogenation and then treatment with trifluoroacetic acid in methylene chloride then affords intermediate piperidine 11-8.

SCHEME 12

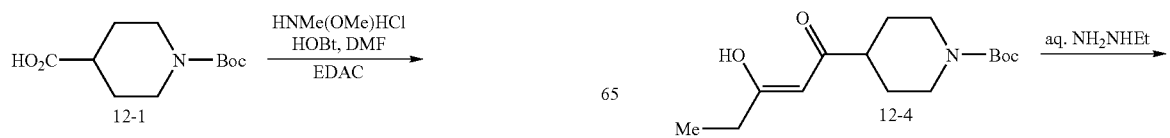

-continued

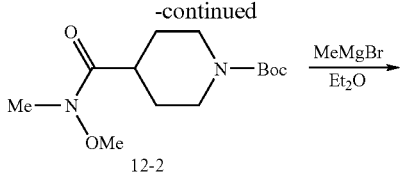

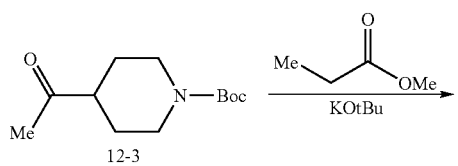

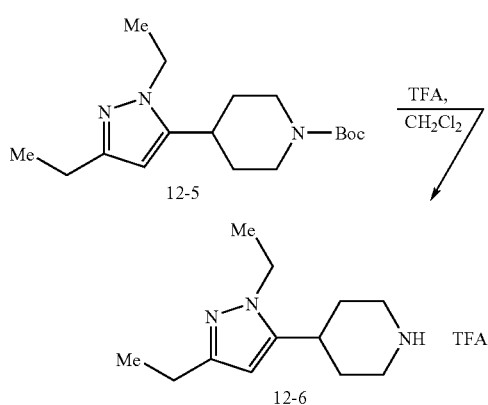

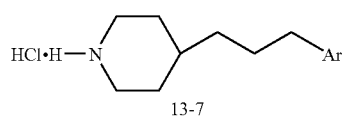

Piperidine intermediates with alkylpyrazole substituents can be prepared as shown in Scheme 12. Treatment of N-Boc-4-carboxypiperidine with EDAC, HOBt and N,O-dimethylhydroxylamine hydrochloride affords amide 12-2, which upon exposure to methyl magnesium bromide provides ketone 12-3. Condensation of 12-3 with methyl propionate in the presence of potassium tert-butoxide provides diketone 12-4, which affords pyrazole 12-5 after treatment with aqueous ethylhydrazine. Deprotection under acidic conditions, for example with trifluoroacetic acid in methylene chloride, then provides intermediate 12-6.

A route for the preparation of 4-(3-arylpropyl)piperidines is given in Scheme 22. Treatment of phosphonoacetate 13-1 with KHMDS followed by addition of commercially available N-Boc-4-piperidone 13-2 provides unsaturated ester 13-3. Hydrogenation of 13-3 followed by hydrolysis to the acid and then reduction with borane.methyl sulfide then affords primary alcohol 13-4. Mild oxidation of 13-4 under Swern conditions provides the corresponding aldehyde, which upon treatment with the Wittig reagent prepared from methyltriphenylphosphonium iodide and KHMDS yields olefin 13-5. Hydroboration with a dialkylborane, such as 9-borabicyclo[3.3.1]nonane (9-BBN), followed by treatment with an aryl halide (the halides preferably being bromide or iodide) or aryl triflate in the presence of a suitable soluble palladium catalyst, for example Pd(dppf)Cl₂, in warm to refluxing THF, provides the 3-arylpropyl derivative 14-6. Removal of the Boc group under acidic conditions, for example with HCl in methanol or with trifluoroacetic acid in methylene chloride, then affords the 1-unsubstituted piperidine 13-7.

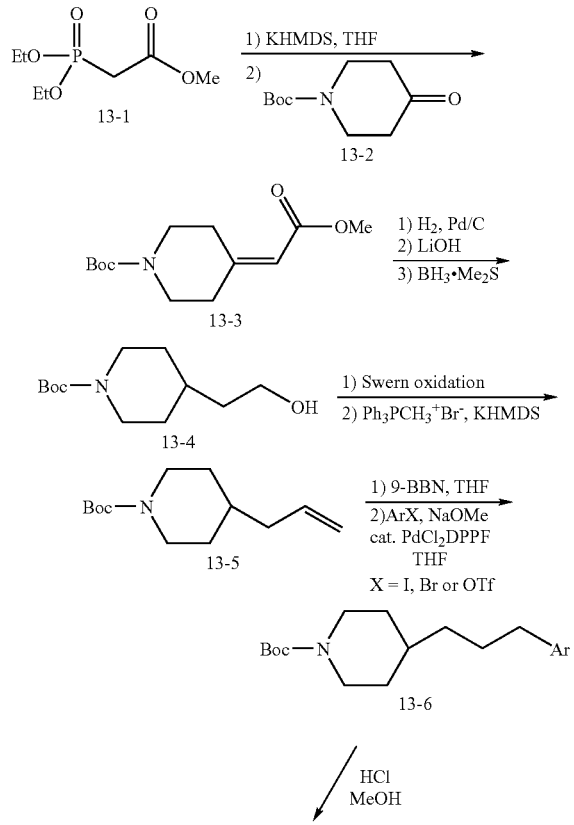

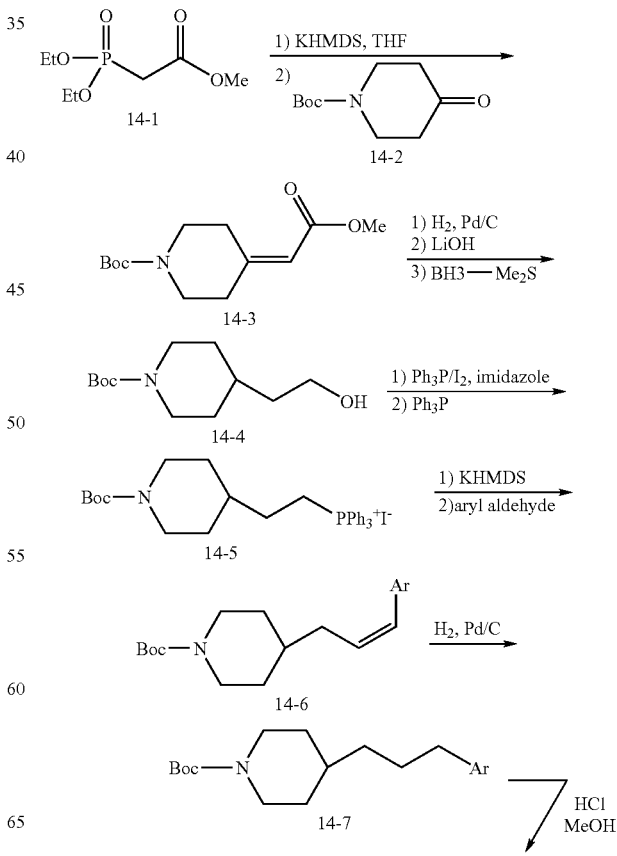

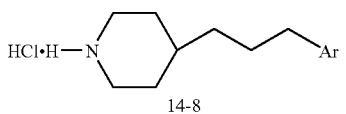

14-8

Another route for the preparation of 4-(3-arylpropyl) piperidines is given in Scheme 14. Treatment of phosphonoacetate 14-1 with KHMDS followed by addition of commercially available N-Boc-4-piperidone 14-2 provides unsaturated ester 14-3. Hydrogenation of 14-3 followed by hydrolysis to the acid and then reduction with borane-methyl sulfide then affords primary alcohol 14-4. Formation of the alkyl iodide with triphenylphosphine and iodine in the presence of imidazole followed by treatment with triphenylphosphine provides phosphonium salt 14-5. Deprotonation with a suitable base, for example, KHMDS, LiHMDS, NaHMDS, NaH, LDA, or KH affords the Wittig agent in situ, which upon treatment with a suitable aromatic aldehyde yields the unsaturated derivative 14-6. Hydrogenation under standard conditions provides 14-7, and removal of the Boc group with HCl in methanol or with other acidic conditions then provides the 1-unsubstituted piperidine 14-8.

SCHEME 15

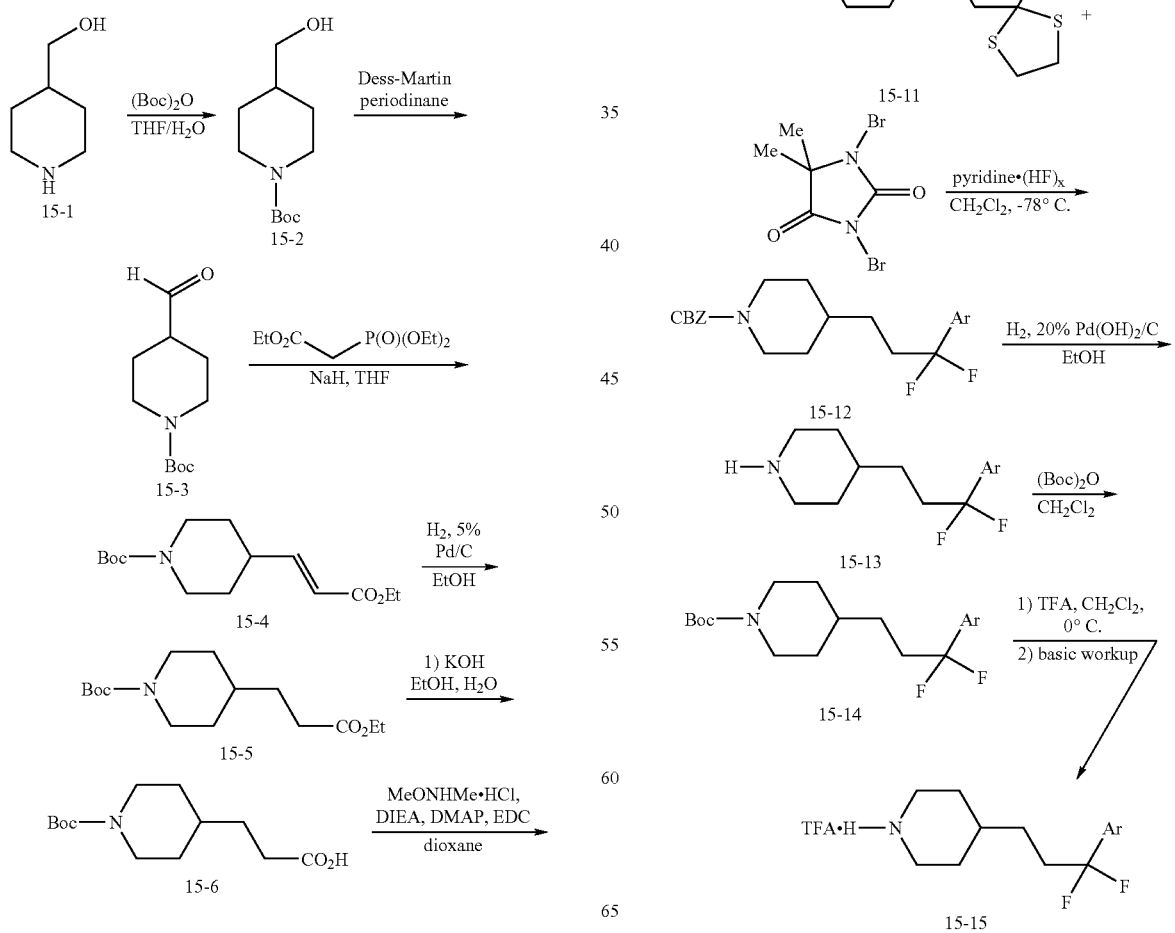

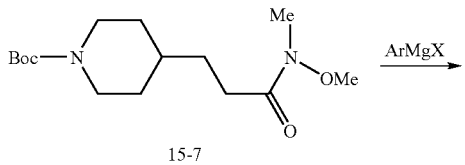

Preparation of piperidines with a 4-(3-aryl-3,3,-difluoropropyl) side chain is given in Scheme 15. Treatment of commercially available 15-1 with Boc anydride provides protected piperidine 15-2. Oxidation, for example with the Dess-Martin reagent, by a Swern oxidation, or other known methods provides aldehyde 15-3. Condensation under Horner-Wadsworth-Emmons conditions affords unsaturated ester 15-4, which is hydrogenated to ester 15-5 and then hydrolyzed to acid 15-6. Formation of the N-methyl-N-methoxy amide 15-7 is carried out employing standard activating agents such as EDC. Weinreb amide 15-7 is then allowed to react with an arylmetal reagent, such as an aryl magnesium halide or an aryllithium, to provide ketone 15-8. Cleavage of the protecting Boc group under acidic conditions yields 15-9, which is reprotected with a carbobenzyloxy group under standard conditions, to afford 15-10. Formation of dithiolane 15-11 with ethanedithiol and boron trifluoride is followed by treatment with 1,3-dibromo-3,3-dimethylhydantoin and pyridine-hydrogen fluoride complex at or around –78 degrees C., to provide gem-difluoro derivative 15-12. Removal of the CBZ group under reductive conditions provides piperidine 15-13, which may be employed directly as the secondary amine in chemistry described above. Alternatively, if additional purification is desired, 15-13 may be protected with a Boc group to afford 15-14. After suitable purification, the Boc group is removed under acidic conditions at or near 0 degrees C. A controlled, basic workup then provides 15-15.

SCHEME 16

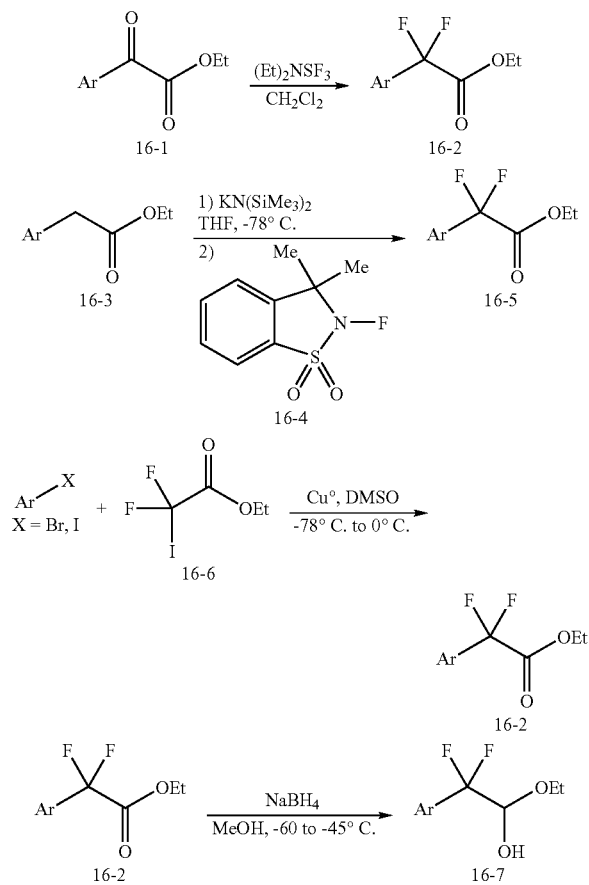

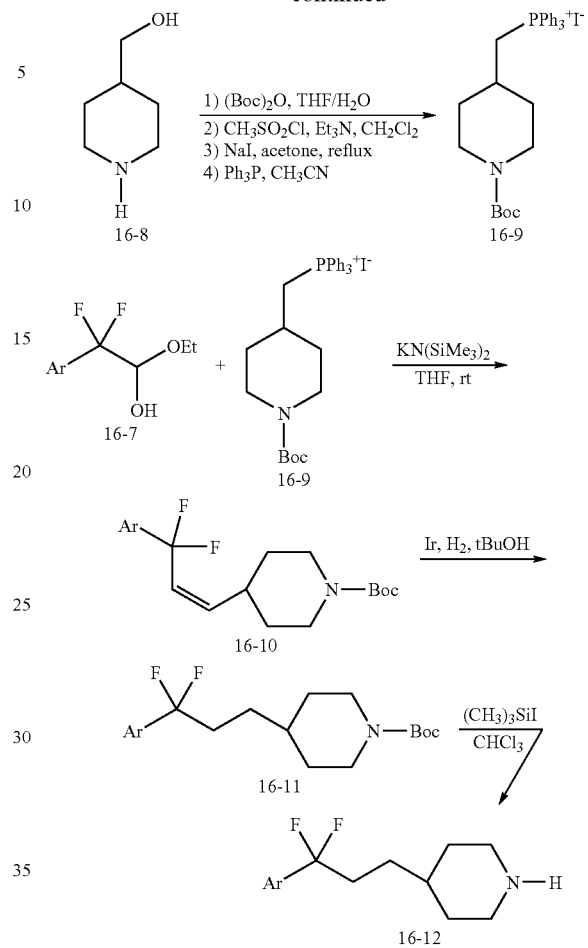

An alternate preparation of piperidines with a 4-(3-aryl-3,3,-difluoropropyl) side chain is given in Scheme 16. Preparation of the intermediate 16-2 can be accomplished in three ways. First, ketoester 16-1 can be fluorinated with diethylaminosulfur trifluoride (DAST) under standard conditions to provide α,α-difluoroester 16-2. Second, arylacetic ester 16-3 can be fluorinated by treatment with a strong base, such as potassium hexamethyldisilazide, followed by addition of a suitable fluorinating agent, such as the N-fluoro reagent 16-4, to give 16-2. Alternatively, an aryl iodide or aryl bromide 16-5 can be treated with ethyl α,α-difluoro-α-iodoacetate (16-6) in the presence of copper metal to provide 16-2. Treatment of ester 16-2 with sodium borohydride at low temperature then provides key intermediate 16-7. Preparation of intermediate 16-9 is carried out by first protecting commercially available 4-(hydroxymethyl)piperidine as the N-Boc derivative, then forming the methanesulfonyl ester under standard conditions, displacing the mesylate group with an iodide, and finally treating the iodide with triphenylphosphine. Coupling of 16-7 with phosphonium salt 16-9 in the presence of a strong base, such as potassium hexamethyldisilazide, sodium hydride, lithium diusopropylamide, or similar reagents, affords olefin 17-10. Reduction of the double bond of 16-10 is effected by treatment with iridium metal in t-butanol or hexane under an atmosphere of hydrogen, to give 16-11. Alternatively, reduction using palladium on carbon, platinum or Raney nickel in the presence of hydrogen can be used, as can diumide, which can be generated from azodicarboxylic acid in situ. The nitrogen protecting group is removed by treatment with trimethylsilyl iodide under anhydrous conditions, to afford piperidine 16-12. Alternatively, the Boc group can be removed under acidic, anhydrous conditions, for example with TFA in methylene chloride or with HCl in methanol.

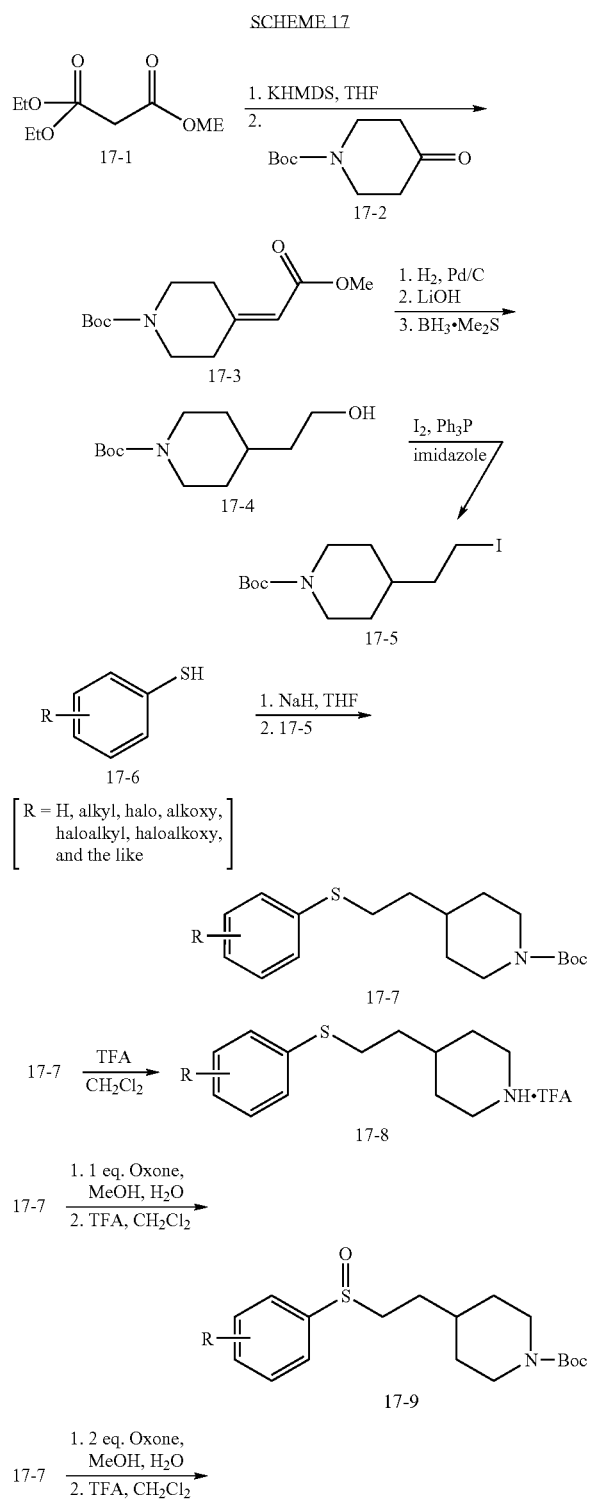

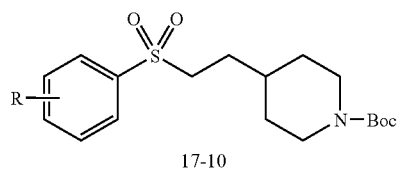

Procedures for synthesizing the present compounds containing 4-(2-(arylthio)ethyl)piperidine functionality are shown in Scheme 17. Treatment of phosphonoacetate 17-1 with KHMDS followed by addition of commercially available N-Boc-4-piperidone 17-2 provides unsaturated ester 17-3. Hydrogenation of 17-3 followed by hydrolysis to the acid and then reduction with borane.methyl sulfide then affords primary alcohol 17-4. Treatment with iodine and triphenylphosphine under standard conditions yields iodide 17-5. Reaction of the anion of a suitable aryl sulfide 17-6 with iodide 17-5 affords 4-(2-(arylthio)ethyl)-piperidine derivative 17-7. Sulfide can be deprotected directly under acidic conditions to give piperidine 17-8. Alternatively, the sulfur may be oxidized with one or two equivalents of a mild oxidizing agent such as Oxone® or mCPBA (m-chloroperoxybenzoic acid) to provide the corresponding sulfoxide or sulfone, respectively. In each case, the Boc group can be removed to provide sulfoxide 17-9 and sulfone 17-10.

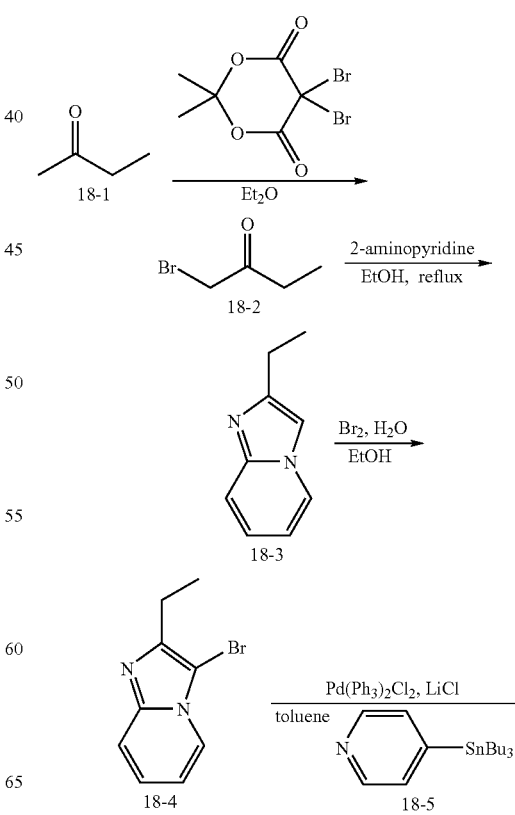

-continued

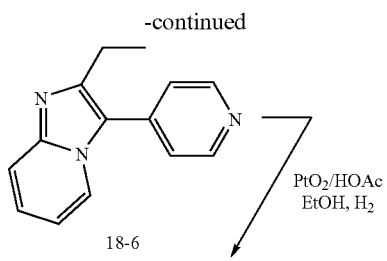
18-6

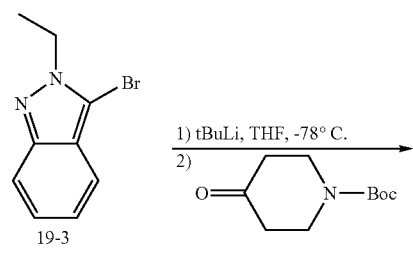
18-7

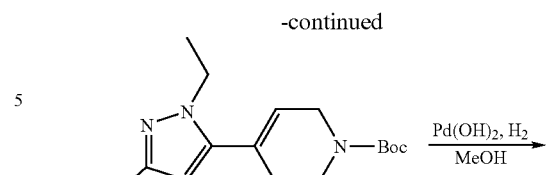
19-5

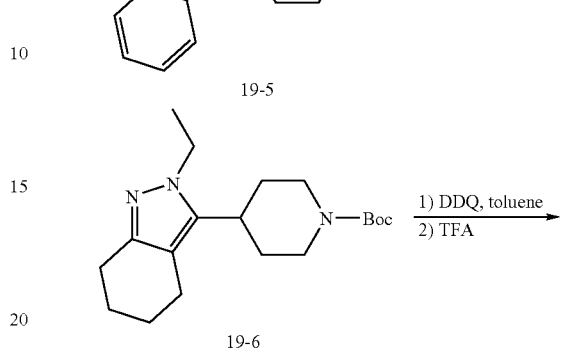
19-6

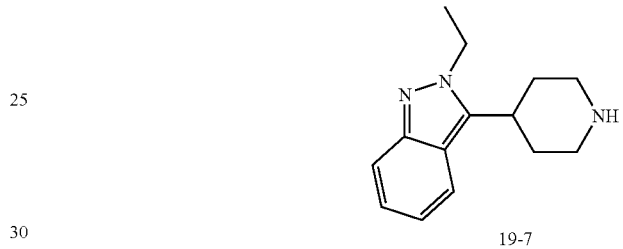
19-7

One synthesis of a secondary amine intermediate is given in Scheme 18. Bromination of 2-butanone, followed by condensation with 2-aminopyridine, affords imazopyridine 18-3. Bromination and then palladium-catalysed coupling with the pyridyl stannane 18-5 provides pyridine derivative 18-6, which upon hydrogenation under acidic conditions yield intermediate 18-7.

SCHEME 19

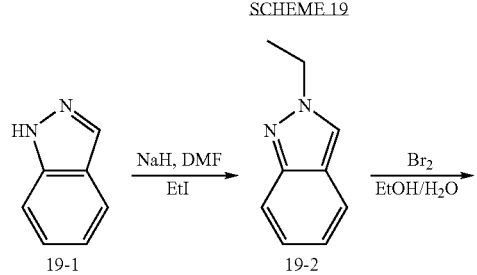

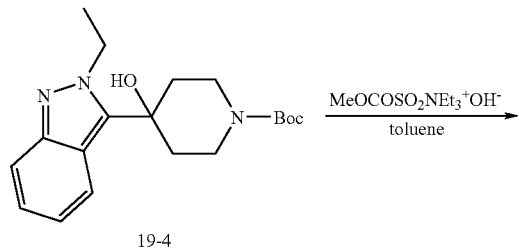
19-4

A synthesis of a secondary amine intermediate bearing an indazole substituent is given is Scheme 19. Alkylation of indazole with sodium hydride and then ethyl iodide affords the 2 alkylindazole derivative 19-2. Bromination under standard conditions provides bromide 19-3. Halogen-metal exchange, followed by trapping with the indicated pyridone derivative affords adduct 19-4, which can be dehydrated to yield 19-5. Hydrogenation produces 19-6, which can itself be employed as a secondary amine intermediate. Alternatively, it can be oxidized with DDQ and then treated with TFA to provide intermediate 19-7 as its TFA salt.

SCHEME 20

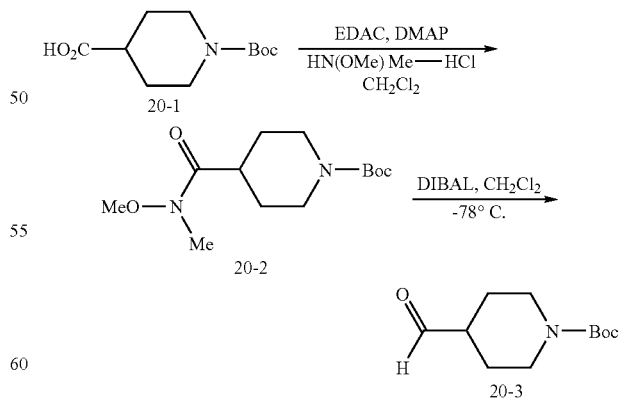

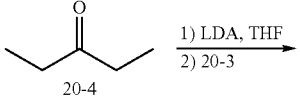
20-4

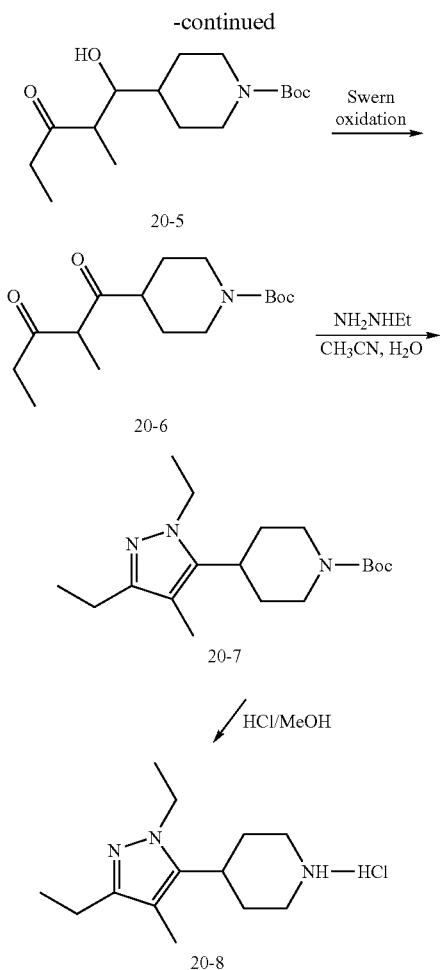
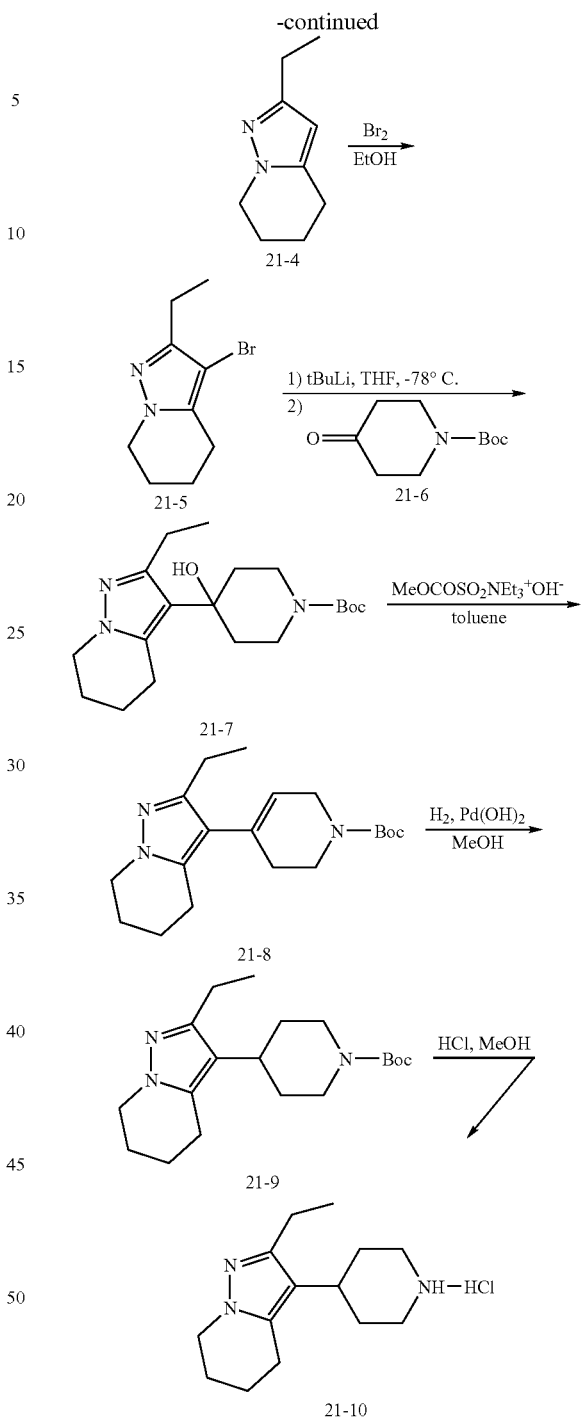

One synthesis of a secondary amine bearing a monocyclic pyrazole substituent is given in Scheme 20. Conversion of the Weinreb amide of Boc-protected isonipecotic acid to the aldehyde can be accomplished by treatment with DIBAL at low temperature in methylene chloride, to give aldehyde 20-3. Separately, formation of the lithium enolate of 2-butanone, followed by addition of 20-3, affords aldol 20-5. Oxidation to the diketone followed by treatment with ethylhydrazine in acetonitrile/water affords the pyrazole 20-7. Deprotection under acidic conditions then provides intermediate 20-8. Other substituents on the pyrazole nitrogen can be synthesized by utilizing other mono-substituted hydrazines in the condensation step with 20-6.

SCHEME 21

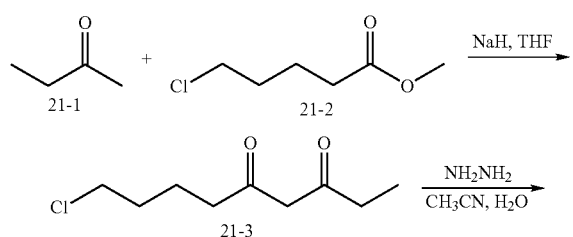

One synthesis of a secondary amine bearing a bicyclic pyrazole-based substituent is given in Scheme 21. Condensation of 2-butanone and methyl 5-chlorovalerate in the presence of sodium hydride in THF affords diketone 21-3. Treatment of this compound with hydrazine in acetonitrile/water provides pyrazolopiperidine 21-4, which upon exposure to bromine in ethanol yields bromide 21-5. Halogen-metal exchange of 21-5, followed by addition of ketone 21-6, affords 21-7. Dehydration in toluene and then hydrogenation under standard conditions provides piperidine 21-9, which can then be deprotected under acidic conditions, for example HCl in methanol, to afford desired secondary amine 21-10.

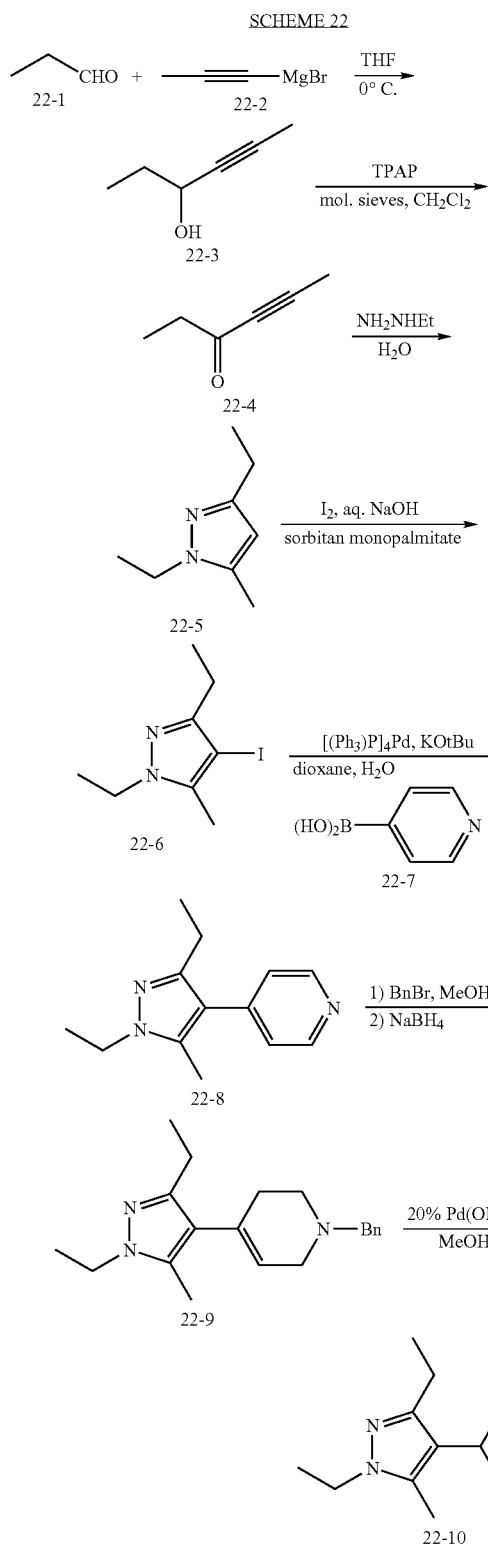

of anion 22-2 to propionaldehyde affords alcohol 22-3, which can be oxidized to ketone 22-4. Treatment with ethylhydrazine yields pyrazole 22-5, which can be iodinated under phase-transfer conditions to provide iodide 22-6. Coupling of this aldehyde with 4-pyridineboronic acid in the presence of a suitable palladium catalyst affords 22-8. Alkylation of 22-8 with benzyl bromide, followed by reduction with sodium borohydride, yields tetrahydropyridine 22-9. Catalytic hydrogenation then provides secondary intermediate 22-10. The pyrazole nitrogen substituent can be varied by utilizing alternative mono-substituted hydrazine derivatives in the condensation with 22-4.

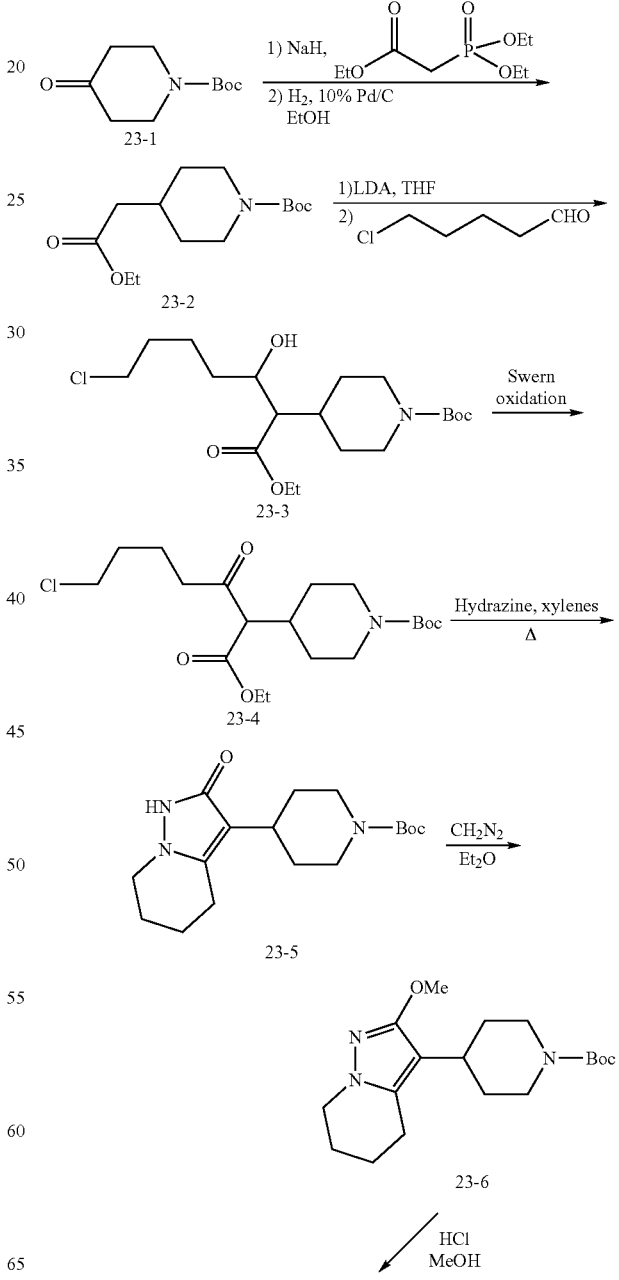

Another synthesis of a secondary amine bearing a monocyclic pyrazole substituent is given in Scheme 22. Addition

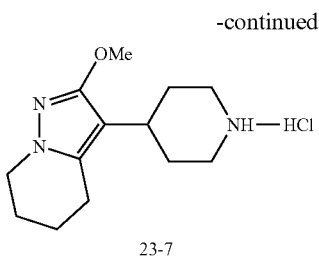

23-7

Another synthesis of a secondary amine bearing a bicyclic pyrazole-based substituent is given in Scheme 23. Condensation of N-Boc piperidone (23-1) with the anion of triethyl phosphonoacetate, followed by catalytic hydrogenation, provides piperidine 23-2. Formation of the enolate of 23-2 with a strong, non-nucleophilic base, such as LDA, followed by addition of 5-chlorovaleraldehyde, yields alcohol 23-3. Following Swern oxidation to diketone 23-4, refluxing with hydrazine in xylenes affords bicycle 23-5. Exposure of 23-5 to diazomethane in ether provides methoxy derivative 23-6, which upon deprotection under acidic conditions then affords the desired secondary amine 23-7.

SCHEME 24

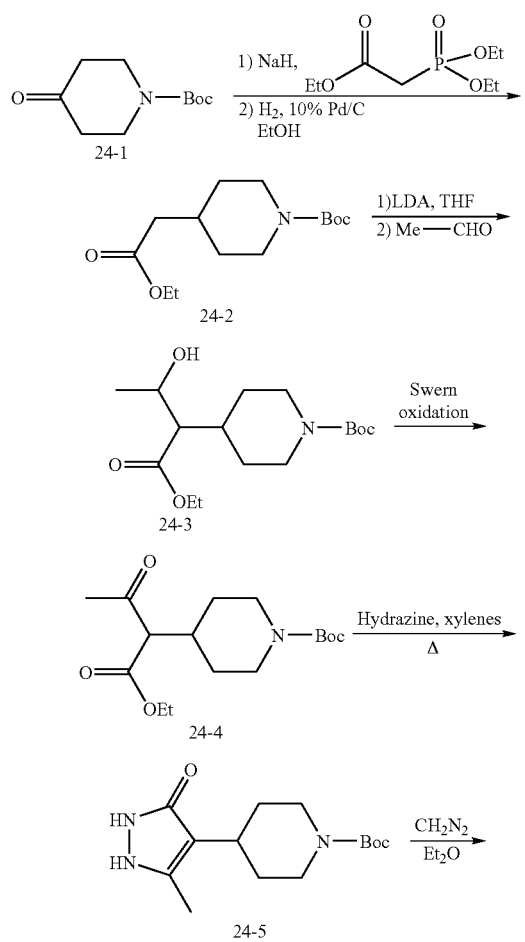

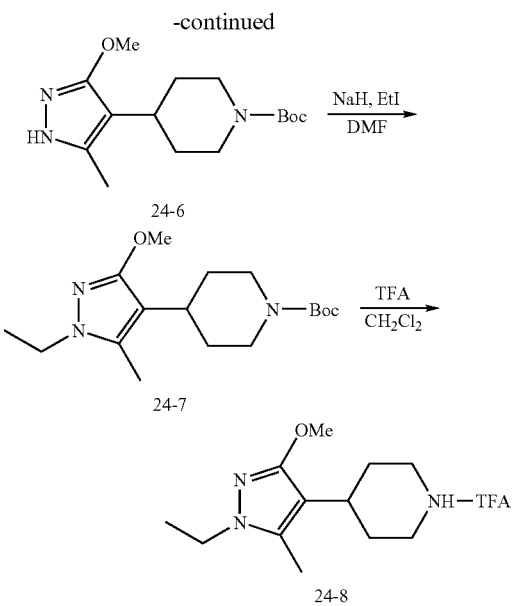

Another synthesis of a secondary amine bearing a monocyclic pyrazole substituent is given in Scheme 24. Condensation of N-Boc piperidone (24-1) with the anion of triethyl phosphonoacetate, followed by catalytic hydrogenation, provides piperidine 24-2. Formation of the enolate of 24-2 with a strong, non-nucleophilic base, such as LDA, followed by addition of acetaldehyde, yields alcohol 24-3. Following Swern oxidation to diketone 24-4, refluxing with hydrazine in xylenes affords pyrazolone 24-5. Exposure of 24-5 to diazomethane in ether provides methoxy derivative 24-6. Alkylation of pyrazole 24-6 by treating with sodium hydride and then ethyl iodide affords fully-substituted pyrazole 24-7. Alternatively, other alkylating agents can be employed in place of ethyl iodide to provide differently substituted pyrazoles. Deprotection with trifluoroacetic acid in methylene chloride then provides secondary amine 24-8.

SCHEME 25

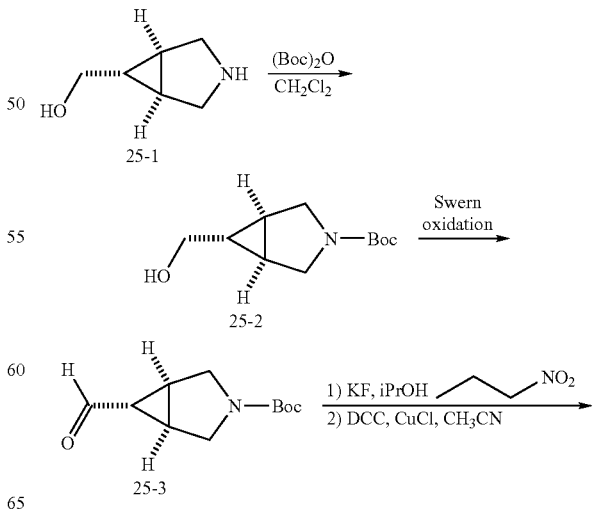

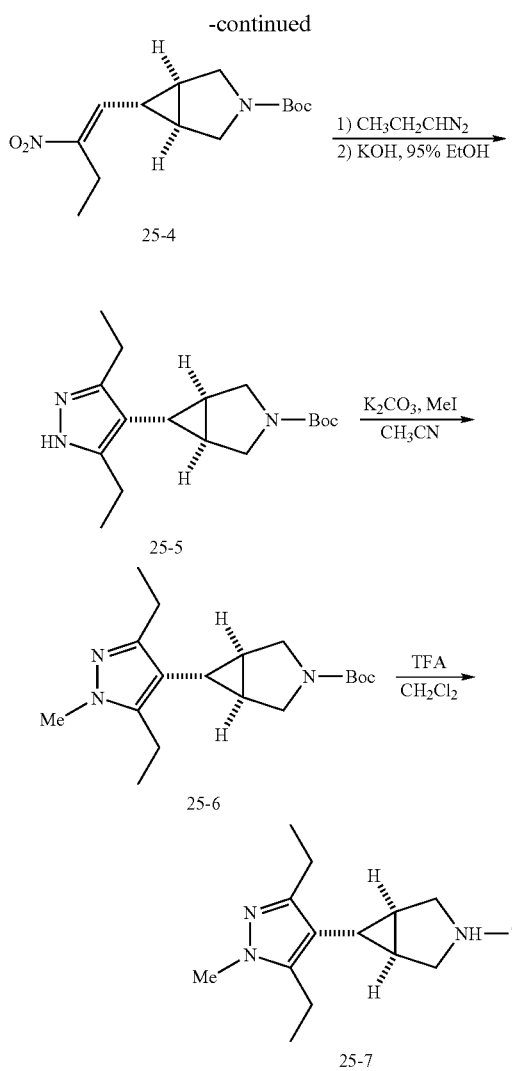

Synthesis of secondary amines with an azabicyclo[3.1.0] hexane ring system is shown in Scheme 25. Treatment of bicycle 25-1 (prepared as described in Brighty, K. E.; Castaldi, M. J. *Synlett* 1996, 1097) with Boc anhydride in methylene chloride affords protected derivative 25-2. Swern oxidation provides aldehyde 25-3, which upon treatment with 1-nitropropane and potassium fluoride in isopropanol, followed by elimination by addition of dicyclohexylcarbodiimide and copper (I) chloride, yields olefin 25-4 as a mixture of geometric isomers. Treatment of this nitro-olefin with diazopropane, followed by treatment with potassium hydroxide in aqueous ethanol, affords the pyrazole 25-5. Alkylation of 25-5 with methyl iodide in the presence of potassium carbonate yields the N-methyl derivative 25-6, which can be deprotected to the desired secondary amine intermediate 25-7 with trifluoroacetic acid in methylene chloride. Other alkylating agents can be used in place of methyl iodide to afford the corresponding N-substituted derivatives. Likewise, other nitromethylalkanes can be employed in place of 1-nitropropane, and alternative diazoalkanes in place of diazopropane can be utilized, to afford the corresponding final products analogous to 25-7.

The following examples serve to illustrate the invention:

EXAMPLE 1

N-{1-[3-(Benzenesulfonylmethylamino)-3-phenylpropyl] piperidin-4-yl}-N-phenylpropionamide Step 1: N-Methyl-N-(1-phenylbut-3-enyl)benzenesulfonamide DIAD (9.0 mL, 45.9 mmol) was added dropwise over 10 min to a stirred solution of 1-phenyl-3-buten-1-ol (4.0 g, 27.0 mmol), PPh$_3$ (10.6 g, 40.5 mmol) and N-methylphenylsulfonamide (6.0 g, 35.0 mmol) in THF (200 mL) under N$_2$ and the resulting mixture was stirred at RT for 20 h. H$_2$O (200 mL) and Et$_2$O (200 mL) were added and separated. The organics were washed with brine (150 mL) and concentrated under reduced pressure while loading on to MgSO$_4$. The mixture was then purified by column chromatography on silica eluting with 3% Et$_2$O/iso-hexanes to yield the sulfonamide (6.45 g, 79%). $^1$H NMR (CDCl$_3$, 360 MHz) δ 7.78 (2H, d, J=7.8 Hz), 7.53 (1H, t, J=7.8 Hz), 7.44 (2H, t, J=7.8 Hz), 7.30–7.18 (5H, m), 5.67–5.52 (1H, m), 5.20 (1H, t, J=7.8 Hz), 5.02 (1H, dd, J=17.1, 1.5 Hz), 4.93 (1H, dd, J=10.2, 1.3 Hz), 2.70 (1H, app. quintet, J=7.1 Hz), 2.65 (3H, s), 2.44 (1H, app. quintet, J=7.1 Hz).

Step 2: N-(3-Hydroxy-1-phenylpropyl)-N-methylbenzenesulfonamide

Ozone was bubbled through a solution of the product of Step 1 (1.0 g, 3.3 mmol) in MeOH (50 mL) at −78° C. for 30 min, then after appearance of a pale blue colour, the reaction was purged with N$_2$ for several minutes and NaBH$_4$ (245 mg, 6.6 mmol) was added. The resulting solution was allowed to warm to RT and stirred for a further 15 min at RT. The reaction was quenched by the addition of NH$_4$Cl solution (10 mL) and then concentrated under reduced pressure. H$_2$O (50 mL) was added and then extracted with EtOAc (100 ml and 50 mL). The combined organic extracts were dried (MgSO$_4$) and then concentrated under reduced pressure to yield the alcohol (0.94 g, 93%). $^1$H NMR (CDCl$_3$, 400 MHz) δ 7.81 (2H, d, J=7.2 Hz), 7.65–7.45 (3H, m), 7.20–7.13 (3H, m), 6.93 (2H, d, J=7.5 Hz), 5.25 (1H, dd, J=9.1, 6.3 Hz), 3.90–3.80 (1H, m), 3.74–3.59 (1H, m), 2.63 (3H, s), 2.13–1.98 (2H, m).

Step 3: N-(3-Iodo-1-phenylpropyl)-N-methylbenzenesulfonamide

Mesyl chloride (286 μL, 3.67 mmol) was added to a stirred solution of the product of Step 2 (0.94 g, 3.1 mmol) in $^i$Pr$_2$NEt (1.59 mL, 9.2 mmol) and CH$_2$Cl$_2$ (50 mL) at 0° C. under N$_2$. The reaction mixture was stirred for 2 h, slowly warming to RT and then was diluted with CH$_2$Cl$_2$ (50 mL) and washed sequentially with H$_2$O (30 mL), NaHCO$_3$ solution (30 mL) and brine (30 mL). The organics were dried (MgSO$_4$) and then concentrated under reduced pressure. The crude residue was taken up in acetone (50 mL), KI (560 mg, 3.37 mmol) added and the mixture was heated at reflux overnight. After cooling to RT, the solvent was removed under reduced pressure and replaced with Et$_2$O (70 mL). This was then washed with H$_2$O (50 mL), Na$_2$S$_2$O$_7$ solution (30 mL) and brine (30 mL), then concentrated under reduced pressure while dry loading onto MgSO$_4$. The residue purified by column chromatography on silica eluting with 40% Et$_2$O/iso-hexanes to yield the iodide (0.87 g, 68%). $^1$H NMR (CDCl$_3$, 400 MHz) δ 7.78 (2H, d, J=7.2Hz), 7.60–7.43 (3H, m), 7.25–7.20 (3H, m), 7.15–7.07 (2H, m), 5.18 (1H, t, J=7.6 Hz), 3.15–3.02 (2H, m), 2.65 (3H, s) 2.41 (1H, app. quintet, J=7 Hz), 2.30 (1H, app. quintet, J=7 Hz).

Step 4: N-{1-[3-(Benzenesulfonylmethylamino)-3-phenyl-propyl]piperidin-4-yl}-N-phenylpropionamide A mixture of the product of Step 4 (100 mg, 0.24 mmol), N-phenyl-N-(4-piperidinyl)propanamide (84 mg, 0.36 mmol) and KHCO$_3$ (48 mg, 0.48 mmol) was combined in MeCN (5 mL) and heated at 65° C. for 8 h. The crude reaction mixture was then poured onto a 5 g SCX cartridge and washed with MeOH and then 2 M NH$_3$ solution in MeOH to remove the desired compound. The desired fractions were concentrated under reduced pressure whilst dry loading onto MgSO$_4$ and then purified by column chromatography on silica eluting with 3% MeOH/CH$_2$Cl$_2$ to yield the amine (59 mg, 47%). $^1$H NMR (CDCl$_3$, 360 MHz) δ 7.72 (2H, d, J=7.2 Hz), 7.51 (1H, t, J=7.4 Hz), 7.46–7.31 (5H, m), 7.25–7.10 (5H, m), 7.06 (2H, d, J=6.4 Hz), 5.05 (1H, t, J=7.6 Hz), 4.65–4.53 (1H, m), 2.80 (1H, d, J=8.7 Hz), 2.71 (1H, d, J=11.1 Hz), 2.63 (3H, s), 2.22–2.05 (2H, m), 2.02–1.68 (6H, m), 1.91 (2H, q, J=7.4 Hz), 1.40–1.25 (2H, m), 1.00 (3H, t, J=7.4 Hz). MS (ES$^+$) C$_{30}$H$_{37}$N$_3$O$_3$S requires: 519, found: 520 (M+H$^+$, 100%).

EXAMPLE 2

N-{3-[4-(2-Methyl-2H-pyrazol-3-yl)piperidin-1-yl]-1-phenylpropyl}benzenesulfonamide Step 1: 4-(2-Methyl-2H-pyrazol-3-yl)-3,6-dihydro-2H-pyridine-1-carboxylic acid butyl ester A solution of BuLi (13.3 mmol) in hexane (1.6 M, 8.3 mL) was added to a stirred solution of $^i$Pr$_2$NH (1.87 mL, 13.3 mmol) in THF (15 mL) at 0° C. under N$_2$. The resulting solution was stirred for 20 min and then cooled to −78° C. and N-methyl pyrazole (0.99 g, 12.1 mmol) was added. The mixture was stirred for 1 h at −78° C. and then a solution of ZnCl$_2$ (1.8 g, 13.3 mmol) in THF (10 mL) was added and the reaction was allowed to warm to RT and stirred for a further 20 min. A solution of 1-(tert-butoxycarbonyl)-4-[(trifluoromethanesulfonyl)oxy]-1,2,3,6-tetrahydropyridine (Synthesis 1991, 11, 993–5) (150 mg, 0.53 mmol) in THF (5 mL) and Pd(PPh$_3$)$_4$ (347 mg, 5 mol %) were added and the reaction was heated at reflux for 3 h. The mixture was partitioned between EtOAc (75 mL) and NH$_4$Cl solution (75 mL), separated and the organics were washed with H$_2$O (75 mL) and brine (50 mL). After concentrating under reduced pressure, the residue was purified by column chromatography on silica eluting with 100% EtOAc to yield the pyrazole (1.30 g, 82%). $^1$H NMR (CDCl$_3$, 360 MHz) δ 7.41 (1H, d, J=1.9 Hz), 6.13 (1H, d, J=1.9 Hz), 5.83 (1H, broad s), 4.10–4.00 (2H, m), 3.88 (3H, s), 3.62 (2H, t, J=5.7 Hz), 2.45–2.37 (2H, m), 1.49 (9H, s). MS (ES$^+$) C$_{14}$H$_{21}$N$_3$O$_2$ requires: 263, found: 264 (M+H$^+$, 100%).

Step 2: 4-(2-Methyl-2H-pyrazol-3-yl)piperidine-1-carboxylic acid butyl ester

A mixture of the product of Step 1 (1.30 g, 4.9 mmol) and 20% Pd(OH)$_2$ on carbon (600 mg) in MeOH (30 mL) was stirred at RT under an N$_2$ atmosphere for 8 h. The mixture was filtered through a celite pad and the pad washed with MeOH (70 mL). To give after concentrating under reduced pressure, the piperidine (1.25 g, 96%). $^1$H NMR (CDCl$_3$, 360 MHz) δ7.39 (1H, d, J=1.9 Hz), 6.00 (1H, d, J=1.9 Hz), 4.30–4.17 (2H, m), 3.83 (3H, s), 2.90–2.67 (3H, m), 1.95–1.81 (2H, m), 1.65–1.45 (2H, m), 1.48 (9H, s). MS (ES$^+$) C$_{14}$H$_{23}$N$_3$O$_2$ requires: 265, found: 266 (M+H$^+$, 65%).

Step 3: 4-(2-Methyl-2H-pyrazol-3-yl)piperidine trifluoroacetic acid salt

A mixture of the product of Step 2 (1.25 g, 4.7 mmol) was stirred with TFA (3 mL) and CH$_2$Cl$_2$ (3 mL) at RT for 4 h and then concentrated to give the piperidine. TFA salt (2.9 g, approx. amine.4 TFA) as a viscous oil. $^1$H NMR (d$^6$-DMSO, 360 MHz) δ 8.65 (1H, broad s), 8.38 (1H, broad s), 7.33 (1H, d, J=1.9 Hz), 6.05 (1H, d, J=1.9 Hz), 3.78 (3H, s), 3.35 (2H, d, J=13.0 Hz), 3.10–2.94 (3H, m), 1.99 (2H, d, J=13.0 Hz), 1.69 (2H, app. q, J=13.0 Hz).

Step 4: {3-[4-(2-Methyl-2H-pyrazol-3-yl)piperidin-1-yl]-1-phenyl-propyl}carbamic acid butyl ester NaBH(OAc)$_3$ was added to a stirred solution of the product of Step 3 (515 mg, 0.83 mmol) and (3-oxo-1-phenylpropyl) carbamic acid t-butyl ester (206 mg, 0.83 mmol) (prepared as described for the chiral aldehyde in Tetrahedron Lett. 1998; 39; 5951–5954) in Et$_3$N (418 mg, 4.1 mmol) and 1,2-DCE (10 mL) and the resulting mixture was stirred at RT overnight. After dilution with CH$_2$Cl$_2$ (50 mL) and washing with NaHCO$_3$ solution (20 mL) and brine (30 mL), the organics were dried (MgSO$_4$) and concentrated under reduced pressure to give the crude tertiary amine (340 mg, Quant.). $^1$H NMR (CDCl$_3$, 360 MHz) δ 7.39 (1H, d, J=1.9 Hz), 7.35–7.20 (5H, m), 6.04 (1H, d, J=1.9 Hz), 4.85–4.75 (1H, broad s), 3.81 (3H, s), 3.10–2.92 (4H, m), 2.60–2.50 (1H, m), 2.42–2.30 (2H, m), 2.10–1.30 (6H, m). MS (ES$^+$) C$_{23}$H$_{34}$N$_4$O$_2$ requires: 398, found: 399 (M+H$^+$, 100%).

Step 5: 3-[4-(2-Methyl-2H-pyrazol-3-yl)piperidin-1-yl]-1-phenylpropylamine

The product of Step 4 (340 mg, 0.83 mmol) was taken up in CH$_2$Cl$_2$ (4 mL) and TFA (2 mL) at stirred at RT for 45 min. After concentrating under reduced pressure, the crude salt was partitioned between 0.5 N NaOH solution (30 mL) and CH$_2$Cl$_2$ (50 mL). The organics were separated and the aqueous extracted with CH$_2$Cl$_2$ (2×30 mL). The combined organic extracts were dried (MgSO$_4$) and concentrated under reduced pressure to yield the bis-amine (225 mg, 91%). $^1$H NMR (CDCl$_3$, 360 MHz) δ 7.38–7.20 (6H, m), 6.02 (1H, d, J=1.9 Hz), 4.00 (1H, t, J=6.6 Hz), 3.80 (3H, s), 3.02 (2H, t, J=12.3 Hz), 2.60–2.30 (3H, m), 2.02 (2H, app. q, J=11 Hz), 1.90–1.60 (6H,m).

Step 6: N-{3-[4-(2-Methyl-2H-pyrazol-3-yl)piperidin-1-yl]-1-phenylpropyl}benzenesulfonamide A solution of benzenesulfonyl chloride (73 mg, 0.41 mmol) in CH$_2$Cl$_2$ (3 mL) was added dropwise over 1 min to a stirred solution of the product of Step 5 (112 mg, 0.38 mmol) and Et$_3$N (104 µL, 0.76 mmol) in CH$_2$Cl$_2$ (15 mL) at RT under N$_2$. The reaction was stirred at RT for 1 h and was then diluted with CH$_2$Cl$_2$ (50 mL) and washed with NaHCO$_3$ solution (15 mL) and brine (15 mL). The organics were concentrated under reduced pressure while dry loading onto MgSO$_4$ and purified by column chromatography on silica eluting with 4% MeOH/CH$_2$Cl$_2$ to yield the sulfonamide (122 mg, 74%). $^1$H NMR (CDCl$_3$, 360 MHz) δ 7.65 (2H, d, J=8.8 Hz), 7.45–7.38 (2H, m), 7.32 (2H, t, J=7.8 Hz), 7.20–7.08 (5H, m), 6.13 (1H, d, J=1.9 Hz), 4.60 (1H, dd, J=7.4, 4.4 Hz), 3.84 (3H, s), 3.04 (2H, d, J=11.1 Hz), 2.65–2.55 (1H, m), 2.47–2.37 (2H, m), 2.12–1.70 (8H, m). MS (ES$^+$) C$_{24}$H$_{30}$N$_4$O$_2$S requires: 438, found: 439 (M+H$^+$, 100%).

EXAMPLE 3

N-{3-[4-(2-Ethyl-5-methyl-2H-pyrazol-3-yl)piperidin-1-yl]-1-phenylpropyl}benzenesulfonamide Step 1: 4-(1-Ethyl-5-methyl-1H-pyrazol-3-yl)piperidine-1-carboxylic acid tert-butyl ester and 4-(2-ethyl-5-methyl-2H-pyrazol-3-yl)piperidine-1-carboxylic acid tert-butyl ester A solution of BuLi (56.5 mmol) in hexanes (2.5 M, 22.6 mL) was added dropwise over 8 min to a stirred solution of $^iPr_2NH$ (8.0 mL, 56.5 mmol) in THF (150 mL) at 0° C. under $N_2$. After 20 min, the reaction was cooled to −78° C. and a solution of acetone (4.09 mL, 55.7 mmol) in THF (10 mL) was added dropwise over 5 min and then the mixture was stirred for a further hour. Meanwhile, CDI (4.92 g, 30.3 mmol) was added to a stirred solution of 1-boc-piperidine-4-carboxylic acid (6.33 g, 27.6 mmol) in THF (100 mL) at RT under $N_2$. This was then stirred at RT for 45 min and then added by cannula into the above solution at −78° C. under $N_2$. The resulting solution was stirred at −78° C. for 45 min, before warming to RT and stirring for a further hour. The reaction was then diluted with EtOAc (200 mL) and washed with 1M citric acid solution (2×100 mL), $NaHCO_3$ solution (2×100 mL) and brine (50 mL), dried ($MgSO_4$) and concentrated under reduced pressure to yield the crude 1,3-dicarbonyl compound (5.68 g). EtOH (20 mL), ethylhydrazine oxalate (1.79 g, 11.9 mmol) and $Et_3N$ (1.65 mL, 11.9 mol) were then added to this crude residue (1.6 g, 5.94 mmol) and the mixture stirred at RT for 36 h. $H_2O$ (30 mL) was added and the organics extracted with $CH_2Cl_2$ (3×30 mL), dried ($MgSO_4$) and the solution concentrated under reduced pressure while dry loading onto $MgSO_4$. The residue purified by column chromatography on silica eluting with 100% $Et_2O$ to yield first 4-(1-ethyl-5-methyl-1H-pyrazol-3-yl)piperidine-1-carboxylic acid tert-butyl ester (224 mg) and then 4-(2-ethyl-5-methyl-2H-pyrazol-3-yl)piperidine-1-carboxylic acid tert-butyl ester (313 mg).

First isomer: $^1$H NMR (CDCl$_3$, 400 MHz) δ 5.79 (1H, s), 4.20–4.05 (2H, m), 4.02 (2H, q, J=7.2 Hz), 2.88–2.64 (3H, m), 2.24 (3H, s), 1.89 (2H, d, J=8.5 Hz), 1.63–1.50 (2H, m), 1.48 (9H, s), 1.37 (3H, t, J=7.2 Hz).

Second isomer: $^1$H NMR (CDCl$_3$, 400 MHz) δ 5.77 (1H, s), 4.25–4.17 (2H, m), 4.03 (2H, q, J=7.2 Hz), 2.81 (3H, t, J=9.0 Hz), 2.66 (1H, tt, J=9.0, 1.5 Hz), 2.22 (3H, s), 1.84 (2H, d, J=8.5 Hz), 1.63–1.48 (2H, m), 1.48 (9H, s), 1.41 (3H, t, J=7.2 Hz).

Step 2: 4-(2-Ethyl-5-methyl-2H-pyrazol-3-yl)piperidine 4-(2-Ethyl-5-methyl-2H-pyrazol-3-yl)piperidine-1-carboxylic acid tert-butyl ester (313 mg, 1.07 mmol) was taken up in $CH_2Cl_2$ (3 mL) and TFA (3 mL) and stirred at RT for 3 h, before concentrating under reduced pressure to yield the TFA salt. This residue was taken up in MeOH (10 mL) and poured onto a 5 g SCX cartridge and then washed with MeOH and then a solution of 2 M $NH_3$ in MeOH. The desired fractions were concentrated under reduced pressure to give the free piperidine (225 mg, Quant.). $^1$H NMR (CDCl$_3$, 360 MHz) δ 5.80 (1H, s), 4.02 (2H, q, J=7.2 Hz), 3.17 (2H, d, J=9.6, 2.6 Hz), 2.72 (2H, td, J=12.2, 2.4 Hz), 2.63 (2H, tt, J=11.9, 3.6 Hz), 2.23 (3H, s), 1.83 (2H, d, J=12.2 Hz), 1.65–1.52 (2H, m), 1.41 (3H, t, J=7.2 Hz).

MS (ES$^+$) $C_{11}H_{19}N_3$ requires: 193, found: 194 (M+H$^+$, 100%).

Step 3: N-(1-Phenylbut-3-enyl)benzenesulfonamide

A solution of allyl magnesium bromide (12 mmol) in $Et_2O$ (1.0 M, 12 mL) was added dropwise over 10 min to a stirred solution of N-benzylidenebenzene sulfonamide (2.5 g, 10.2 mmol) in THF (40 mL) under $N_2$. After 2 h the mixture was poured into brine and extracted with EtOAc. These extracts were washed with $H_2O$ and brine then dried ($MgSO_4$) and concentrated under reduced pressure. The residue was purified by column chromatography on silica eluting with $CH_2Cl_2$ to give the benzenesulfonamide as a white solid (1.9 g, 65%). $^1$H NMR (360 MHz, CDCl$_3$) δ 2.44–2.48 (2H, m), 4.39–4.45 (1H, m), 4.79 (1H, d, J=5.6 Hz), 5.04–5.10 (2H, m), 5.46–5.58 (1H, m), 7.04–7.07 (2H, m), 7.15–7.19 (3H, m), 7.32–7.37 (2H, m), 7.43–7.48 (1H, m), 7.64–7.67 (2H, m).

Step 4: N-(3-Oxo-1-phenylpropyl)benzenesulfonamide.

A stream of ozone was passed through a solution of the product of Step 3 (1.9 g, 6.6 mmol) in $CH_2Cl_2$ (90 mL) at −78° C. for 1 h. The solution was then purged with oxygen, $Me_2S$ (1.1 mL, 15 mmol) was added, the cooling bath removed and the mixture allowed to warm to RT. The reaction was complete after 3 days and the solvent removed under reduced pressure and the mixture purified by column chromatography on silica eluting 5–10% MeOH/$CH_2Cl_2$ to give the benzenesulfonamide as a colourless oil (1.6 g, 84%). $^1$H NMR (360 MHz, CDCl$_3$) δ 2.90–3.10 (2H, m), 4.79–4.86 (1H, m), 5.45 (1H, d, J=7.4 Hz), 7.03–7.09 (2H, m), 7.13–7.18 (3H, m), 7.35–7.39 (2H, m), 7.46–7.51 (1H, m), 7.69–7.71 (2H, m), 9.64 (1H, s).

Step 5: N-{3-[4-(2-Ethyl-5-methyl-2H-pyrazol-3-yl)piperidin-1-yl]-1-phenylpropyl}benzenesulfonamide A solution of the product of Step 4 (253 mg, 0.88 mmol) and the product of Step 2 (225 mg, 0.88 mmol) were taken up in 1,2-DCE (10 mL) and treated with NaBH(OAc)$_3$ (321 mg, 1.51 mmol) at RT under $N_2$ and the mixture stirred overnight. The reaction was quenched by the addition of NH$_4$Cl solution (20 mL), separated and then the aqueous was extracted with $CH_2Cl_2$ (20 mL). The combined organic extracts were concentrated under reduced pressure whilst dry loading onto MgSO$_4$ and then residue purified by column chromatography on silica eluting with 15% EtOH/EtOAc. The compound was further purified by reverse phase HPLC and the desired fractions were concentrated under reduced pressure to remove the MeCN, then basified with 0.5 N NaOH solution and extracted with $CH_2Cl_2$ (3×30 mL), dried (MgSO$_4$) and concentrated under reduced pressure to yield the desired sulfonamide (70 mg, 17%).

$^1$H NMR (CDCl$_3$, 360 MHz) δ 7.64 (2H, d, J=7.6 Hz), 7.43 (1H, t, J=7.3 Hz), 7.32 (2H, t, J=7.6 Hz), 7.25–7.07 (5H, m), 5.91(1H, s), 4.58 (1H, dd, J=6.1, 4.4 Hz), 4.03 (2H, q, J=7.3 Hz), 3.03 (2H, d, J=11.5 Hz), 2.62–2.49 (1H, m), 2.47–2.32 (2H, m), 2.25 (3H, s), 2.08–1.70 (8H, m), 1.41 (3H, t, J=7.3 Hz). MS (ES$^+$) $C_{26}H_{34}N_4O_2S$ requires: 466, found: 467 (M+H$^+$, 30%).

EXAMPLE 4

N-{3-[4-(2,5-Dimethyl-2H-pyrazol-3-yl)piperidin-1-yl]-1-phenylpropyl}benzenesulfonamide hydrochloride Step 1: 3-[4-(2,5-Dimethyl-2H-pyrazol-3-yl)piperidin-1-yl]-1-phenylpropan-1-ol A mixture of acetophenone (414 mg, 3.45 mmol), 4-(2,5-dimethyl-2H-pyrazol-3-yl)piperidine.TFA salt (prepared as described for 4-(2-ethyl-5-methyl-2H-pyrazol-3-yl)piperidine in Example 3, Steps 1 and 2) (1.1 g, 3.80 mmol) and paraformaldehyde (120 mg, 4 mmol) in EtOH (2 mL) and conc. HCl (5 μL) was heated at reflux for 14 h and then cooled to RT and concentrated under reduced pressure. The residue was taken up in EtOH (10 mL), NaBH$_4$ (260 mg, 6.9 mmol) added and the mixture stirred at RT for 15 min, then more NaBH$_4$ (260 mg, 6.9 mmol) was added. After stirring for a further 5 min, NH$_4$Cl solution (5 mL) was added and the organic solvents removed under reduced pressure. The aqueous was extracted with CH$_2$Cl$_2$ (3×50 mL). The organic extracts were concentrated under reduced pressure whilst dry loading onto MgSO$_4$ and purified by column chromatography on silica eluting with 8% MeOH/CH$_2$Cl$_2$ to yield the desired alcohol (334 mg, 28%). $^1$H NMR (CDCl$_3$, 400 MHz) δ 7.43–7.32 (4H, m), 7.29–7.22 (1H, m), 5.81 (1H, s), 4.95 (1H, dd, J=7.0, 4.4 Hz), 3.74 (3H, s), 3.21 (1H, d, J=12.3 Hz), 3.14 (1H, d, J=11.9 Hz), 2.75–2.67 (1H, m), 2.63–2.52 (2H, m), 2.24–2.15 (1H, m), 2.22 (3H, s), 2.06–1.65 (7H, m). MS (ES$^+$) C$_{19}$H$_{27}$N$_3$O requires: 313, found: 314 (M+H$^+$, 100%).

Step 2: 3-[4-(2,5-Dimethyl-2H-pyrazol-3-yl)piperidin-1-yl]-1-phenylpropylamine

Tosyl chloride (203 mg, 1.06 mmol) was added to a stirred solution of the product of Step 2 (304 mg, 0.97 mmol) and Et$_3$N (176 µL, 1.26 mmol) in CH$_2$Cl$_2$ (10 mL) at 0° C. under N$_2$. The mixture was stirred for 1 h and then the reaction was warmed to RT and stirred for a further 2 h, more tosyl chloride (100 mg, 0.52 mmol) and Et$_3$N (176 µL, 1.26 mmol) were added and the reaction was stirred for 20 h. After dilution with CH$_2$Cl$_2$ (30 mL), the solution was washed with NaHCO$_3$ solution (20 mL) and brine (20 mL) and then concentrated under reduced pressure. The crude tosylate was taken up in DMF (2 mL), NaN$_3$ (189 mg, 2.9 mmol) added and the mixture was heated at 50° C. for 3 h and then diluted with EtOAc (70 mL), washed with H$_2$O (3×50 mL) and concentrated under reduced pressure. The azide was taken up in EtOH (10 mL) and then PtO$_2$ (50 mg) added and an H$_2$ atmosphere introduced. The mixture was stirred for 4 h, then was filtered through celite and then concentrated under reduced pressure while loading onto MgSO$_4$. The compound was purified by column chromatography on silica eluting with 15–25% MeOH/CH$_2$Cl$_2$ to yield the desired amine (165 mg, 54%). $^1$H NMR (CDCl$_3$, 360 MHz) δ 7.38–7.30 (4H, m), 7.28–7.21 (1H, m), 5.80 (1H, s), 4.00 (1H, t, J=6.9 Hz), 3.72 (3H, s), 3.01 (2H, t, J=11.8 Hz), 2.80 (1H, q, J=7.2 Hz), 2.53–2.30 (3H, m), 2.21 (3H, s), 2.06–1.60 (7H, m). MS (ES$^+$) C$_{19}$H$_{28}$N$_4$ requires: 312, found: 313 (M+H$^+$, 100%).

Step 3: N-{3-[4-(2,5-Dimethyl-2H-pyrazol-3-yl)piperidin-1-yl]-1-phenylpropyl}benzenesulfonamide hydrochloride A mixture of the product of Step 2 (41 mg, 0.13 mmol) and benezenesulfonyl chloride (25 mg, 0.14 mmol) in CH$_2$Cl$_2$ (5 mL) and Et$_3$N (27 µL, 0.14 mmol) was stirred at RT under N$_2$ for 30 min. The solution was then washed with NaHCO$_3$ solution (5 mL), and concentrated under reduced pressure whilst dry loading onto MgSO$_4$. The residue was purified by column chromatography on silica eluting with 5% MeOH/CH$_2$Cl$_2$ to yield the desired amine, this was then taken up in CH$_2$Cl$_2$ and treated with 1 M HCl solution in Et$_2$O and concentrated to yield the HCl salt (53 mg, 82%). $^1$H NMR (d$^6$-DMSO, 360 MHz) δ, 10.51 (1H, s), 8.48 (1H, d, J=8.9 Hz), 7.59 (2H, d, J=7.3 Hz), 7.46 (1H, t, J=7.3 Hz), 7.36 (2H, t, J=7.3 Hz), 7.18–7.05 (5H, m), 6.01 (1H, s), 4.40–4.31 (1H, m), 3.68 (3H, s), 3.47–3.35 (2H, m), 3.13–2.80 (5H, m), 2.15–1.80 (6H, m), 2.06 (3H, s). MS (ES$^+$) C$_{25}$H$_{32}$N$_4$O$_2$S requires: 452, found: 453 (M+H$^+$, 70%).

EXAMPLE 5

(R)-N-{3-[4-(2-Ethyl-5-methyl-2H-pyrazol-3-yl)piperidin-1-yl]-1-phenylpropyl}-N-methylbenzenesulfonamide Step 1: (R)-{3-[4-(2-Ethyl-5-methyl-2H-pyrazol-3-yl)piperidin-1-yl]-1-phenylpropyl}carbamic acid tert-butyl ester The reaction was carried out as described for Example 2 Step 4 using (R)-(3-oxo-1-phenylpropyl)carbamic acid tert-butyl ester (136 mg, 0.54 mol, 4-(2-ethyl-5-methyl-2H-pyrazol-3-yl)-piperidine.TFA salt (Example 3 Step 2) (252 mg, 0.54 mmol), Et$_3$N (165 mg, 1.62 mmol) and NaBH(OAc)$_3$ (231 mg, 1.09 mmol) to yield the crude Boc-amine (273 mg, Quant). $^1$H NMR (CDCl$_3$, 360 MHz) δ 7.38–7.18 (5H, m), 5.82 (1H, s), 4.75 (1H, broad s), 4.01 (2H, q, J=7.2 Hz), 3.09 (2H, q, J=7.4 Hz), 2.60–1.40 (20H, m), 2.23 (3H, s), 1.38 (3H, t, J=7.2 Hz). MS (ES$^+$) C$_{25}$H$_{38}$N$_4$O$_2$ requires: 426, found: 427 (M+H$^+$, 100%).

Step 2: (R)-3-[4-(2-Ethyl-5-methyl-2H-pyrazol-3-yl)piperidin-1-yl]-1-phenylpropylamine The crude ester (273 mg, 0.54 mmol) was taken up in CH$_2$Cl$_2$ (4 mL) and TFA (2 mL) was added. The mixture was stirred at RT for 45 min and then concentrated under reduced pressure, before being partitioned between 0.5 NaOH (30 mL) and CH$_2$Cl$_2$ (50 mL). The layers were separated and the aqueous layer was extracted with CH$_2$Cl$_2$ (2×30 mL). The combined organic extracts were dried (MgSO$_4$) and concentrated under reduced pressure to yield the free amine (155 mg, 87%). $^1$H NMR (CDCl$_3$, 400 MHz) δ 7.38–7.23 (5H, m), 5.79 (1H, s), 4.05–3.95 (3H, m), 3.01 (2H, t, J=13.1 Hz), 2.50–2.30 (3H, m), 2.23 (3H, s), 1.99 (2H, q, J=12.4 Hz), 1.88–1.60 (6H, m), 1.38 (3H, t, J=7.2 Hz). MS (ES$^+$) C$_{20}$H$_{30}$N$_4$ requires: 326, found: 327 (M+H$^+$, 70%).

Step 3: (R)-N-{3-[4-(2-Ethyl-5-methyl-2H-pyrazol-3-yl)piperidin-1-yl]-1-phenylpropyl}benzenesulfonamide A solution of benzene sulfonyl chloride (92 mg, 0.52 mmol) in CH$_2$Cl$_2$ (3 mL) was added dropwise to a stirred solution of the amine (155 mg, 0.47 mmol) and Et$_3$N (132 µL, 0.94 mmol) in CH$_2$Cl$_2$ (4 mL) at RT under N$_2$ and the mixture was stirred for 1 h. The solution was diluted with CH$_2$Cl$_2$ (30 mL) and then washed with NaHCO$_3$ solution (5 mL) and brine (15 mL), then concentrated under reduced pressure whilst dry loading onto MgSO$_4$. The residue was purified by column chromatography on silica eluting with 4% MeOH/CH$_2$Cl$_2$ to yield the desired amine (181 mg, 82%). $^1$H NMR (CDCl$_3$, 400 MHz) δ 7.66 (2H, d, J=7.1 Hz), 7.42 (1H, t, J=7.4 Hz), 7.32 (2H, t, J=7.1 Hz), 7.22–7.08 (5H, m), 5.91 (1H, s), 4.59 (1H, dd, J=6.6, 3.9 Hz), 4.03 (2H, q, J=7.2 Hz), 3.02 (2H, d, J=11.7 Hz), 2.62–2.48 (1H, m), 2.46–2.33 (2H, m), 2.26 (3H, s), 2.10–1.71 (8H, m), 1.38 (3H, t, J=7.2 Hz). MS (ES$^+$) C$_{26}$H$_{34}$N$_4$SO$_2$ requires: 466, found: 467 (M+H$^+$, 70%). This was then converted to the HCl salt using 1 M HCl in Et$_2$O solution.

Step 4: (R)-N-{3-[4-(2-Ethyl-5-methyl-2H-pyrazol-3-yl)piperidin-1-yl]-1-phenylpropyl}-N-methylbenzenesulfonamide A mixture of the sulfonamide (103 mg, 0.19 mmol) and NaO$^t$Bu (73 mg, 0.76 mmol) was stirred in THF (3 mL) and DMF (3 mL) at RT under N$_2$ for 10 min and then MeI (81 mg, 0.57 mmol) was added. The mixture was stirred at RT overnight, then concentrated under reduced pressure whilst azeotroping with xylene (2×30 mL) and then taken up in MeOH/CH$_2$Cl$_2$ and dry loaded onto MgSO$_4$. The residue was purified by column chromatography on silica eluting with 4% MeOH/CH$_2$Cl$_2$ to yield the desired methyl sulfonamide (43 mg, 41%). $^1$H NMR (CDCl$_3$, 360 MHz) δ 7.78 (2H, d, J=7.4 Hz), 7.53 (1H, t, J=7.4 Hz), 7.45 (2H, t, J=7.9 Hz), 7.28–7.15 (5H, m), 5.80 (1H, s), 5.16 (1H, t, J=7.6 Hz), 4.01 (2H, q, J=7.2 Hz), 2.95 (1H, d, J=11.0 Hz), 2.85 (1H, d, J=11.0 Hz), 2.68 (3H, s), 2.52–2.40 (1H, m), 2.37–1.55 (10H, m), 2.23 (3H, s), 1.40 (3H, t, J=7.2 Hz).

EXAMPLE 6

N-{1-(4-Chlorophenyl)-3-[4-(2-ethyl-5-methyl-2H-pyrazol-3-yl)piperidin-1-yl]propyl}-N-methylbenzenesulfonamide Step 1: 1-(4-Chlorophenyl)-3-[4-(2-ethyl-5-methyl-2H-pyrazol-3-yl)piperidin-1-yl]propan-1-one 4-(2-Ethyl-5-methyl-2H-pyrazol-3-yl)-piperidine (Example 3 Step 2) (50 mg, 0.26 mmol) and 1-(4-chlorophenyl)propenone (52 mg, 0.31 mmol) were combined in toluene (5 mL) and stirred at RT for 10 min. The solvent was removed under reduced pressure and the residue was dissolved in CH$_2$Cl$_2$ and loaded onto an SCX cartridge. This was washed with CH$_2$Cl$_2$ then 2M NH$_3$ in MeOH solution to elute the compound. The desired fractions were evaporated under reduced pressure to give the titled compound (90 mg, 96%). $^1$H NMR (CDCl$_3$, 400 MHz) δ 7.91 (2H, d, J=8.6 Hz), 7.44 (2H, d, J=8.6 Hz), 5.80 (1H, s), 4.01 (2H, q, J=7.4 Hz), 3.35–3.22 (2H, m), 3.20–3.18 (2H, m), 3.10–2.87 (2H, m), 2.65–2.50 (1H, m), 2.40–2.16 (5H, m), 1.98–1.73 (4H, m), 1.39 (3H, t, J=7.4 Hz). MS (ES$^+$) C$_{20}$H$_{26}$ClN$_3$O requires: 360, found: 360/362 (3:1, M+H$^+$).

Step 2: N-{1-(4-Chlorophenyl)-3-[4-(2-ethyl-5-methyl-2H-pyrazol-3-yl)piperidin-1-yl]propyl}-N-methylbenzenesulfonamide A solution of the product of Step 1 (90 mg, 0.25 mmol), in EtOH (10 mL) was treated with NaBH$_4$ (38 mg, 1.0 mmol) and stirred at RT for 1 h. The reaction was quenched with NH$_4$Cl solution, then the EtOH was removed under reduced pressure. The residue was partitioned between CH$_2$Cl$_2$ and water and the organic layer separated and the aqueous re-extracted with CH$_2$Cl$_2$. The combined organic extracts were dried (MgSO$_4$) and concentrated under reduced pressure to give 1-(4-chloro-phenyl)-3-[4-(2-ethyl-5-methyl-2H-pyrazol-3-yl)-piperidin-1-yl]-propan-1-ol as a gum (30 mg). This intermediate was dissolved in THF (5 mL), treated with N-methylbenzenesulfonamide (17 mg, 0.1 mmol), PPh$_3$ (26 mg, 0.1 mmol) and DIAD (20 µL, 0.1 mmol) and stirred overnight at RT. The solvent was evaporated under reduced pressure and the residue dissolved in CH$_2$Cl$_2$ and loaded onto a 5 g SCX cartridge, which was eluted with CH$_2$Cl$_2$ then 2M NH$_3$ in MeOH solution. The fractions containing the desired material were concentrated under reduced pressure and were further purified by silica chromatography eluting 1–3% MeOH/CH$_2$Cl$_2$ to yield the desired sulfonamide. $^1$H NMR (CDCl$_3$, 400 MHz) δ 7.70 (2H, d, J=7.3 Hz), 7.48 (1H, d, J=7.3 Hz), 7.40 (2H, t, J=7.3 Hz), 7.20–7.15 (2H, m), 7.07 (2H, d, J=8.4 Hz), 5.73 (1H, s), 5.07 (1H, t, J=7.3 Hz), 3.94 (2H, q, J=7.4 Hz), 2.92–2.68 (2H, m), 2.60 (3H, s), 2.48–2.32 (1H, m), 2.28–2.05 (5H, m), 2.05–1.40 (8H, m), 1.33 (3H, t, J=7.4 Hz). MS (ES$^+$) C$_{27}$H$_{35}$ClN$_4$O$_2$S requires: 515, found: 515/517 (3:1, M+H$^+$)

EXAMPLE 7

N-[3-(4-Benzylpiperidin-1-yl)-1-phenylpropyl]benzenesulfonamide.

4-Benzylpiperidine (54 µL, 0.30 mmol) was added to a stirred solution of N-(3-oxo-1-phenylpropyl)benzenesulfonamide (83 mg, 0.28 mmol) (Example 3 Step 4) in MeOH (1.0 mL) under N$_2$ and sodium cyanoborohydride (40 mg, 0.62 mmol) added. After 4 h the reaction was quenched with water, applied to an SCX-2 cartridge and washed with MeOH and then 2 M NH$_3$ in MeOH solution. The desired fractions were concentrated under reduced pressure and further purified by reversed phase prep-HPLC system to give the title compound as a residue (10 mg, 7%), after isolating the free base. $^1$H NMR (400 MHz, CDCl$_3$) δ 1.3–2.0 (9H, m), 2.25–2.40 (2H, m), 2.59 (2H, d, J 6.9 Hz), 2.91 (2H, t, J 9.4 Hz), 4.50–4.54 (1H, m), 7.08–7.22 (8H,m), 7.27–7.36 (4H, m), 7.41–7.46 (1H, m), 7.64–7.69 (2H,m). MS (ES$^+$) C$_{27}$H$_{32}$N$_2$O$_2$S requires: 448, found: 449 (M+H$^+$)

EXAMPLE 8

4-Bromo-N-{3-[4-(2-ethyl-5-methyl-2H-pyrazol-3-yl)piperidin-1-yl]-1-phenylpropyl}benzenesulfonamide hydrochloride 4-Bromobenezenesulfonylchloride (33 mg, 0.13 mmol) was added dropwise to a stirred solution of (3-[4-(2-ethyl-5-methyl-2H-pyrazol-3-yl)piperidin-1-yl]-1-phenylpropylamine (48 mg, 0.15 mmol) (prepared as described in Example 5 for the (R)-enantiomer, from racemic (3-oxo-1-phenylpropyl)carbamic acid tert-butyl ester) and Et$_3$N (20 µL, 0.14 mmol) in CH$_2$Cl$_2$ (2 mL) at RT under N$_2$ and the mixture was stirred for 3 h. The solution was diluted with CH$_2$Cl$_2$ (20 mL) and then washed with NaHCO$_3$ solution (20 mL), then the organic layer separated. The aqueous phase was washed with more CH$_2$Cl$_2$ (20 mL) and the combined organic extracts were dried (MgSO$_4$). The solvent was removed under reduced pressure and the residue taken up in Et$_2$O (5 mL). A solution of HCl in Et$_2$O was added and the resultant hydrochloride salt purified by trituration. The title compound (55 mg, 73%) was isolated as a colourless solid. $^1$H NMR (d$^6$-DMSO, 360 MHz) δ 10.87 (1H, s), 8.64 (1H, d, J=9.0 Hz), 7.53 (2H, d, J=8.6 Hz), 7.44 (2H, d, J=8.6 Hz), 7.13 (5H, br. s), 5.87 (1H, s), 4.42–4.35 (1H, m), 4.04 (2H, q, J=7.1 Hz), 3.50–3.37 (2H, m), 3.19–2.85 (5H, m), 2.26–1.88 (9H, m), 1.30 (3H, t, J=7.1 Hz). MS (ES+) C$_{26}$H$_{33}$BrN$_4$O$_2$S requires: 544, found: 545/547 (1:1, M+H$^+$).

EXAMPLE 9

3-Bromo-N-{3-[4-(2-ethyl-5-methyl-2H-pyrazol-3-yl)piperidin-1-yl]-1-phenylpropyl}benzenesulfonamide hydrochloride As described in Example 8 using 3-bromobenezenesulfonyl chloride, the title compound (25 mg, 33%) was isolated as a colourless solid. $^1$H NMR (d$^6$-DMSO, 400 MHz) δ 10.50 (1H, s), 8.64 (1H, d, J=9.1 Hz), 7.62 (1H, dd, J=8.0, 2.8 Hz), 7.55–7.52 (2H, m), 7.30 (1H, t, J=8.2 Hz), 7.15–7.11 (5H, m), 5.82 (1H, s), 4.43–4.38 (1H, m), 4.00 (2H, q, J=7.1 Hz), 3.51–3.41 (2H, m), 3.19–2.88 (5H, m), 2.45–1.85 (9H, m), 1.29 (3H, t, J=7.1 Hz). MS (ES$^+$) C$_{26}$H$_{33}$BrN$_4$O$_2$S requires: 544, found: 545/547 (1:1, M+H$^+$).

EXAMPLE 10

N-{3-[4-(2-Ethyl-5-methyl-2H-pyrazol-3-yl)piperidin-1-yl]-1-phenylpropyl}-4-fluorobenzenesulfonamide hydrochloride As described in Example 8 using 4-fluorobenzenesulfonyl chloride, the title compound (53 mg, 78%) was isolated as a colourless solid. $^1$H NMR (d$^6$-DMSO, 400 MHz) δ 10.50 (1H, s), 8.53 (1H, d, J=9.1 Hz), 7.61–7.53 (2H, m), 7.18–7.10 (7H, m), 5.81 (1H, s), 4.40–4.33 (1H, m), 4.00 (2H, q, J=7.1 Hz), 3.50–3.39 (2H, m), 3.15–2.85 (5H, m), 2.40–1.88 (9H, m), 1.29 (3H, t, J=7.1 Hz). MS (ES$^+$) C$_{26}$H$_{33}$FN$_4$O$_2$S requires: 484, found: 485 (M+H$^+$).

EXAMPLE 11

N-{3-[4-(2-Ethyl-5-methyl-2H-pyrazol-3-yl)piperidin-1-yl]-1-phenylpropyl}-N-phenylmethanesulfonamide hydrochloride As described in Example 8 using benzylsulphonyl chloride, the title compound (38 mg, 57%) was isolated as a colourless solid. $^1$H NMR (d$^6$-DMSO, 400 MHz) δ 10.68 (1H, s), 7.99 (1H, d, J=9.0 Hz), 7.46–7.40 (4H, m), 7.36–7.26 (4H, m), 7.11–7.09 (2H, m), 5.84 (1H, s), 4.49–4.44 (1H, m), 4.07–3.99 (4H, m), 3.49–3.43 (2H, m), 3.13–2.94 (5H, m), 2.30–2.10 (5H, m), 2.03–1.90 (4H, m), 1.30 (3H, t, J=7.1 Hz). MS (ES$^+$) C$_{27}$H$_{36}$N$_4$O$_2$S requires: 480, found: 481 (M+H$^+$).

EXAMPLE 12

1-Methyl-1H-imidazole-4-sulfonic acid{3-14-(2-ethyl-5-methyl-2H-pyrazol-3-yl)-piperidin-1-yl]-1-phenylpropyl}amide (1-Methylimidazol-4-yl)sulfonyl chloride (23 mg, 0.13 mmol) was added dropwise to a stirred solution of 3-[4-(2-ethyl-5-methyl-2H-pyrazol-3-yl)piperidin-1-yl]-1-phenyl-propylamine (see Example 8) (48 mg, 0.15 mmol) and Et$_3$N (20 μL, 0.14 mmol) in CH$_2$Cl$_2$ (2 mL) at RT under N$_2$. The mixture was stirred for 18 h, then was diluted with CH$_2$Cl$_2$ (20 mL) and washed with NaHCO$_3$ solution (20 mL). Then the organic layer was separated and the aqueous phase was re-extracted with CH$_2$Cl$_2$ (20 mL) and the combined organic extracts dried (MgSO$_4$), and concentrated under reduced pressure. The residue was taken up in Et$_2$O (5 mL) and purified by trituration. The title compound (55 mg, 56%) was isolated as a colourless solid. $^1$H NMR (d$^6$-DMSO, 400 MHz) δ 8.28 (1H, d, J=7.8 Hz), 7.68 (1H, s), 7.54 (1H, s), 7.26–7.14 (5H, m), 5.81 (1H, s), 4.35–4.25 (1H, m), 3.93 (2H, q, J=7.2 Hz), 3.60 (3H, s), 2.75–2.50 (3H, m), 2.09 (3H, s), 2.08–2.00 (2H, m), 1.95–1.40 (8H, m), 1.27 (3H, t, J=7.2 Hz). MS (ES$^+$) C$_{24}$H$_{34}$N$_6$O$_2$S requires: 470, found: 471 (1:1, M+H$^+$).

EXAMPLE 13

5-Bromothiophene-2-sulfonic acid{3-[4-(2-ethyl-5-methyl-2H-pyrazol-3-yl)piperidin-1-yl]-1-phenylpropyl}amide hydrochloride (5-Bromothien-2-yl)sulfonylchloride (34 mg, 0.13 mmol) was added dropwise to a stirred solution of 3-[4-(2-ethyl-5-methyl-2H-pyrazol-3-yl)-piperidin-1-yl]-1-phenyl-propylamine (see Example 8 (48 mg, 0.15 mmol) and Et$_3$N (20 μL, 0.14 mmol) in CH$_2$Cl$_2$ (2 mL) at RT under N$_2$ and the mixture was stirred for 3 hours. The solution was diluted with CH$_2$Cl$_2$ (20 mL) and then washed with NaHCO$_3$ solution (20 mL), and the organic layer separated. The aqueous phase was re-extracted with CH$_2$Cl$_2$ (20 mL) and the combined organic layers were dried (MgSO$_4$) and concentrated under reduced pressure. The residue was purified by column chromatography on silica using 5% MeOH/CH$_2$Cl$_2$ as eluent. The fractions containing the desired product were combined and concentrated under reduced pressure. The residue was taken up in Et$_2$O (5 mL) and a solution of HCl in Et$_2$O was added. The resultant solid was purified by trituration to isolate the title compound (8 mg, 10%) as a colourless solid. $^1$H NMR (d$^6$-DMSO, 400 MHz) δ 10.32 (1H, s), 8.85 (1H, d, J=9.1 Hz), 7.24–7.19 (5H, m), 7.09 (1H, d, J=4.0 Hz), 7.06 (1H, d, J=4.0 Hz), 5.80 (1H, s), 4.46–4.40 (1H, m), 3.99 (2H, q, J=7.2 Hz), 3.51–3.41 (2H, m), 3.15–2.87 (5H, m), 2.42–2.00 (5H, m), 1.98–1.80 (4H, m), 1.28 (3H, t, J=7.2 Hz). MS (ES$^+$) C$_{24}$H$_{31}$BrN$_4$O$_2$S$_2$ requires: 550, found: 551/553 (1:1, M+H$^+$).

REFERENCE EXAMPLE 1

(1S)-1-phenyl-3-(4-[3-benzyl-1-ethyl(1H-pyrazol-5-yl)]piperidin-1-yl)propylamine, tris-HCl salt Step A: Methyl (3S)-3-[tert-butoxycarbonylamino]-3-phenylpropionate A solution of 15 mL of DMF charged with (3S)-3-[tert-butoxycarbonylamino]-3-phenylpropionic acid (8 mmol, 2.0 g), methyl iodide (15 mmol, 1.9 mL) and K$_2$CO$_3$ (15 mmol, 2.1 g), was stirred at RT for 16 h. The reaction mixture was poured into 50 mL of saturated NaHCO$_3$, and the resulting solution was extracted with ether (3×50 mL). The combined organic phase was washed with 50 mL of H$_2$O, dried with MgSO$_4$, and the solvent removed under reduced pressure to yield the title compound as a slightly yellow solid. $^1$H NMR (500 MHz, CDCl$_3$): δ 7.26–7.38 (m, 5 H), 5.49 (br s, 1H), 5.13 (br s, 1H), 3.65 (s, 3H), 2.80–2.96 (m, 2H), 1.45 (s, 9H). MS (ESI): m/z 302 (M+Na).

Step B: tert-Butyl(1S)-3-oxo-1-phenylpropylcarbamate

The compound was prepared from the title compound in Example 1, Step A (4 mmol, 1.1 g) as described in WO-A-0039125, pp. 57–58. The aldehyde was further purified by flash chromatography on silica gel using a step gradient of hexanes, 4% EtOAc/hexanes, 8% EtOAc/hexanes, 12% EtOAc/hexanes and 16% EtOAc/hexanes. The aldehyde eluted in 16% EtOAc/hexanes. Removal of solvent under reduced pressure afforded the title compound as a white solid. $^1$H NMR (500 MHz, CDCl$_3$): δ 9.78 (s, 1H), 7.36–7.41 (m, 2H), 7.28–7.35 (m, 3 H), 5.23 (br s, 1H), 5.12 (br s, 1H), 2.84–3.04 (m, 2H), 1.45 (s, 9H). MS (ESI): m/z 290 (dihydrate+Na).

Step C: 1-(1-tert-Butoxycarbonylpiperidin-4-yl)-4-phenylbutane-1,3-dione

Method A:

n-Butyllithium (100 mL, 0.16 mole) was added to a stirred solution of dilsopropylamine (16.16 g, 22.4 mL, 0.16 mole, distilled) in THF (450 mL) at 0° C. over 45 min under nitrogen. Stirring was continued for 10 min at 0° C. after the addition was complete. After cooling to −78° C., phenylacetone (21.45 g, 21.13 mL, 0.16 mole) in THF (100 mL) was added dropwise over 15 min with stirring. This solution was stirred at −78° C. for 1 h. Meanwhile, a solution of N-Boc isonipecotic acid (18.32 g, 0.080 mole) and carbonyl diimidazole (12.98 g, 0.080 mole) in THF (150 mL) was prepared. After stirring for 15 min, this solution was cannulated into the enolate solution dropwise over 15 min. The reaction was stirred at <−70° C. for 1 h and then allowed to warm to RT over 3 h. The reaction was quenched with 1M citric acid (250 mL) and stirred for 16 h. The organic layer was separated and washed with 250 mL each of saturated sodium bicarbonate solution, water and brine. After drying over sodium sulfate, the organic layer was concentrated to give an oil. The residue was purified by FC on silica gel (10% ethyl acetate in 60–80° C. petroleum ether) to give separation of the two isomers. The first higher $R_f$ fractions afforded pure title compound as the minor product as an oil.

$^1$H NMR (500 MHz, CDCl$_3$): δ 7.34–7.37 (m, 2H), 7.25–7.31 (m, 3H), 5.46 (s, 1H), 4.11–4.17 (m, 2H), 3.63 (s, 2H), 2.70–2.76 (m, 2H), 2.29 (tt, J=11.7 and 3.7 Hz, 1H), 1.75–1.80 (m, 2H), 1.47–1.61 (m, 2H), 1.47 (s, 9H).

MS (ESI): m/z 346 (M+1).

The lower $R_f$ fractions contained phenylacetone and major product 1-(1-t-butoxycarbonylpiperidin-4-yl)-2-phenylbutane-1,3-dione from which the latter crystallized on standing to give 7 g white solid (m.p. 105–106° C).

$^1$H NMR (360 MHz, CDCl$_3$): δ 15.23 (s, 1H), 7.3–7.45 (m, 3H), 7.15–7.2 (m, 2H), 4–4.1 (m, 2H), 2.35–2.50 (m, 2H), 2.2–2.3 (m, 1H), 1.87 (s, 3H), 1.5–1.75 (m, 4H), 1.43 (s, 9H).

MS (ESI): m/z 346 (M+1).

Method B:

Step 1: 1-t-Butoxycarbonylpiperidine-4-N-methyl-N-methoxycarboxamide

N-Boc isonipecotic acid (13.566 g, 59.2 mmol), N,O-dimethyl hydroxylamine hydrochloride (8.657 g, 88.7 mmol), and 1-hydroxybenzotriazole hydrate (15.99 g, 118.3 mmol) were dissolved in DMF (225 mL) in a 500 mL round-bottom flask and diisopropylethylamine (15.29 g, 20.6 mL, 118.3 mmol) was then added with stirring at RT. 1-Ethyl-3-(3-dimethylamino-propyl)carbodiimide (17.01 g, 88.74 mmol) was added in several portions over 10 min with stirring. After 22 h, the reaction mixture was poured into a water and ice mixture (600 mL) and was extracted with ethyl acetate (5×125 mL). The combined organic layers were washed with 1N HCl (2×200 mL), 5% sodium bicarbonate (2×200 mL), water and brine, dried over sodium sulfate and concentrated to give the title compound as a yellowish oil.

$^1$H NMR (500 MHz, CDCl$_3$): δ 4.11–4.20 (m, 2H), 3.72 (br s, 3H), 3.20 (br s, 3H), 2.75–2.86 (m, 3H), 1.63–1.76 (m, 4H), 1.47 (s, 9H).

Step 2: 4-Acetyl-1-t-butoxycarbonylpiperidine

After dissolving the above Weinreb amide in anhydrous ether (400 mL) under nitrogen and cooling the solution in an ice bath, 1.4M methyl magnesium bromide (55 mL) in 3:1 toluene and THF was added with stirring and cooling over 30 min. After stirring at 0° C. for 1 h, the reaction was poured into a mixture of ice water (400 mL) and acetic acid (0.8 mL, 150 mmol). The layers were separated and the aqueous layer was extracted twice with ether. The combined organic layers were washed with 0.1N HCl (200 mL), 3% sodium bicarbonate (200 mL), water (200 mL) and brine (200 mL), dried over sodium sulfate, and concentrated to give the crude product. FC (20–80% ethyl acetate in hexanes) gave the title compound as a yellowish oil. $R_f$: 0.27 (25% ethyl acetate in hexanes). Some starting Weinreb amide was also recovered. $R_f$: 0.10 (25% ethyl acetate in hexanes).

$^1$H NMR (500 MHz, CDCl$_3$): δ 4.07–4.14 (m, 2H), 2.75–2.83 (m, 2H), 2.46 (tt, J=11.3 and 3.8 Hz, 1H), 2.17 (s, 3H), 1.82–1.87 (m, 2H), 1.48–1.57 (m, 2H), 1.46 (s, 9H).

Step 3: 1-(1-(t-Butoxycarbonyl)piperidin-4-yl)-4-phenylbutane-1,3-dione

To a suspension of 60% sodium hydride (1.07 g) in THF (15 mL) at 0° C. was added a solution of the product of Step B2 (3.03 g, 13.3 mmol) and methyl phenylacetate (6.01 g, 39.9 mmol) in THF (6 mL) over 20 min. The reaction was stirred for another 4 h as it was allowed to warm to RT. The mixture was diluted with ether (30 mL) and poured into 1N HCl. The layers were separated and the aqueous layer was extracted three times with ether. The combined organic layers were washed with brine (150 mL), dried over sodium sulfate and concentrated. The crude product was purified by FC (20% ethyl acetate in hexanes) to give the title compound. $R_f$: 0.30 (20% ethyl acetate in hexane). Its NMR was the same as that obtained from the product of Method A above.

Step D: 4-(3-Benzyl-1-ethyl-(1H-pyrazol-5-yl))-1-tert-butoxy-carbonylpiperidine

Method A:

1-(1-t-Butoxycarbonylpiperidin-4-yl)-4-phenylbutane-1,3-dione (from Step A, either Method A or Method B), (0.851 g, 2.46 mmol) in methanol (25 mL) was added over 10 min to a suspension of ethylhydrazine oxalate (0.444 g, 2.96 mmol) in methanol (5 mL) in a 60° C. oil bath. After 15 h, the reaction was concentrated in vacuo and the residue was purified by repeated FC using a gradient of 50–100% ethyl acetate in hexanes to give first 4-(5-benzyl-1-ethyl-(1H-pyrazol-3-yl))-1-t-butoxycarbonylpiperidine as the higher $R_f$ product isomer and then the title compound as the lower $R_f$. $^1$H NMR (500 MHz): δ 7.26~7.31 (m, 4H), 7.19~7.23 (m, 1H), 5.72 (s, 1H), 4.16~4.24 (m, 2H), 4.08 (q, J=7.3 Hz, 2H), 3.94 (s, 2H), 2.76~2.82 (m, 2H), 2.66 (tt, J=3.6 & 11.9 Hz, 1H), 1.80~1.85 (m, 2H), 1.49~1.58 (m, 2H), 1.48 (s, 9H), 1.45 (t, J=7.3 Hz, 3H); ESI-MS 370.2 (M+H), HPLC A: 3.70 min. The other isomer's ESI-MS 370.2 (M+H), HPLC A: 3.77 min.

Method B:

Step 1: 1-t-Butoxycarbonyl-4-hydroxymethyl-piperidine

A solution of 25.03 g (109.2 mmol) N-Boc isonipecotic acid was dissolved in 200 mL THF and treated with 200 mL 1 M borane-tetrahydrofuran complex in THF, and the mixture was stirred overnight. The mixture was concentrated under vacuum, diluted with 750 mL ethyl acetate, and washed with 150 mL 1 N HCl (6×) and then saturated brine. The organic layer was dried over sodium sulfate and concentrated to give crude product as a white solid. $^1$H NMR (500 MHz) δ 4.15 (br d, J=13.7 Hz, 2H), 3.52 (d, J=6.2 Hz, 2H), 2.69~2.75 (m, 2H), 1.71~1.75 (m, 2H), 1.62~1.70 (m, 1H), 1.47 (s, 9H), 1.12~1.21 (m, 2H). This was used as is in the next step.

Step 2: 1-t-Butoxycarbonyl-4-formylpiperidine

A mixture of 17.62 g (135.6 mmol) oxalyl chloride and 250 mL DCM in a dry ice acetone bath was treated with a solution of 21.19 g (271.2 mmol) DMSO in 150 mL DCM over 20 min. After stirring for 20 min, a solution of 24.327 g of the product of Step 1 above in 150 mL DCM was added over 1 h. After an additional 15 min, 57.17 g (565 mmol) triethylamine in 150 mL DCM was added over 30 min. The reaction mixture was allowed to warm up over night in the cooling bath. The reaction mixture was concentrated under vacuum to remove about 400 mL DCM, and the residue was partitioned between 1 L ether and 300 mL water. To this was added 200 mL 1 N NaOH, the layers were separated, and the organic layer was washed with 150 mL 1 N NaOH (2×), water (3×), and saturated brine, dried over sodium sulfate, and concentrated to give crude product. FC (10~60% ethyl acetate in hexanes) gave the title compound as slightly yellowish oil. $R_F$: 0.29 (3:1 v/v hexanes/EtOAc); $^1$H NMR (500 MHz) δ 9.68 (d, J=0.7 Hz, 1H), 3.96~4.02 (m, 2H), 2.92~2.97 (m, 2H), 2.40~2.45 (m, 1H), 1.88~1.94 (m, 2H), 1.53~1.64 (m, 2H), 1.47 (s, 9H).

Step 3: 1-t-Butoxycarbonyl-4-(2,2-dibromoethen-1-yl)piperidine

A solution of 48.615 g (146.6 mmol) carbon tetrabromide in 150 mL DCM was added dropwise with stirring to a solution of 76.895 g (293.2 mmol) triphenylphosphine in 150 mL DCM in a 1-L rb flask with ice bath cooling over 1.75 h. After 40 min, a solution of 15.631 g (73.29 mmol) of the product of Step 2 above in 100 mL DCM was added to the resulting brown suspension with stirring and cooling over 40 min. After 1 h, 200 mL ether and 400 mL hexanes was added. The top suspension was filtered through Celite, and the residue was resuspended in 150 mL DCM and treated with 300 mL ether. The mixture was filtered, and the solid was washed with hexanes till total filtrate was 2 L. The filtrate was filtered again through Celite and washed with hexanes. The filtrate was washed with 100 mL 5% $NaHCO_3$, 300 mL water (2×), and 150 mL brine. The organic layer was dried over $Na_2SO_4$ and concentrated under vacuum to give crude product as a yellowish solid. Flash chromatography (FC) on 250 g silica gel (0~15% EtOAc in hexanes) gave title compound as a white solid. $R_F$: 0.57 (15% EtOAc in hexanes); $^1$H NMR (500 MHz) δ 6.25 (d, J=8.9 Hz, 1H), 4.04~4.12 (m, 2H), 2.75~2.83 (m, 2H), 2.42~2.50 (m, 1H), 1.69~1.75 (m, 2H), 1.47 (s, 9H), 1.29~1.37 (m, 2H).

Step 4: 1-(t-Butoxycarbonyl)-4-(2-tributylstannylethyn-1-yl)-piperidine

A mixture of 23.199 g (62.85 mmol) of the product of Step 3 above and 600 mL anhydrous THF was cooled with dry ice acetone bath under nitrogen. To this mixture was added 88 mL of a 1.6 M BuLi solution in hexanes dropwise with stirring and cooling over 50 min. After 1 h, the flask was transferred into an ice bath. After another hour, a solution of 28.64 g (87.99 mmol) tributyltin chloride in 100 mL THF was added with stirring and cooling over 35 min. After 3 h, the mixture was concentrated under vacuum to remove some THF, and the residue was partitioned between 600 mL ice water and 800 mL ether. The organic layer was washed with 200 mL of water (1×), 2% $NaHCO_3$ (1×), water (2×), and saturated brine (1×), dried over $Na_2SO_4$ and concentrated under vacuum to give crude product as a green-yellowish liquid. FC on 275 g silica gel using cold 2.5~15% EtOAc in hexanes as quickly as possible to give the title compound as a colorless liquid. $R_F$: 0.45 (10% EtOAc in hexanes); $^1$H NMR (500 MHz) δ 3.63~3.67 (m, 2H), 3.25~3.30 (m, 2H), 2.64~2.69 (m, 1H), 1.74~1.79 (m, 2H), 1.54~1.64 (m, 8H), 1.47 (s, 9H), 1.32~1.39 (m, 6H), 0.96~0.99 (m, 6H), 0.92 (t, J=7.3 Hz, 9H).

Step 5: 4-(1-t-Butoxycarbonylpiperidin-4-yl)-1-phenyl-2-butanon-3-yne

To a mixture of 1.727 g (3.466 mmol) of the product of Step 4 above in 18 mL 1,2-dichloroethane was added 0.536 g (3.466 mmol) phenylacetyl chloride and 50 mg dichlorobis (triphenylphosphine)palladium (11). The mixture was refluxed under nitrogen for 2 h, then concentrated under vacuum. Purifying the residue on silica gel (5~35% ethyl acetate in hexanes) gave the title compound as a yellow oil. $R_F$: 0.27 (20% EtOAc in hexanes); $^1$H NMR (500 MHz) δ 7.34~7.38 (m, 2H), 7.28~7.32 (m, 1H), 7.24~7.27 (m, 2H), 3.82 (s, 2H), 3.49~3.54 (m, 2H), 3.17~3.23 (m, 2H), 2.68~2.73 (m, 1H), 1.72~1.77 (m, 2H), 1.51~1.57 (m, 2H), 1.47 (s, 9H). Tetrakis(triphenylphosphine)palladium gave a similar result.

Step 6: 4-(3-Benzyl-1-ethyl-(1H-pyrazol-5-yl))-1-tert-butoxycarbonyl-piperidine

Heating 1.204 g (3.677 mmol) of the product of Step 5 above with 0.662 g (4.413 mmol) ethylhydrazine oxalate and 1.252 g (9.687 mmol) DIEA in 20 mL ethanol overnight gave 8:1 ratio of the title compound and its isomer 4-(5-benzyl-1-ethyl-(1H-pyrazol-3-yl))-1-tert-butoxycarbonylpiperidine. Use of ethylhydrazine free base gave even more favorable ratios of the desired title compound. The desired isomer can be isolated by recrystallization using hexanes or by silica gel chromatography using 5~10% MeCN in DCM in addition to the procedure described in Method A above.

Step E: 4-(3-Benzyl-1-ethyl-(1H-pyrazol-5-yl))piperidine, HCl salt

Into a stirring solution of the title compound in Step D (29 mmol, 10.0 g) in 200 mL of methanol was slowly bubbled HCl (g) for 1.5 h at 0° C., after which time HPLC analysis indicated the deprotection was complete. The solvent was removed under reduced pressure affording the title compound as a white solid. MS (ESI): m/z 270 (M+H). HPLC B: 0.89 min.

Step F: tert-Butyl-(1S)-1-phenyl-3-(4-[3-benzyl-1-ethyl (1H-pyrazol-5-yl)]piperidin-1-yl)propylcarbamate To a solution of the title compound from Step B (10 mmol, 2.5 g was added the product of Step E (11 mmol, 4.5 g) and N,N-diisopropylethylamine (40 mmol, 7 mL) in 40 mL of DCM was added $NaBH(OAc)_3$ (30 mmol, 6.4 g). The slurry was sonicated briefly and the reaction mixture was allowed to stand at RT for 1 h. The reaction mixture was washed with 20 mL of $H_2O$. The organic phase was dried with $MgSO_4$ and the solvent was removed under reduced pressure. The residue was purified by silica gel chromatography eluting with 1:20:79 $NH_4OH$/EtOAc/hexanes and 1:40:59 $NH_4OH$/EtOAc/hexanes, affording the title compound as a white foamy solid. MS (ESI): m/z 503 (M+H). HPLC B: 1.78 min.

Step G: (1S)-1-phenyl-3-(4-[3-benzyl-1-ethyl(1H-pyrazol-5-yl)]piperidin-1-yl)propylamine, tris-HCl salt The title compound from Step F (2.7 mmol, 2.0 g) was stirred in 50 mL of a premixed solution of 10:1 (v/v) of methanol/acetyl chloride. After 4 h the solvent was removed under reduced pressure, affording the title compound as a white solid. MS (ESI): m/z 403 (M+H). HPLC B: 1.00 min.

EXAMPLE 14A

N-[1(S)-1-phenyl-3-(4-[3-benzyl-1-ethyl(1H-pyrazol-5-yl)] piperidin-1-yl)propyl]methylsulfonamide, bis-TFA salt To a solution of the title compound from Reference Example 1, Step G (0.06 mmol, 32 mg) and N,N-diisopropylethylamine (0.4 mmol, 70 μL) in DCM (1 mL) was added methanesulfonyl chloride (0.1 mmol, 8 μL). After 2 h the reaction was quenched by addition of 0.15 mL of methanol. The solvent was removed under a stream of nitrogen. The residue was taken up in 1:1 dioxane/$H_2O$ and purified by reverse-phase HPLC. Lyophilization of the product afforded the title compound as a white solid. MS (ESI): m/z 481 (M+H). HPLC B: 1.37 min.

EXAMPLES 14B AND 14C

The following compounds were prepared by a procedure analogous to that set forth in Example 14A.

| Example No. | MS (ESI) | HPLC B |
|---|---|---|
| 14B: N-{(1S)-3-[4-(3-benzyl-1-ethyl-1H-pyrazol-5-yl)piperidin-1-yl]-1-phenylpropyl}ethanesulfonamide, bis trifluoroacetate salt | 495 (M + H) | 1.44 min |
| 14C: N-{(1S)-3-[4-(3-benzyl-1-ethyl-1H-pyrazol-5-yl)piperidin-1-yl]-1-phenylpropyl}thiophene-2-sulfonamide, bis trifluoroacetate salt | 549 (M + H) | 1.32 min |

EXAMPLE 15

4-(3-benzyl-1-ethyl-1H-pyrazol-1-ium-5-yl)-1-[(3S)-3-phenyl-3-(phenylsulfonylaminocarbonylamino)propyl]piperidinium bis(trifluoroacetate)

To the a solution of the title amine from Reference Example 1, Step G (0.06 mmol, 31 mg) and DIEA (0.24 mmol, 42 µL) in 1 mL of DCM was added phenylsulfonylisocyanate (0.08 mmol, 15 mg). After 30 min and additional 0.08 mmol of phenylsulfonylisocyanate was added to the reaction. After 1 h the mixture was loaded onto a Varian Bond Elut® SCX ion-exchange cartridge (2 g) and washed with 25 mL of methanol. The product was eluted with 25 mL of 2M ammonia in methanol. The solvent was removed under a stream of nitrogen, and the residue was purified by reverse-phase chromatography. Lyophilization afforded 33 mg of the title compound as a white solid. MS (ESI): m/z 586 (M+1). HPLC B: 1.69 min.

What is claimed is:

1. A compound of the formula I:

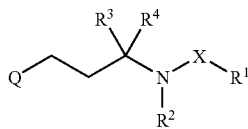

(I)

wherein:

Q is

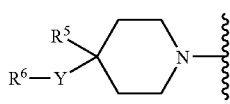

$R^5$ is hydrogen;
$R^6$ is pyrazole, which is optionally substituted with one or two groups chosen from methyl, ethyl and benzyl;
Y is a single bond or $CH_2$;
$R^3$ is phenyl;
$R^4$ is hydrogen;
$R^2$ is hydrogen;
X is —$SO_2$— or —C(=O)N($R^2$)$SO_2$—; or
$R^1$ is phenyl or thiophenyl;
or a pharmaceutically acceptable salt thereof.

2. The compound of claim 1 wherein $R^6$ is 1,3-dimethylpyrazol-5-yl or 1-ethyl-3-benzylpyrazol-5yl.

3. The compound of claim 1 wherein Y is a single bond.

4. The compound of claim 1 wherein X is —C(=O)N($R^2$)$SO_2$— where $R^2$ is hydrogen.

5. The compound of claim 1 wherein $R^1$ is phenyl or thiophen-2-yl.

6. A compound which is selected from the group consisting of:
   N-{3-[4-(2-methyl-2H-pyrazol-3-yl)piperidin-1-yl]-1-phenylpropyl}-benzenesulfonamide;
   (R)-N-{3-[4-(2-ethyl-5-methyl-2H-pyrazol-3-yl)piperidin-1-yl]-1-phenylpropyl}-N-methylbenzenesulfonamide;
   N-{1-(4-chlorophenyl)-3-[4-(2-ethyl-5-methyl-2H-pyrazol-3-yl)piperidin-1-yl]propyl}-N-methylbenzenesulfonamide;
   4-bromo-N-{3-[4-(2-ethyl-5-methyl-2H-pyrazol-3-yl)piperidin-1-yl]-1-phenylpropyl}benzenesulfonamide;
   3-bromo-N-{3-[4-(2-ethyl-5-methyl-2H-pyrazol-3-yl)piperidin-1-yl]-1-phenylpropyl}benzenesulfonamide;
   N-{3-[4-(2-ethyl-5-methyl-2H-pyrazol-3-yl)piperidin-1-yl]-1-phenylpropyl}-4-fluorobenzenesulfonamide;
   N-{3-[4-(2-ethyl-5-methyl-2H-pyrazol-3-yl)piperidin-1-yl]-1-phenylpropyl}-N-phenylmethanesulfonamide;
   1-methyl-1H-imidazole-4-sulfonic acid {3-[4-(2-ethyl-5-methyl-2H-pyrazol-3-yl)-piperidin-1-yl]-1-phenylpropyl}amide;
   5-bromothiophene-2-sulfonic acid {3-[4-(2-ethyl-5-methyl-2H-pyrazol-3-yl)piperidin-1-yl]-1-phenylpropyl}amide;
or a pharmaceutically acceptable salt thereof.

7. A compound which is:
   (R)-N-{3-[4-(2-ethyl-5-methyl-2H-pyrazol-3-yl)piperidin-1-yl]-1-phenylpropyl}-N-methylbenzenesulfonamide;
or a pharmaceutically acceptable salt thereof.

8. A pharmaceutical composition comprising an effective amount of the compound of claim 1 and a pharmaceutically acceptable excipient.

9. A pharmaceutical composition comprising an effective amount of the compound of claim 6 and a pharmaceutically acceptable excipient.

10. A method of treatment of schizophrenia in a human patient in need thereof which comprises administering to the patient a therapeutically effective amount of the compound of claim 1 or a pharmaceutically acceptable salt thereof.

11. A method of treatment of schizophrenia in a human patient in need thereof which comprises administering to the patient a therapeutically effective amount of the compound of claim 6 or a pharmaceutically acceptable salt thereof.

* * * * *